(12) United States Patent
Sichwart et al.

(10) Patent No.: US 8,986,960 B2
(45) Date of Patent: Mar. 24, 2015

(54) MICROORGANISMS WITH EXTENDED SUBSTRATE UTILIZATION RANGE

(75) Inventors: Shanna Sichwart, Pforzheim (DE); Birgit Haschenhermes, Meppen (DE); Daniel Bröker, Nienberge (DE); Alexander Steinbüchel, Altenberge (DE); Stephan Hetzler, Munster (DE); Perttu Koskinen, Helsinki (FI)

(73) Assignee: Neste Oil Oyj, Espoo (FI)

( * ) Notice: Subject to any disclaimer, the term of this patent is extended or adjusted under 35 U.S.C. 154(b) by 476 days.

(21) Appl. No.: 13/183,638

(22) Filed: Jul. 15, 2011

(65) Prior Publication Data
US 2012/0015413 A1    Jan. 19, 2012

Related U.S. Application Data

(60) Provisional application No. 61/364,898, filed on Jul. 16, 2010.

(30) Foreign Application Priority Data

Jul. 16, 2010   (EP) .................................... 10169808

(51) Int. Cl.
| | | |
|---|---|---|
| *C12N 9/90* | (2006.01) | |
| *C12N 1/20* | (2006.01) | |
| *C12N 1/22* | (2006.01) | |
| *C12N 9/02* | (2006.01) | |
| *C12N 9/12* | (2006.01) | |
| *C12P 7/62* | (2006.01) | |

(52) U.S. Cl.
CPC .. *C12N 9/90* (2013.01); *C12N 1/20* (2013.01); *C12N 1/22* (2013.01); *C12N 9/001* (2013.01); *C12N 9/1205* (2013.01); *C12P 7/625* (2013.01)
USPC ........... 435/134; 435/6; 435/69.1; 435/320.1; 435/252

(58) Field of Classification Search
None
See application file for complete search history.

(56) References Cited

FOREIGN PATENT DOCUMENTS

| JP | 2009225662 | 10/2009 |
| WO | 2009081941 | 7/2009 |

OTHER PUBLICATIONS

Steinbuchnel et al. (TIBTECH, 1998, vol. 16, pp. 419-427).*
Sichwart et al. (Applied & Environ. Microbiol., vol. 77, No. 4, 2011, pp. 1325-1334).*
Mergeay et al. (J. of Bacteriol., 1985, vol. 162, No. 1, pp. 328-334).*
Pohlmann et al. (Nature Biotech., 2007, vol. 25, No. 4, pp. 1-7).*
Altschul et al., "Basic local alignment search tool", J. Mol. Bio., 1990, 215:403-410.
Altschul et al., "Gapped BLAST and PSI-BLAST: a new generation of protein database search programs", Nucleic Acids Research, 1997, 25(17):3389-3402.
Birnboim et al., "A rapid alkaline extraction procedure for screening recombinant plasmid DNA", Nucleic Acids Research, 1979, 7(6):1513-1523.
Bradford, "A rapid and sensitive method for the quantitation of microgram quantities of protein utilizing the principle of protein-dye binding", Analytical Biochemistry, 1976, 72:248-254.
Franklin et al., "Molecular and functional analysis of the TOL plasmid pWWO from *Pseudomonas putida* and cloning of genes for the entire regulated aromatic ring meta cleavage pathway", Proc. Natl. Acad. Sci. USA, Dec. 1981, 78(12):7458-7462.
Friedrich et al., "Naturally occurring genetic transfer of hydrogen-oxidizing ability between strains of *Alcaligenes eutrophus*", Journal of Bacteriology, Jul. 1981, 147(1):198-205.
Hirota et al., "On the process of cellular division in *Escherichia coli*: a mutant of *E. coli* lacking a murein-lipoprotein", Proc. Natl. Acad. Sci. USA, Apr. 1977, 74(4)1417-1420.
Jeffke et al., "Mutational analysis of the cbb operon ($CO_2$ Assimilation) promoter of *Ralstonia eutropha*", Journal of Bacteriology, Jul. 1999, 181(14):4374-4380.
Kalscheuer et al., "Microdiesel: *Escherichia coli* engineered for fuel production", Microbiology, 2006, 152:2529-2536.
Kang et al., "Induction of capsular polysaccharide synthesis by p-Fluorophenylalanine in *Escherichia coli* wild type and strains with altered phenylalanyl soluble ribonucleic acid synthetase", Journal of Bacteriology, Feb. 1967, 93 (2):584-591.
Kovach et al., "Four new derivatives of the broad-host-range cloning vector pBBR1MCS, carrying different antibiotic-resistance cassettes", Gene, 1995, 166:175-176.
Laemmli, "Cleavage of structural proteins during the assembly of the head of bacteriophage T4", Nature, Aug. 15, 1970, 227:680-685.
Meijnen et al., "Engineering *Pseudomonas putida* S12 for efficient utilization of D-Xylose and L-Arabinose", Applied and Environmental Microbiology, Aug. 2008, 74(16):5031-5037.
Peplinski et al., "Genome-wide transcriptome analyses of the 'Knallgas' bacterium *Ralstonia eutropha* H16 with regard to polyhydroxylakanoate metabolism", Microbiology, 2010, 156:2136-2152.
Schaferjohann et al., "Regulation of $CO_2$ assimilation in *Ralstonia eutropha*: premature transcription termination within the cbb operon", Journal of Bacteriology, Dec. 1996, 178(23):6714-6719.
Schwartz et al., "Transcriptional regulation of *Alcaligenes eutrophus* hydrogenase genes", Journal of Bacteriology, Jun. 1998, 180(12):3197-3204.
Shamanna et al., "Uptake and catabolism of D-Xylose in *Salmonella typhimurium* LT2", Journal of Bacteriology, Jul. 1979, 139(1):64-70.
Siedow et al., "A megaplasmid-borne anaerobic ribonucleotide reductase in *Alcaligenes eutrophus* H16", Journal of Bacteriology, Aug. 1999, 181(16):4919-4928.

(Continued)

*Primary Examiner* — Hope Robinson
(74) *Attorney, Agent, or Firm* — Andrus Intellectual Property Law, LLP

(57) ABSTRACT

Disclosed are microorganisms of the genus *Cupriavidus* or *Ralstonia*, which are genetically modified to express phosphomannose isomerase (EC5.3.1.8) and facilitated diffusion protein (EC1.3.1.74) for mannose uptake, and optionally mannofructokinase (EC2.7.1.4). The microorganisms also may be genetically modified to express xylose isomerase (EC 5.3.1.5), xylulokinase (E 2.7.1.17) and xylose proton symporter E or a high affinity ABC-transporter. The genetically modified microorganisms are capable of growing on mannose, xylose, arabinose, glucose, or galactose, or a combination thereof as the carbon source.

24 Claims, 6 Drawing Sheets

(56) References Cited

OTHER PUBLICATIONS

Verlinden et al., "Bacterial synthesis of biodegradable polyhydroxyalkanoates", Journal of Applied Microbiology, 2007, 102, 1437-1449.

Weber et al., "The reliability of molecular weight determinations by dodecyl sulfate-polyacrylamide gel electrophoresis", Journal of Biological Chemistry, Aug. 25, 1969, 244(16):4406-4412.

Anderson et al., "D-Fructose (D-Mannose) Kinase", Methods Enzymol., 1975, 42:39-43.

Aneja et al., "Altered composition of *Ralstonia eutropha* poly(hydroxyalkanoate) through expression of PHA synthase from *Allochromatium vinosum* ATCC 35206", Biotechnol Lett, 2009, 31:1601-1612.

Buchholz et al., "Transfer of Genes from *Pseudomonas saccharaphila* to construct xylose-utilizing strains of *Alcaligenes eutrophus*", Current Microbiology, 1994, 29:157-162.

Chaillou et al., "Molecular Cloning and Functional Expression in *Lactobacillus plantarum* 80 of xlyT, encoding the D-xylose-H+ symporter of *Lactobacillus brevis*", Applied and Environmental Microbiology, Dec. 1998, 64(12):4720-4728.

Coulombel et al., "Identification and kinetic studies of an inducible mannokinase from a *Streptomyces* strain", Biochimica et Biophysica Acta, 1982, 706:117-122.

Eliasson et al., "Xylulose fermentation by mutant and wild-type strains of *Zygosaccharomyces* and *Saccharomyces cerevisiae*", Appl Microbiol Biotechnol, 2000, 53:376-382.

Gao et al., "Characterization of Heterologous and Native Enzyme Activity Profiles in Metabolically Engineered *Zymomonas mobilis* Strains During Batch Fermentation of Glucose and Xylose Mixtures", Applied Biochemistry andBiotechnology, 2002, 98-100:341.

Ghangas et al., "Isolation and Characterization of the *Salmonella typhimurium* LT2 xylose regulon", Journal of Bacteriology, Jan. 1984, 157(1):158-164.

Gottschalk et al., "Verwertung von Fructose durch Hydrogenomonas H16(I.)" Archiv Fur Mikrobiologie, 1964, 48:95-108.

Gu et al., "Reconstruction of xylose utilization pathway and regulons in firmicutes", BMC Genomics, 2010, 11:255.

Hanahan, "Studies on Transformation of *Escherichia coli* with Plasmids", J. Mol. Biol., 1983, 166:557-580.

Konig et al., "Konstitutive Glucose-6-phosphat-Dehydrogenase bei Glucose verwertenden Mutanten von einem kryptischen Wildstamm", Arch. Mikrobiol., 1969, 67:51-57.

Laikova et al., "Computational analysis of the transcriptional regulation of pentose utilization systems in the gamma subdivision of Proteobacteria", FEMS Microbiology Letters, 2001, 205:315-322.

Koller et al., "Production of Polyhydroxyalkanoates from Agricultural Waste and Surplus Materials", Biomacromolecules, 2005, 6:561-565.

Meijnen et al., "Construction of a xylose-utilizing *Pseudomonas putida* for the bioproduction of fine chemicals", Journal of Biotechnology, 2007, 131S:S206.

Park et al., "High frequency transformation of *Alcaligenes eutrophus* producing poly-beta-hydroxybutyric acid by electroporation", Biotechnolgy Techniques, Jan. 1995, 9(1):31-34.

Parker et al., "Characterization of the *Zymomonas mobilis* glucose facilitator gene product (glf) in recombinant *Escherichia coli*: examination of transport mechanism, kinetics and the role of glucokinase in glucose transport", Molecular Microbiology, 1995, 15(5):795-802.

Pohlmann et al., "Genome sequence of the bioplastic-producing 'Knallgas' bacterium *Rastonia eutropha* H16", Nature Biotechnology, 2007, 24:1257-1262.

Porthun et al., "Expression of a functional NAD-reducing [NiFe] hydrogenase from the gram-positive *Rhodococcus opacus* in the gram-negative *Ralstonia eutropha*", Arch Microbiol, 2002, 177:159-166.

Povolo et al., "Polyhydroxyalkanoates production by engineered *Cupriavidus necator* from waste material containing lactose", Bioresource Technology, 2010, 101:7902-7907.

Pries et al., "Lactose- and galactose-utilizing strains of poly(hydroxyalkanoic acid)-accumulating *Alcaligenes eutrophus* and *Pseudomonas saccharophila* obtained by recombinant DNA technology", Appl. Microbiol Biotechnol, 1990, 33:410-417.

Reinecke et al., "*Ralstonia eutropha* strain H16 as model organism for PHA metabolism and for biotechnological production of technically interesting biopolymers", Journal of Molecular Microbiology and Biotechnology, 2009, 16:91-108.

Rodionov et al., "Transcriptional regulation of pentose utilisation systems in the *Bacillus/Clostridium* group of bacteria", FEMS Microbiology Letters, 2001, 205:305-314.

Schlegel et al., "Verwertung von Glucose durch eine Mutante von Hydrogenomonas H16", Biochemische Zeitschrift, 1965, 341:249-259.

Schlegel et al., "Ein Submersvafahren zur Kultur wasserstoffoxydierender Bakterien: Wachstumsphysiologische Untersuchungen", Archiv fur Mikrobiologie, 1961, 38:209-222.

Sebastian et al., "Identification of a Mannokinase in *Escherichia coli*", Biochemical and Biophysical Research Communications, 1967, 28(2):197.

Sichwart et al., "Extension of the substrate utilization range of *Ralstonia eutropha* strain H16 by metabolic engineering to include mannose and glucose", Applied and Environmental Microbiology, Feb. 2011, 77 (4):1325-1334.

Simon et al., "A broad host range mobilization system for in vivo genetic engineering: transposon mutagenesis in gram negative bacteria", BioTechnology, Nov. 1983, 784.

Sofia et al., "Analysis of the *Escherichia coli* genome. V. DNA sequence of the region from 76.0 to 81.5 minutes", Nucleic Acids Research, 1994, 22(13):2576-2586.

Solaiman et al., "A new shuttle vector for gene expression in biopolymer-producing *Ralstonia eutropha*", Journal of Microbiological Methods, 2010, 82:120-123.

Solaiman et al., "Isolation of novel *Pseudomonas syringae* promoters and functional characterization in polyhydroxyalkanoate-producing pseudomonads", New Biotechnology, Feb. 2010, 27(1):1.

Solaiman et al., "Conversion of agricultural feedstock and coproducts into poly(hydroxyalkanoates)", Appl Microbiol Biotechnol, 2006, 71:783-789.

Weisser et al., "Expression of the *Escherichia coli* pmi gene, encoding phosphomannose-isomerase in *Zymomonas mobilis*, leads to utilization of mannose as a novel growth substrate, which can be used as a selective marker", Applied and Environmental Microbiology, Nov. 1996, 62(11):4155-4161.

West et al., "Construction of improved *Escherichia-Pseudomonas* shuttle vectors derived from pUC18/19 and sequence of the region required for their replication in *Pseudomonas aeruginosa*", Gene, 1994, 128:81-86.

Windhovel et al., "On the operon structure of the cfx gene clusters in *Alcaligenes eutrophus*", Arch Microbiol, 1990, 154:85-91.

Database WPI, Week 200974, Thomson Scientific, London, GB, Kaneka Corp, Oct. 8, 2009.

International Search Report and Written Opinion for PCT/FI2011/050657 dated Nov. 9, 2011.

European Search Report for EP10169808 dated Mar. 1, 2011.

* cited by examiner

SEQUENCE LISTING

```
<160> NUMBER OF SEQ ID NOS: 95

<210> SEQ ID NO 1
<211> LENGTH: 391
<212> TYPE: PRT
<213> ORGANISM: Escherichia coli

<400> SEQUENCE: 1

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140
```

```
Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
210                 215                 220

Pro Glu Asp Ser Gly Leu Phe Ser Pro Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Asn Gln Leu Leu Thr Gln
290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
        355                 360                 365

Ile Ala Ala Asn Glu Ser Pro Val Thr Val Lys Gly His Gly Arg Leu
370                 375                 380

Ala Arg Val Tyr Asn Lys Leu
385                 390

<210> SEQ ID NO 2
<211> LENGTH: 473
<212> TYPE: PRT
<213> ORGANISM: Zymomonas mobilis

<400> SEQUENCE: 2

Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
                20                  25                  30

Ala Ile Gly Thr Pro Val Asp Ile His Phe Ile Ala Pro Arg His Leu
            35                  40                  45

Ser Ala Thr Ala Ala Ala Ser Leu Ser Gly Met Val Val Ala Val
        50                  55                  60

Leu Val Gly Cys Val Thr Gly Ser Leu Leu Ser Gly Trp Ile Gly Ile
65                  70                  75                  80

Arg Phe Gly Arg Arg Gly Gly Leu Leu Met Ser Ser Ile Cys Phe Val
                85                  90                  95

Ala Ala Gly Phe Gly Ala Ala Leu Thr Glu Lys Leu Phe Gly Thr Gly
            100                 105                 110

Gly Ser Ala Leu Gln Ile Phe Cys Phe Phe Arg Phe Leu Ala Gly Leu
```

```
                    115                 120                 125
Gly Ile Gly Val Val Ser Thr Leu Thr Pro Thr Tyr Ile Ala Glu Ile
        130                 135                 140

Ala Pro Pro Asp Lys Arg Gly Gln Met Val Ser Gln Gln Met Ala
145                 150                 155                 160

Ile Val Thr Gly Ala Leu Thr Gly Tyr Ile Phe Thr Trp Leu Leu Ala
                165                 170                 175

His Phe Gly Ser Ile Asp Trp Val Asn Ala Ser Gly Trp Cys Trp Ser
            180                 185                 190

Pro Ala Ser Glu Gly Leu Ile Gly Ile Ala Phe Leu Leu Leu Leu
                195                 200                 205

Thr Ala Pro Asp Thr Pro His Trp Leu Val Met Lys Gly Arg His Ser
    210                 215                 220

Glu Ala Ser Lys Ile Leu Ala Arg Leu Glu Pro Gln Ala Asp Pro Asn
225                 230                 235                 240

Leu Thr Ile Gln Lys Ile Lys Ala Gly Phe Asp Lys Ala Met Asp Lys
                245                 250                 255

Ser Ser Ala Gly Leu Phe Ala Phe Gly Ile Thr Val Val Phe Ala Gly
            260                 265                 270

Val Ser Val Ala Ala Phe Gln Gln Leu Val Gly Ile Asn Ala Val Leu
        275                 280                 285

Tyr Tyr Ala Pro Gln Met Phe Gln Asn Leu Gly Phe Gly Ala Asp Thr
290                 295                 300

Ala Leu Leu Gln Thr Ile Ser Ile Gly Val Val Asn Phe Ile Phe Thr
305                 310                 315                 320

Met Ile Ala Ser Arg Val Val Asp Arg Phe Gly Arg Lys Pro Leu Leu
                325                 330                 335

Ile Trp Gly Ala Leu Gly Met Ala Ala Met Met Ala Val Leu Gly Cys
            340                 345                 350

Cys Phe Trp Phe Lys Val Gly Gly Val Leu Pro Leu Ala Ser Val Leu
        355                 360                 365

Leu Tyr Ile Ala Val Phe Gly Met Ser Trp Gly Pro Val Cys Trp Val
    370                 375                 380

Val Leu Ser Glu Met Phe Pro Ser Ser Ile Lys Gly Ala Ala Met Pro
385                 390                 395                 400

Ile Ala Val Thr Gly Gln Trp Leu Ala Asn Ile Leu Val Asn Phe Leu
                405                 410                 415

Phe Lys Val Ala Asp Gly Ser Pro Ala Leu Asn Gln Thr Phe Asn His
            420                 425                 430

Gly Phe Ser Tyr Leu Val Phe Ala Ala Leu Ser Ile Leu Gly Gly Leu
        435                 440                 445

Ile Val Ala Arg Phe Val Pro Glu Thr Lys Gly Arg Ser Leu Asp Glu
    450                 455                 460

Ile Glu Glu Met Trp Arg Ser Gln Lys
465                 470

<210> SEQ ID NO 3
<211> LENGTH: 302
<212> TYPE: PRT
<213> ORGANISM: Escherichia coli

<400> SEQUENCE: 3

Met Arg Ile Gly Ile Asp Leu Gly Gly Thr Lys Thr Glu Val Ile Ala
1               5                   10                  15
```

```
Leu Gly Asp Ala Gly Glu Gln Leu Tyr Arg His Arg Leu Pro Thr Pro
            20                  25                  30

Arg Asp Asp Tyr Arg Gln Thr Ile Glu Thr Ile Ala Thr Leu Val Asp
        35                  40                  45

Met Ala Glu Gln Ala Thr Gly Gln Arg Gly Thr Val Gly Met Gly Ile
 50                  55                  60

Pro Gly Ser Ile Ser Pro Tyr Thr Gly Val Val Lys Asn Ala Asn Ser
65                   70                  75                  80

Thr Trp Leu Asn Gly Gln Pro Phe Asp Lys Asp Leu Ser Ala Arg Leu
                85                  90                  95

Gln Arg Glu Val Arg Leu Ala Asn Asp Ala Asn Cys Leu Ala Val Ser
            100                 105                 110

Glu Ala Val Asp Gly Ala Ala Gly Ala Gln Thr Val Phe Ala Val
            115                 120                 125

Ile Ile Gly Thr Gly Cys Gly Ala Gly Val Ala Phe Asn Gly Arg Ala
            130                 135                 140

His Ile Gly Gly Asn Gly Thr Ala Gly Glu Trp Gly His Asn Pro Leu
145                 150                 155                 160

Pro Trp Met Asp Glu Asp Glu Leu Arg Tyr Arg Glu Val Pro Cys
                165                 170                 175

Tyr Cys Gly Lys Gln Gly Cys Ile Glu Thr Phe Ile Ser Gly Thr Gly
            180                 185                 190

Phe Ala Met Asp Tyr Arg Arg Leu Ser Gly His Ala Leu Lys Gly Ser
                195                 200                 205

Glu Ile Ile Arg Leu Val Glu Glu Ser Asp Pro Val Ala Glu Leu Ala
210                 215                 220

Leu Arg Arg Tyr Glu Leu Arg Leu Ala Lys Ser Leu Ala His Val Val
225                 230                 235                 240

Asn Ile Leu Asp Pro Asp Val Ile Val Leu Gly Gly Met Ser Asn
            245                 250                 255

Val Asp Arg Leu Tyr Gln Thr Val Gly Gln Leu Ile Lys Gln Phe Val
            260                 265                 270

Phe Gly Gly Glu Cys Glu Thr Pro Val Arg Lys Ala Lys His Gly Asp
            275                 280                 285

Ser Ser Gly Val Arg Gly Ala Ala Trp Leu Trp Pro Gln Glu
    290                 295                 300

<210> SEQ ID NO 4
<211> LENGTH: 440
<212> TYPE: PRT
<213> ORGANISM: Escherichia coli

<400> SEQUENCE: 4

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
                20                  25                  30

Val Leu Gly Lys Arg Met Glu Glu His Leu Arg Phe Ala Ala Cys Tyr
            35                  40                  45

Trp His Thr Phe Cys Trp Asn Gly Ala Asp Met Phe Gly Val Gly Ala
 50                  55                  60

Phe Asn Arg Pro Trp Gln Gln Pro Gly Glu Ala Leu Ala Leu Ala Lys
65                   70                  75                  80

Arg Lys Ala Asp Val Ala Phe Glu Phe Phe His Lys Leu His Val Pro
                85                  90                  95
```

Phe Tyr Cys Phe His Asp Val Asp Val Ser Pro Gly Ala Ser Leu
            100                 105                 110

Lys Glu Tyr Ile Asn Asn Phe Ala Gln Met Val Asp Val Leu Ala Gly
        115                 120                 125

Lys Gln Glu Ser Gly Val Lys Leu Leu Trp Gly Thr Ala Asn Cys
130                 135                 140

Phe Thr Asn Pro Arg Tyr Gly Ala Gly Ala Thr Asn Pro Asp Pro
145                 150                 155                 160

Glu Val Phe Ser Trp Ala Ala Thr Gln Val Val Thr Ala Met Glu Ala
            165                 170                 175

Thr His Lys Leu Gly Gly Glu Asn Tyr Val Leu Trp Gly Gly Arg Glu
        180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
            325                 330                 335

Asn Phe Asp Ala Lys Val Arg Arg Gln Ser Thr Asp Lys Tyr Asp Leu
        340                 345                 350

Phe Tyr Gly His Ile Gly Ala Met Asp Thr Met Ala Leu Ala Leu Lys
    355                 360                 365

Ile Ala Ala Arg Met Ile Glu Asp Gly Glu Leu Asp Lys Arg Ile Ala
370                 375                 380

Gln Arg Tyr Ser Gly Trp Asn Ser Glu Leu Gly Gln Ile Leu Lys
385                 390                 395                 400

Gly Gln Met Ser Leu Ala Asp Leu Ala Lys Tyr Ala Gln Glu His His
            405                 410                 415

Leu Ser Pro Val His Gln Ser Gly Arg Gln Glu Gln Leu Glu Asn Leu
        420                 425                 430

Val Asn His Tyr Leu Phe Asp Lys
    435                 440

<210> SEQ ID NO 5
<211> LENGTH: 484
<212> TYPE: PRT
<213> ORGANISM: Escherichia coli

<400> SEQUENCE: 5

Met Tyr Ile Gly Ile Asp Leu Gly Thr Ser Gly Val Lys Val Ile Leu
1               5                   10                  15

Leu Asn Glu Gln Gly Glu Val Val Ala Ala Gln Thr Glu Lys Leu Thr

```
                 20                  25                  30
Val Ser Arg Pro His Pro Leu Trp Ser Glu Gln Asp Pro Glu Gln Trp
             35                  40                  45

Trp Gln Ala Thr Asp Arg Ala Met Lys Ala Leu Gly Asp Gln His Ser
 50                  55                  60

Leu Gln Asp Val Lys Ala Leu Gly Ile Ala Gly Gln Met His Gly Ala
 65                  70                  75                  80

Thr Leu Leu Asp Ala Gln Gln Arg Val Leu Arg Pro Ala Ile Leu Trp
                 85                  90                  95

Asn Asp Gly Arg Cys Ala Gln Glu Cys Thr Leu Leu Glu Ala Arg Val
                100                 105                 110

Pro Gln Ser Arg Val Ile Thr Gly Asn Leu Met Met Pro Gly Phe Thr
                115                 120                 125

Ala Pro Lys Leu Leu Trp Val Gln Arg His Glu Pro Glu Ile Phe Arg
            130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
            195                 200                 205

Thr Gly Ala Leu Leu Pro Glu Val Ala Lys Ala Trp Gly Met Ala Thr
        210                 215                 220

Val Pro Val Val Ala Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
            275                 280                 285

Ser Val Met Leu Ser Ala Ala Ser Cys Leu Asp Trp Ala Ala Lys Leu
        290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
        355                 360                 365

Val Gly Tyr Ala Leu Ala Asp Gly Met Asp Val His Ala Cys Gly
    370                 375                 380

Ile Lys Pro Gln Ser Val Thr Leu Ile Gly Gly Ala Arg Ser Glu
385                 390                 395                 400

Tyr Trp Arg Gln Met Leu Ala Asp Ile Ser Gly Gln Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
        435                 440                 445
```

```
Leu Pro Leu Glu Gln Ser His Leu Pro Asp Ala Gln Arg Tyr Ala Ala
    450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 6
<211> LENGTH: 491
<212> TYPE: PRT
<213> ORGANISM: Escherichia coli

<400> SEQUENCE: 6

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln Asn Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Tyr Cys Ser Asn
65                  70                  75                  80

Arg Phe Gly Arg Arg Asp Ser Leu Lys Ile Ala Ala Val Leu Phe Phe
                85                  90                  95

Ile Ser Gly Val Gly Ser Ala Trp Pro Glu Leu Gly Phe Thr Ser Ile
            100                 105                 110

Asn Pro Asp Asn Thr Val Pro Val Tyr Leu Ala Gly Tyr Val Pro Glu
        115                 120                 125

Phe Val Ile Tyr Arg Ile Ile Gly Gly Ile Gly Val Gly Leu Ala Ser
    130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
            180                 185                 190

Trp Leu Asn Thr Asp Gly Trp Arg Tyr Met Phe Ala Ser Glu Cys Ile
        195                 200                 205

Pro Ala Leu Leu Phe Leu Met Leu Leu Tyr Thr Val Pro Glu Ser Pro
    210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
            260                 265                 270

Phe Gly Val Gly Val Ile Val Ile Gly Val Met Leu Ser Ile Phe Gln
        275                 280                 285

Gln Phe Val Gly Ile Asn Val Val Leu Tyr Tyr Ala Pro Glu Val Phe
    290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335
```

```
Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Pro
            355                 360                 365

Gly Ile Val Ala Leu Leu Ser Met Leu Phe Tyr Val Ala Ala Phe Ala
        370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
            420                 425                 430

Ser Trp Leu Val Ala His Phe His Asn Gly Phe Ser Tyr Trp Ile Tyr
        435                 440                 445

Gly Cys Met Gly Val Leu Ala Ala Leu Phe Met Trp Lys Phe Val Pro
    450                 455                 460

Glu Thr Lys Gly Lys Thr Leu Glu Glu Leu Glu Ala Leu Trp Glu Pro
465                 470                 475                 480

Glu Thr Lys Lys Thr Gln Gln Thr Ala Thr Leu
                485                 490

<210> SEQ ID NO 7
<211> LENGTH: 330
<212> TYPE: PRT
<213> ORGANISM: Escherichia coli

<400> SEQUENCE: 7

Met Lys Ile Lys Asn Ile Leu Leu Thr Leu Cys Thr Ser Leu Leu Leu
1               5                   10                  15

Thr Asn Val Ala Ala His Ala Lys Glu Val Lys Ile Gly Met Ala Ile
            20                  25                  30

Asp Asp Leu Arg Leu Glu Arg Trp Gln Lys Asp Arg Asp Ile Phe Val
        35                  40                  45

Lys Lys Ala Glu Ser Leu Gly Ala Lys Val Phe Val Gln Ser Ala Asn
    50                  55                  60

Gly Asn Glu Glu Thr Gln Met Ser Gln Ile Glu Asn Met Ile Asn Arg
65                  70                  75                  80

Gly Val Asp Val Leu Val Ile Ile Pro Tyr Asn Gly Gln Val Leu Ser
                85                  90                  95

Asn Val Val Lys Glu Ala Lys Gln Glu Gly Ile Lys Val Leu Ala Tyr
            100                 105                 110

Asp Arg Met Ile Asn Asp Ala Asp Ile Asp Phe Tyr Ile Ser Phe Asp
        115                 120                 125

Asn Glu Lys Val Gly Glu Leu Gln Ala Lys Ala Leu Val Asp Ile Val
    130                 135                 140

Pro Gln Gly Asn Tyr Phe Leu Met Gly Gly Ser Pro Val Asp Asn Asn
145                 150                 155                 160

Ala Lys Leu Phe Arg Ala Gly Gln Met Lys Val Leu Lys Pro Tyr Val
                165                 170                 175

Asp Ser Gly Lys Ile Lys Val Val Gly Asp Gln Trp Val Asp Gly Trp
            180                 185                 190

Leu Pro Glu Asn Ala Leu Lys Ile Met Glu Asn Ala Leu Thr Ala Asn
        195                 200                 205

Asn Asn Lys Ile Asp Ala Val Val Ala Ser Asn Asp Ala Thr Ala Gly
```

```
                210                 215                 220
Gly Ala Ile Gln Ala Leu Ser Ala Gln Gly Leu Ser Gly Lys Val Ala
225                 230                 235                 240

Ile Ser Gly Gln Asp Ala Asp Leu Ala Gly Ile Lys Arg Ile Ala Ala
                245                 250                 255

Gly Thr Gln Thr Met Thr Val Tyr Lys Pro Ile Thr Leu Leu Ala Asn
                260                 265                 270

Thr Ala Ala Glu Ile Ala Val Glu Leu Gly Asn Gly Gln Glu Pro Lys
            275                 280                 285

Ala Asp Thr Thr Leu Asn Asn Gly Leu Lys Asp Val Pro Ser Arg Leu
        290                 295                 300

Leu Thr Pro Ile Asp Val Asn Lys Asn Asn Ile Lys Asp Thr Val Ile
305                 310                 315                 320

Lys Asp Gly Phe His Lys Glu Ser Glu Leu
                325                 330

<210> SEQ ID NO 8
<211> LENGTH: 513
<212> TYPE: PRT
<213> ORGANISM: Escherichia coli

<400> SEQUENCE: 8

Met Pro Tyr Leu Leu Glu Met Lys Asn Ile Thr Lys Thr Phe Gly Ser
1               5                   10                  15

Val Lys Ala Ile Asp Asn Val Cys Leu Arg Leu Asn Ala Gly Glu Ile
            20                  25                  30

Val Ser Leu Cys Gly Glu Asn Gly Ser Gly Lys Ser Thr Leu Met Lys
        35                  40                  45

Val Leu Cys Gly Ile Tyr Pro His Gly Ser Tyr Glu Gly Glu Ile Ile
    50                  55                  60

Phe Ala Gly Glu Glu Ile Gln Ala Ser His Ile Arg Asp Thr Glu Arg
65                  70                  75                  80

Lys Gly Ile Ala Ile Ile His Gln Glu Leu Ala Leu Val Lys Glu Leu
                85                  90                  95

Thr Val Leu Glu Asn Ile Phe Leu Gly Asn Glu Ile Thr His Asn Gly
            100                 105                 110

Ile Met Asp Tyr Asp Leu Met Thr Leu Arg Cys Gln Lys Leu Leu Ala
        115                 120                 125

Gln Val Ser Leu Ser Ile Ser Pro Asp Thr Arg Val Gly Asp Leu Gly
    130                 135                 140

Leu Gly Gln Gln Gln Leu Val Glu Ile Ala Lys Ala Leu Asn Lys Gln
145                 150                 155                 160

Val Arg Leu Leu Ile Leu Asp Glu Pro Thr Ala Ser Leu Thr Glu Gln
                165                 170                 175

Glu Thr Ser Ile Leu Leu Asp Ile Ile Arg Asp Leu Gln Gln His Gly
            180                 185                 190

Ile Ala Cys Ile Tyr Ile Ser His Lys Leu Asn Glu Val Lys Ala Ile
        195                 200                 205

Ser Asp Thr Ile Cys Val Ile Arg Asp Gly Gln His Ile Gly Thr Arg
    210                 215                 220

Asp Ala Ala Gly Met Ser Glu Asp Asp Ile Ile Thr Met Met Val Gly
225                 230                 235                 240

Arg Glu Leu Thr Ala Leu Tyr Pro Asn Glu Pro His Thr Thr Gly Asp
                245                 250                 255
```

Glu Ile Leu Arg Ile Glu His Leu Thr Ala Trp His Pro Val Asn Arg
    260                 265                 270

His Ile Lys Arg Val Asn Asp Val Ser Phe Ser Leu Lys Arg Gly Glu
            275                 280                 285

Ile Leu Gly Ile Ala Gly Leu Val Gly Ala Gly Arg Thr Glu Thr Ile
        290                 295                 300

Gln Cys Leu Phe Gly Val Trp Pro Gly Gln Trp Glu Gly Lys Ile Tyr
305                 310                 315                 320

Ile Asp Gly Lys Gln Val Asp Ile Arg Asn Cys Gln Gln Ala Ile Ala
                325                 330                 335

Gln Gly Ile Ala Met Val Pro Glu Asp Arg Lys Arg Asp Gly Ile Val
            340                 345                 350

Pro Val Met Ala Val Gly Lys Asn Ile Thr Leu Ala Ala Leu Asn Lys
        355                 360                 365

Phe Thr Gly Gly Ile Ser Gln Leu Asp Asp Ala Ala Glu Gln Lys Cys
370                 375                 380

Ile Leu Glu Ser Ile Gln Gln Leu Lys Val Lys Thr Ser Ser Pro Asp
385                 390                 395                 400

Leu Ala Ile Gly Arg Leu Ser Gly Gly Asn Gln Gln Lys Ala Ile Leu
                405                 410                 415

Ala Arg Cys Leu Leu Leu Asn Pro Arg Ile Leu Ile Leu Asp Glu Pro
            420                 425                 430

Thr Arg Gly Ile Asp Ile Gly Ala Lys Tyr Glu Ile Tyr Lys Leu Ile
        435                 440                 445

Asn Gln Leu Val Gln Gln Gly Ile Ala Val Ile Val Ile Ser Ser Glu
450                 455                 460

Leu Pro Glu Val Leu Gly Leu Ser Asp Arg Val Leu Val Met His Glu
465                 470                 475                 480

Gly Lys Leu Lys Ala Asn Leu Ile Asn His Asn Leu Thr Gln Glu Gln
                485                 490                 495

Val Met Glu Ala Ala Leu Arg Ser Glu His His Val Glu Lys Gln Ser
            500                 505                 510

Val

<210> SEQ ID NO 9
<211> LENGTH: 393
<212> TYPE: PRT
<213> ORGANISM: Escherichia coli

<400> SEQUENCE: 9

Met Ser Lys Ser Asn Pro Ser Glu Val Lys Leu Ala Val Pro Thr Ser
1               5                   10                  15

Gly Gly Phe Ser Gly Leu Lys Ser Leu Asn Leu Gln Val Phe Val Met
            20                  25                  30

Ile Ala Ala Ile Ile Ala Ile Met Leu Phe Phe Thr Trp Thr Thr Asp
        35                  40                  45

Gly Ala Tyr Leu Ser Ala Arg Asn Val Ser Asn Leu Leu Arg Gln Thr
    50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Cys Asp Val Trp Leu Gly Trp Pro Leu Pro Leu Thr
            100                 105                 110

-continued

Ile Ile Val Thr Leu Val Leu Gly Leu Leu Gly Ala Trp Asn Gly
        115                 120                 125

Trp Trp Val Ala Tyr Arg Lys Val Pro Ser Phe Ile Val Thr Leu Ala
130                 135                 140

Gly Met Leu Ala Phe Arg Gly Ile Leu Ile Gly Ile Thr Asn Gly Thr
145                 150                 155                 160

Thr Val Ser Pro Thr Ser Ala Ala Met Ser Gln Ile Gly Gln Ser Tyr
                165                 170                 175

Leu Pro Ala Ser Thr Gly Phe Ile Ile Gly Ala Leu Gly Leu Met Ala
                180                 185                 190

Phe Val Gly Trp Gln Trp Arg Gly Arg Met Arg Arg Gln Ala Leu Gly
            195                 200                 205

Leu Gln Ser Pro Ala Ser Thr Ala Val Val Gly Arg Gln Ala Leu Thr
210                 215                 220

Ala Ile Ile Val Leu Gly Ala Ile Trp Leu Leu Asn Asp Tyr Arg Gly
225                 230                 235                 240

Val Pro Thr Pro Val Leu Leu Leu Thr Leu Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285

Lys Leu Ala Val Phe Ala Ile Asn Gly Leu Met Val Ala Ile Ala Gly
        290                 295                 300

Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335

Leu Ala Gly Gly Val Gly Ser Val Ala Gly Ala Val Met Gly Ala Phe
                340                 345                 350

Ile Met Ala Ser Leu Asp Asn Gly Met Ser Met Met Asp Val Pro Thr
            355                 360                 365

Phe Trp Gln Tyr Ile Val Lys Gly Ala Ile Leu Leu Leu Ala Val Trp
370                 375                 380

Met Asp Ser Ala Thr Lys Arg Arg Ser
385                 390

<210> SEQ ID NO 10
<211> LENGTH: 317
<212> TYPE: PRT
<213> ORGANISM: Escherichia coli

<400> SEQUENCE: 10

Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
            115                 120                 125

Ile Leu Ile Lys Leu Ala Ser Thr Trp Gln Gly Ile Arg Ala Ala Glu
130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
            195                 200                 205

Ile Tyr Gln Tyr Tyr Lys Glu His Gly Tyr Glu Thr Val Val Met Gly
            210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
            275                 280                 285

Pro Met Ala Val Asp Lys Leu Ala Glu Gly Ile Arg Lys Phe Ala Ile
            290                 295                 300

Asp Gln Glu Lys Leu Glu Lys Met Ile Gly Asp Leu Leu
305                 310                 315

<210> SEQ ID NO 11
<211> LENGTH: 663
<212> TYPE: PRT
<213> ORGANISM: Escherichia coli

<400> SEQUENCE: 11

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
        130                 135                 140

Val Asp His Tyr Thr Tyr Ala Phe Met Gly Asp Gly Cys Met Met Glu

```
            145                 150                 155                 160
        Gly Ile Ser His Glu Val Cys Ser Leu Ala Gly Thr Leu Lys Leu Gly
                        165                 170                 175
        Lys Leu Ile Ala Phe Tyr Asp Asp Asn Gly Ile Ser Ile Asp Gly His
                        180                 185                 190
        Val Glu Gly Trp Phe Thr Asp Thr Ala Met Arg Phe Glu Ala Tyr
                        195                 200                 205
        Gly Trp His Val Ile Arg Asp Ile Asp Gly His Asp Ala Ala Ser Ile
                        210                 215                 220
        Lys Arg Ala Val Glu Glu Ala Arg Ala Val Thr Asp Lys Pro Ser Leu
        225                 230                 235                 240
        Leu Met Cys Lys Thr Ile Ile Gly Phe Gly Ser Pro Asn Lys Ala Gly
                        245                 250                 255
        Thr His Asp Ser His Gly Ala Pro Leu Gly Asp Ala Glu Ile Ala Leu
                        260                 265                 270
        Thr Arg Glu Gln Leu Gly Trp Lys Tyr Ala Pro Phe Glu Ile Pro Ser
                        275                 280                 285
        Glu Ile Tyr Ala Gln Trp Asp Ala Lys Glu Ala Gly Gln Ala Lys Glu
                        290                 295                 300
        Ser Ala Trp Asn Glu Lys Phe Ala Ala Tyr Ala Lys Ala Tyr Pro Gln
        305                 310                 315                 320
        Glu Ala Ala Glu Phe Thr Arg Arg Met Lys Gly Glu Met Pro Ser Asp
                        325                 330                 335
        Phe Asp Ala Lys Ala Lys Glu Phe Ile Ala Lys Leu Gln Ala Asn Pro
                        340                 345                 350
        Ala Lys Ile Ala Ser Arg Lys Ala Ser Gln Asn Ala Ile Glu Ala Phe
                        355                 360                 365
        Gly Pro Leu Leu Pro Glu Phe Leu Gly Gly Ser Ala Asp Leu Ala Pro
                        370                 375                 380
        Ser Asn Leu Thr Leu Trp Ser Gly Ser Lys Ala Ile Asn Glu Asp Ala
        385                 390                 395                 400
        Ala Gly Asn Tyr Ile His Tyr Gly Val Arg Glu Phe Gly Met Thr Ala
                        405                 410                 415
        Ile Ala Asn Gly Ile Ser Leu His Gly Gly Phe Leu Pro Tyr Thr Ser
                        420                 425                 430
        Thr Phe Leu Met Phe Val Glu Tyr Ala Arg Asn Ala Val Arg Met Ala
                        435                 440                 445
        Ala Leu Met Lys Gln Arg Gln Val Met Val Tyr Thr His Asp Ser Ile
        450                 455                 460
        Gly Leu Gly Glu Asp Gly Pro Thr His Gln Pro Val Glu Gln Val Ala
        465                 470                 475                 480
        Ser Leu Arg Val Thr Pro Asn Met Ser Thr Trp Arg Pro Cys Asp Gln
                        485                 490                 495
        Val Glu Ser Ala Val Ala Trp Lys Tyr Gly Val Glu Arg Gln Asp Gly
                        500                 505                 510
        Pro Thr Ala Leu Ile Leu Ser Arg Gln Asn Leu Ala Gln Gln Glu Arg
                        515                 520                 525
        Thr Glu Glu Gln Leu Ala Asn Ile Ala Arg Gly Gly Tyr Val Leu Lys
                        530                 535                 540
        Asp Cys Ala Gly Gln Pro Glu Leu Ile Phe Ile Ala Thr Gly Ser Glu
        545                 550                 555                 560
        Val Glu Leu Ala Val Ala Ala Tyr Glu Lys Leu Thr Ala Glu Gly Val
                        565                 570                 575
```

```
Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
            610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Glu Leu Leu
            660

<210> SEQ ID NO 12
<211> LENGTH: 321
<212> TYPE: PRT
<213> ORGANISM: Escherichia coli

<400> SEQUENCE: 12

Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
    210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
            260                 265                 270

Lys Ala Ser Gly Phe Arg Ala Ala Phe Glu Asp Lys Gly Arg Phe Lys
```

```
            275                 280                 285
Glu Tyr Val His Asp Ile Pro Val Tyr Leu Ile Val His Asp Asn Pro
    290                 295                 300
Gly Leu Leu Gly Ser Gly Ala His Leu Arg Gln Thr Leu Gly His Ile
305                 310                 315                 320
Leu
```

<210> SEQ ID NO 13
<211> LENGTH: 391
<212> TYPE: PRT
<213> ORGANISM: Escherichia albertii

<400> SEQUENCE: 13

```
Met Gln Lys Leu Ile Asn Ser Val Gln Asn Tyr Ala Trp Gly Ser Lys
1               5                   10                  15
Thr Ala Leu Thr Glu Leu Tyr Gly Met Glu Asn Pro Ser Asn Gln Pro
                20                  25                  30
Met Ala Glu Leu Trp Met Gly Ala His Pro Lys Ser Ser Arg Val
        35                  40                  45
His Asn Ala Ala Gly Glu Val Val Ser Leu Arg Asp Val Ile Glu Ser
    50                  55                  60
Asn Lys Ser Thr Leu Leu Gly Glu Ala Val Ala Gln Arg Phe Gly Glu
65                  70                  75                  80
Leu Pro Phe Leu Phe Lys Val Leu Cys Ala Ala Gln Pro Leu Ser Ile
                85                  90                  95
Gln Val His Pro Asn Lys Arg Asn Ser Glu Ile Gly Phe Ala Lys Glu
                100                 105                 110
Asn Ala Ala Gly Ile Pro Met Asp Ala Ala Glu Arg Asn Tyr Lys Asp
            115                 120                 125
Pro Asn His Lys Pro Glu Leu Val Phe Ala Leu Thr Pro Phe Leu Ala
130                 135                 140
Met Asn Ala Phe Arg Glu Phe Ser Glu Ile Val Ser Leu Leu Gln Pro
145                 150                 155                 160
Val Ala Asp Ala His Pro Ala Ile Thr His Phe Leu Gln Gln Pro Asn
                165                 170                 175
Ala Glu Arg Leu Ser Glu Leu Phe Ala Ser Leu Leu Asn Met Gln Gly
            180                 185                 190
Glu Glu Lys Ser Arg Ala Leu Ala Ile Leu Lys Ser Ala Leu His Ser
        195                 200                 205
Gln Gln Gly Glu Pro Trp Gln Thr Ile Arg Leu Ile Ser Glu Phe Tyr
    210                 215                 220
Pro Asp Asp Ser Gly Leu Phe Ser Pro Leu Leu Leu Asn Val Val Lys
225                 230                 235                 240
Leu Asn Pro Gly Glu Ala Met Phe Leu Phe Ala Glu Thr Pro His Ala
                245                 250                 255
Tyr Leu Gln Gly Val Ala Leu Glu Val Met Ala Asn Ser Asp Asn Val
            260                 265                 270
Leu Arg Ala Gly Leu Thr Pro Lys Tyr Ile Asp Ile Pro Glu Leu Val
        275                 280                 285
Ala Asn Val Lys Phe Glu Lys Pro Ala Asn Gln Leu Leu Thr Gln
    290                 295                 300
Pro Val Lys His Gly Ala Glu Leu Asp Phe Pro Ile Pro Val Asp Asp
305                 310                 315                 320
Phe Ala Phe Ser Leu His Asp Leu Asn Asp Lys Glu Cys Thr Ile Gly
```

325                 330                 335
Gln Gln Ser Ala Ala Ile Leu Phe Cys Val Glu Gly Glu Ala Thr Leu
                340                 345                 350

Asn Lys Asp Ser Gln Gln Leu Leu Lys Pro Gly Glu Ser Ala Phe
            355                 360                 365

Ile Ala Ala Asn Glu Ser Pro Val Lys Val Lys Gly His Gly Arg Leu
370                 375                 380

Ala Arg Val Tyr Asn Lys Leu
385                 390

<210> SEQ ID NO 14
<211> LENGTH: 302
<212> TYPE: PRT
<213> ORGANISM: Escherichia blattae

<400> SEQUENCE: 14

Met Arg Ile Gly Ile Asp Leu Gly Gly Thr Lys Thr Glu Val Ile Ala
1               5                   10                  15

Leu Gly Asp Ala Gly Glu Gln Leu Tyr Arg His Arg Leu Pro Thr Pro
                20                  25                  30

Arg Asp Asp Tyr Arg Gln Thr Ile Glu Thr Ile Ala Thr Leu Val Asp
            35                  40                  45

Met Ala Glu Gln Thr Thr Gly Gln Cys Gly Thr Val Gly Ile Gly Ile
50                  55                  60

Pro Gly Ser Ile Ser Pro Tyr Thr Gly Val Val Lys Asn Ala Asn Ser
65                  70                  75                  80

Thr Trp Leu Asn Gly Gln Pro Phe Asp Lys Asp Leu Ser Ala Arg Leu
                85                  90                  95

Gln Arg Glu Val Arg Leu Ala Asn Asp Ala Asn Cys Leu Ala Val Ser
            100                 105                 110

Glu Ala Val Asp Gly Ala Ala Gly Ala Lys Thr Val Phe Ala Val
            115                 120                 125

Ile Ile Gly Thr Gly Cys Gly Ala Gly Val Ala Phe Asn Gly Arg Ala
130                 135                 140

His Ile Gly Gly Asn Gly Thr Ala Gly Glu Trp Gly His Asn Pro Leu
145                 150                 155                 160

Pro Trp Met Asp Thr Asp Glu Leu Arg Tyr Arg Glu Glu Val Pro Cys
                165                 170                 175

Tyr Cys Gly Lys Gln Gly Cys Ile Glu Thr Phe Ile Ser Gly Thr Gly
            180                 185                 190

Phe Ala Thr Asp Tyr His Arg Leu Ser Gly His Val Leu Lys Gly Ser
        195                 200                 205

Glu Ile Ile Arg Leu Val Glu Glu Asn Asp Pro Val Ala Glu Leu Ala
    210                 215                 220

Leu Asp Arg Tyr Glu Arg Arg Leu Ala Lys Ser Leu Ala His Val Val
225                 230                 235                 240

Asn Ile Leu Asp Pro Asp Val Ile Val Leu Gly Gly Met Ser Asn
                245                 250                 255

Val Glu Arg Leu Tyr Gln Thr Val Pro Pro Leu Ile Lys Arg Phe Val
            260                 265                 270

Phe Gly Gly Glu Cys Glu Thr Pro Val Arg Lys Ala Lys His Gly Asp
        275                 280                 285

Ser Ser Gly Val Arg Gly Ala Ala Trp Leu Trp Pro Gln Glu
    290                 295                 300

<210> SEQ ID NO 15
<211> LENGTH: 411
<212> TYPE: PRT
<213> ORGANISM: Escherichia fergusonii

<400> SEQUENCE: 15

```
Met Pro Glu Asn Ser Cys Phe Asn Asn Ala Asn Lys Leu His Met Lys
1               5                   10                  15

Gln Gly Leu Ile Met Gln Lys Leu Ile Asn Ser Val Gln Asn Tyr Ala
            20                  25                  30

Trp Gly Ser Lys Thr Ala Leu Thr Asp Leu Tyr Gly Ile Ala Asn Pro
        35                  40                  45

Ser Gln Gln Pro Met Ala Glu Leu Trp Met Gly Ala His Pro Lys Ser
    50                  55                  60

Ser Ser Lys Val Glu Thr Ser Glu Gly Gln Ile Val Ser Leu Arg Asp
65                  70                  75                  80

Val Ile Glu Asn Asp Lys Ser Ala Leu Leu Gly Asp Ala Val Ala Glu
                85                  90                  95

Arg Phe Gly Glu Leu Pro Phe Leu Phe Lys Val Leu Cys Ala Ala Gln
            100                 105                 110

Pro Leu Ser Ile Gln Val His Pro Asn Lys Arg Asn Ser Glu Ile Gly
        115                 120                 125

Phe Ala Lys Glu Asn Ala Ala Gly Ile Pro Met Asp Ala Ala Glu Arg
    130                 135                 140

Asn Tyr Lys Asp Pro Asn His Lys Pro Glu Leu Val Phe Ala Leu Thr
145                 150                 155                 160

Pro Phe Leu Ala Met Asn Ala Phe Arg Glu Phe Ser Glu Ile Val Ser
                165                 170                 175

Leu Leu Gln Pro Val Ala Gly Ala His Pro Ala Ile Ala His Phe Leu
            180                 185                 190

Gln Gln Pro Asp Ala Glu Arg Leu Ser Glu Leu Phe Ala Ala Leu Leu
        195                 200                 205

Asn Met Gln Gly Glu Glu Lys Ser Arg Ala Leu Ala Ile Leu Lys Ser
    210                 215                 220

Ala Leu Asp Thr Gln Gln Gly Glu Pro Trp Gln Thr Ile Arg Val Ile
225                 230                 235                 240

Ala Gln Phe Tyr Pro Asp Asp Ser Gly Leu Phe Ser Pro Leu Leu Leu
                245                 250                 255

Asn Val Val Lys Leu Asn Pro Gly Glu Ala Met Phe Leu Phe Ala Glu
            260                 265                 270

Thr Pro His Ala Tyr Leu Gln Gly Val Ala Leu Glu Val Met Ala Asn
        275                 280                 285

Ser Asp Asn Val Leu Arg Ala Gly Leu Thr Pro Lys Tyr Ile Asp Ile
    290                 295                 300

Pro Glu Leu Val Ala Asn Val Lys Phe Glu Ala Lys Pro Ala Gly Gln
305                 310                 315                 320

Leu Leu Thr Gln Pro Ile Lys Asn Gly His Glu Leu Asp Phe Pro Ile
                325                 330                 335

Pro Val Glu Asp Phe Ala Phe Ala Leu His Asp Leu Thr Lys Asp Glu
            340                 345                 350

Ala Ala Val Asn Gln Gln Ser Ala Ala Ile Leu Phe Cys Val Glu Gly
        355                 360                 365

Glu Ala Cys Leu Arg Lys Gly Asp Gln Gln Leu His Leu Lys Pro Gly
    370                 375                 380
```

```
Glu Ser Ala Phe Ile Ala Ala Asn Glu Ser Pro Val Leu Val Ser Gly
385                 390                 395                 400

Asn Gly Arg Leu Ala Arg Val Tyr Asn Lys Leu
                405                 410

<210> SEQ ID NO 16
<211> LENGTH: 440
<212> TYPE: PRT
<213> ORGANISM: Escherichia fergusonii

<400> SEQUENCE: 16

Met Gln Ala Tyr Phe Asp Gln Leu Asp Arg Val Arg Tyr Glu Gly Pro
1               5                   10                  15

Lys Thr Thr Asn Pro Leu Ala Phe Arg His Tyr Asn Pro Asp Glu Leu
                20                  25                  30

Val Leu Gly Lys Arg Met Glu Asp His Leu Arg Phe Ala Ala Cys Tyr
            35                  40                  45

Trp His Thr Phe Cys Trp Asn Gly Ala Asp Met Phe Gly Val Gly Ala
        50                  55                  60

Phe Asp Arg Pro Trp Gln Gln Pro Gly Glu Ala Leu Met Leu Ala Lys
65                  70                  75                  80

Arg Lys Ala Asp Val Ala Phe Glu Phe Phe His Lys Leu Asn Val Pro
                85                  90                  95

Phe Tyr Cys Phe His Asp Val Asp Val Ser Pro Glu Gly Ala Ser Leu
                100                 105                 110

Lys Glu Tyr Lys Asn Asn Phe Ala Glu Met Val Asp Val Leu Ala Ala
            115                 120                 125

Lys Gln Glu Gln Ser Gly Val Lys Leu Leu Trp Gly Thr Ala Asn Cys
        130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr Lys Arg Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
```

```
            340                 345                 350
Phe Tyr Gly His Ile Gly Ala Met Asp Thr Met Ala Leu Ala Leu Lys
            355                 360                 365

Val Ala Ala Arg Met Ile Glu Asp Gly Glu Leu Asp Lys Arg Val Ala
370                 375                 380

Gln Arg Tyr Ser Gly Trp Asn Ser Glu Leu Gly Gln Gln Ile Leu Lys
385                 390                 395                 400

Gly Gln Met Ser Leu Ser Asp Leu Ala Lys Tyr Ala Gln Asp His Asn
                405                 410                 415

Leu Ser Pro Val His Gln Ser Gly His Gln Glu Leu Leu Glu Ser Leu
            420                 425                 430

Val Asn His Tyr Leu Phe Asp Lys
            435                 440

<210> SEQ ID NO 17
<211> LENGTH: 391
<212> TYPE: PRT
<213> ORGANISM: Shigella flexneri

<400> SEQUENCE: 17

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
                20                  25                  30

Met Ala Glu Leu Trp Met Gly Ala His Pro Lys Ser Ser Ser Arg Val
            35                  40                  45

Gln Asn Ala Ala Gly Asp Ile Val Ser Leu Arg Asp Val Ile Glu Ser
50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
            115                 120                 125

Pro Asn His Lys Pro Glu Leu Val Phe Ala Leu Thr Pro Phe Leu Ala
130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro His
                165                 170                 175

Ala Glu Arg Leu Ser Glu Leu Phe Ala Asn Leu Leu Asn Met Gln Gly
            180                 185                 190

Glu Glu Lys Ser Arg Ala Leu Ala Ile Leu Lys Ser Ala Leu Asp Ser
            195                 200                 205

Gln Gln Gly Glu Pro Trp Gln Thr Ile Arg Leu Ile Ser Glu Phe Tyr
        210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270
```

Leu Arg Ala Gly Leu Thr Pro Lys Tyr Ile Asp Ile Pro Glu Leu Val
            275                 280                 285

Ala Asn Val Lys Phe Glu Ala Lys Pro Ala Asn Gln Leu Leu Thr Gln
290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
                340                 345                 350

Trp Lys Gly Ser Gln Gln Leu Gln Leu Lys Pro Gly Glu Ser Ala Phe
            355                 360                 365

Ile Ala Ala Asn Glu Ser Pro Val Thr Val Lys Gly His Gly Arg Leu
370                 375                 380

Ala Arg Val Tyr Asn Lys Leu
385                 390

<210> SEQ ID NO 18
<211> LENGTH: 391
<212> TYPE: PRT
<213> ORGANISM: Shigella sonnei

<400> SEQUENCE: 18

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys Arg Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asn
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
    210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

```
Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Asn Gln Leu Leu Thr Gln
    290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
        355                 360                 365

Ile Ala Ala Asn Glu Ser Pro Val Thr Val Lys Gly His Gly Arg Leu
    370                 375                 380

Ala Arg Val Tyr Asn Lys Leu
385                 390

<210> SEQ ID NO 19
<211> LENGTH: 440
<212> TYPE: PRT
<213> ORGANISM: Shigella sonnei

<400> SEQUENCE: 19

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Ala
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
```

```
            225                 230                 235                 240
His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His Glu Ile Ala Thr Ala Ile Ala
        275                 280                 285

Leu Gly Leu Phe Gly Ser Val Asp Ala Asn Arg Gly Asp Ala Gln Leu
        290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
    370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His Asn
                405                 410                 415

Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 20
<211> LENGTH: 391
<212> TYPE: PRT
<213> ORGANISM: Shigella dysenteriae

<400> SEQUENCE: 20

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45

Gln Asn Ala Ala Gly Asp

```
Val Ala Gly Ala His Pro Ala Ile Ala His Phe Leu Gln Gln Pro His
165 170 175

Ala Glu His Leu Ser Glu Leu Phe Ala Ser Leu Leu Asn Met Gln Gly
180 185 190

Glu Glu Lys Ser Arg Ala Leu Ala Ile Leu Lys Ser Thr Leu Asp Ser
195 200 205

Gln Gln Gly Glu Pro Trp Gln Thr Ile Arg Leu Ile Ser Glu Phe Tyr
210 215 220

Pro Glu Asp Ser Gly Leu Phe Ser Pro Leu Leu Leu Asn Val Val Lys
225 230 235 240

Leu Asn Pro Gly Glu Ala Met Phe Leu Phe Ala Glu Thr Pro His Ala
245 250 255

Tyr Leu Gln Gly Val Ala Leu Glu Val Met Ala Asn Ser Asp Asn Val
260 265 270

Leu Arg Ala Gly Leu Thr Pro Lys Tyr Ile Asp Ile Pro Glu Leu Val
275 280 285

Ala Asn Val Lys Phe Glu Ala Lys Pro Ala Asn Gln Leu Leu Thr Gln
290 295 300

Pro Val Lys Gln Gly Ala Glu Leu Asp Phe Pro Ile Pro Val Asp Asp
305 310 315 320

Phe Ala Phe Ser Leu His Asp Leu Ser Asp Lys Glu Thr Thr Ile Ser
325 330 335

Gln Gln Ser Ala Ala Ile Leu Phe Cys Val Glu Gly Asp Ala Thr Leu
340 345 350

Trp Lys Gly Ser Gln Gln Leu Gln Leu Lys Pro Gly Glu Ser Ala Phe
355 360 365

Ile Ala Ala Asn Glu Ser Pro Val Thr Val Lys Gly His Gly Arg Leu
370 375 380

Ala Arg Val Tyr Asn Lys Leu
385 390

<210> SEQ ID NO 21
<211> LENGTH: 300
<212> TYPE: PRT
<213> ORGANISM: Shigella dysenteriae

<400> SEQUENCE: 21

Met Arg Ile Gly Ile Asp Leu Gly Gly Thr Lys Thr Glu Val Ile Ala
1 5 10 15

Leu Gly Asp Ala Gly Glu Gln Leu Tyr Arg His Arg Leu Pro Thr Pro
20 25 30

Arg Asp Asp Tyr Arg Gln Thr Ile Glu Thr Ile Ala Thr Leu Val Asp
35 40 45

Met Ala Glu Gln Ala Thr Gly Gln Arg Gly Thr Val Gly Met Gly Ile
50 55 60

Pro Gly Ala Ile Ser Pro Tyr Thr Gly Val Val Lys Asn Ala Asn Ser
65 70 75 80

Thr Trp Leu Asn Gly Gln Pro Phe Asp Lys Asp Leu Ser Ala Arg Leu
85 90 95

Gln Arg Glu Val Arg Leu Ala Asn Asp Ala Asn Cys Leu Ala Val Ser
100 105 110

Glu Ala Val Asp Gly Ala Ala Ala Gly Ala Gln Thr Val Phe Ala Val
115 120 125

Ile Ile Gly Thr Gly Cys Gly Ala Gly Val Ala Phe Asn Gly Arg Ala
130 135 140

```
His Ile Gly Gly Asn Gly Thr Ala Gly Glu Trp Gly His Asn Pro Leu
145                 150                 155                 160

Pro Trp Met Asp Glu Asp Glu Leu Arg Tyr Arg Glu Val Pro Cys
            165                 170                 175

Tyr Cys Gly Lys Gln Gly Cys Ile Glu Thr Phe Ile Ser Gly Thr Gly
            180                 185                 190

Phe Ala Thr Asp Tyr Arg Arg Leu Ser Gly His Ala Leu Lys Gly Ser
            195                 200                 205

Glu Ile Ile Ser Leu Val Glu Glu Ser Asp Pro Val Ala Glu Leu Ala
            210                 215                 220

Leu Arg Arg Tyr Glu Leu Arg Leu Ala Lys Ser Leu Ala His Val Val
225                 230                 235                 240

Asn Ile Leu Asp Pro Asp Val Ile Val Leu Gly Gly Met Ser Asn
            245                 250                 255

Val Asp Arg Leu Tyr Gln Thr Val Pro Gln Leu Ile Lys Gln Phe Val
            260                 265                 270

Phe Gly Gly Glu Cys Glu Thr Pro Val Arg Lys Ala Lys His Gly Asp
            275                 280                 285

Ser Ser Gly Val Arg Gly Ala Ala Trp Leu Trp Pro
            290                 295                 300

<210> SEQ ID NO 22
<211> LENGTH: 440
<212> TYPE: PRT
<213> ORGANISM: Shigella dysenteriae

<400> SEQUENCE: 22

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
            35                  40                  45

Trp His Thr Phe Cys Trp Asn Gly Ala Asp Met Phe Gly Val Gly Ala
            50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
            85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
            115                 120                 125

Lys Gln Glu Glu Ser Gly Val Lys Leu Leu Trp Gly Thr Ala Asn Cys
            130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
            165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
            195                 200                 205

Leu Gly Arg Phe Met Gln Met Val Val Glu His Lys His Lys Ile Gly
```

```
              210                 215                 220
Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His Glu Ile Ala Thr Ala Ile Ala
            275                 280                 285

Leu Gly Leu Phe Gly Ser Val Asp Ala Asn Arg Gly Asp Ala Gln Leu
        290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Cys Met Ile Glu Asp Gly Glu Leu Asp Lys Arg Ile Ala
370                 375                 380

Gln Arg Tyr Ser Gly Trp Asn Ser Glu Leu Gly Gln His Ile Leu Lys
385                 390                 395                 400

Gly Gln Met Ser Leu Ala Asp Leu Ala Lys Tyr Ala Gln Glu His Asn
                405                 410                 415

Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 23
<211> LENGTH: 350
<212> TYPE: PRT
<213> ORGANISM: Citrobacter koseri

<400> SEQUENCE: 23

Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Ser Gln Gln Pro
            20                  25                  30

Met Ala Glu Leu Trp Met Gly Ala His Pro Lys Ser Ser Ser Arg Ile
        35                  40                  45

Glu Gly Ala Asp Gly Lys Ala Val Ser Leu Arg Asp Val Ile Glu His
    50                  55                  60

Asp Lys Ala Thr Leu Leu Gly Glu Ser Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Met Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140
```

Met Asn Ala Phe Arg Glu Phe Ser Glu Val Val Ser Leu Leu Gln Pro
145                 150                 155                 160

Val Ser Gly Ala His Thr Ala Ile Ala His Phe Leu Gln Glu Pro Asn
                165                 170                 175

Ala Glu Arg Leu Ser Gln Leu Phe Ala Ser Leu Leu Asn Met Gln Gly
            180                 185                 190

Asp Glu Lys Ser Arg Ala Leu Ala Val Leu Lys Ala Ala Leu Asn Ser
        195                 200                 205

Gln Gln Gly Glu Pro Trp Gln Thr Ile Arg Val Ile Ser Glu Phe Tyr
    210                 215                 220

Pro Asp Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Val Ala Lys Pro Ala Asp Gln Leu Leu Thr Thr
    290                 295                 300

Pro Val Lys His Gly Thr Glu Leu Asp Phe Pro Ile Pro Val Glu Asp
305                 310                 315                 320

Phe Ala Phe Ser Leu His Asp Leu Ser Ala Gln Glu Thr Ala Ile Ser
                325                 330                 335

Gln Gln Ser Ala Ala Ile Leu Phe Cys Val Glu Gly Glu Ala
            340                 345                 350

<210> SEQ ID NO 24
<211> LENGTH: 444
<212> TYPE: PRT
<213> ORGANISM: Citrobacter koseri

<400> SEQUENCE: 24

Met Glu Phe Ile Met Gln Ala Tyr Phe Asp Gln Leu Asp Arg Val Arg
1               5                   10                  15

Tyr Glu Gly Pro Lys Ser Thr Asn Pro Leu Ala Phe Arg His Tyr Asn
                20                  25                  30

Pro Asp Glu Ile Val Leu Gly Lys Arg Met Glu Asp His Leu Arg Phe
            35                  40                  45

Ala Ala Cys Tyr Trp His Thr Phe Cys Trp Asn Gly Ala Asp Met Phe
        50                  55                  60

Gly Val Gly Ala Phe Asn Arg Pro Trp Gln Gln Pro Gly Asp Ala Leu
65                  70                  75                  80

Glu Leu Ala Lys Arg Lys Ala Asp Val Ala Phe Glu Phe Phe His Lys
                85                  90                  95

Leu Asn Val Pro Tyr Tyr Cys Phe His Asp Val Asp Val Ser Pro Glu
                100                 105                 110

Gly Ala Ser Leu Lys Glu Tyr Lys Asn Asn Phe Ala Gln Met Val Asp
            115                 120                 125

Val Leu Glu Ser Lys Gln Glu Ser Gly Val Lys Leu Leu Trp Gly
        130                 135                 140

Thr Ala Asn Cys Phe Thr Asn Pro Arg Tyr Gly Ala Gly Ala Ala Thr
145                 150                 155                 160

Asn Pro Asp Pro Glu Val Phe Ser Trp Ala Ala Thr Gln Val Val Asn
                165                 170                 175

```
Ala Met Asn Ala Thr His Lys Leu Gly Gly Glu Asn Tyr Val Leu Trp
            180                 185                 190

Gly Gly Arg Glu Gly Tyr Glu Thr Leu Leu Asn Thr Asp Leu Arg Gln
        195                 200                 205

Glu Arg Glu Gln Ile Gly Arg Phe Met Gln Met Val Val Glu His Lys
    210                 215                 220

His Lys Thr Gly Phe Gln Gly Thr Leu Leu Ile Glu Pro Lys Pro Gln
225                 230                 235                 240

Glu Pro Thr Lys His Gln Tyr Asp Tyr Asp Val Ala Thr Val Tyr Gly
                245                 250                 255

Phe Leu Lys Gln Phe Gly Leu Glu Lys Glu Ile Lys Val Asn Ile Glu
            260                 265                 270

Ala Asn His Ala Thr Leu Ala Gly His Ser Phe His His Glu Ile Ala
        275                 280                 285

Ser Ala Ile Ala Leu Gly Ile Phe Gly Ser Val Asp Ala Asn Arg Gly
    290                 295                 300

Asp Ala Gln Leu Gly Trp Asp Thr Asp Gln Phe Pro Val Ser Val Glu
305                 310                 315                 320

Glu Asn Ala Leu Val Met Tyr Glu Ile Leu Lys Ala Gly Gly Phe Thr
                325                 330                 335

Thr Gly Gly Leu Asn Phe Asp Ala Lys Val Arg Arg Gln Ser Thr Asp
            340                 345                 350

Lys Tyr Asp Leu Phe Tyr Gly His Ile Gly Ala Met Asp Thr Met Ala
        355                 360                 365

Leu Ser Leu Lys Val Ala Arg Met Ile Glu Asp Gly Glu Leu Asp
    370                 375                 380

Lys Arg Val Ala Lys Arg Tyr Ser Gly Trp Asn Ser Glu Leu Gly Gln
385                 390                 395                 400

Gln Ile Leu Lys Gly Gln Leu Ser Leu Ser Asp Val Ala His Tyr Ala
                405                 410                 415

Glu Gln Arg Asn Leu Ala Pro Val His Gln Ser Gly His Gln Glu Leu
            420                 425                 430

Leu Glu Asn Leu Val Asn His Tyr Leu Phe Asp Lys
        435                 440

<210> SEQ ID NO 25
<211> LENGTH: 391
<212> TYPE: PRT
<213> ORGANISM: Citrobacter rodentium

<400> SEQUENCE: 25

Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Gln Gln Leu Pro
            20                  25                  30

Met Ala Glu Leu Trp Met Gly Ala His Pro Lys Ser Ser Ser Gln Val
        35                  40                  45

Val Asp Ala Ser Gly Gln Arg Val Ser Leu Arg Asp Val Ile Glu Ala
    50                  55                  60

Asp Lys Ser Arg Leu Leu Gly Asp Ala Val Ala Arg Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys Arg Asn Ser Glu Leu Gly Phe Ala Lys Glu
```

Asn Val Ala Gly Ile Pro Met Asp Ala Ala Glu Arg Asn Tyr Lys Asp
            100                 105                 110
Pro Asn His Lys Pro Glu Leu Val Phe Ala Leu Thr Pro Phe Leu Ala
        115                 120                 125
Met Asn Ala Phe Arg Glu Phe Ser Glu Ile Val Ser Leu Leu Gln Pro
    130                 135                 140
Val Ala Gly Ala His Thr Ala Ile Ala His Phe Leu Glu Ala Pro Asp
145                 150                 155                 160
Ala Glu Arg Leu Ser Ala Leu Phe Ala Ala Leu Leu Asn Met Gln Gly
                165                 170                 175
Glu Glu Lys Ser Arg Ala Leu Ala Ile Leu Lys Ala Ala Leu Glu Thr
            180                 185                 190
Gln Ser Gly Glu Pro Trp Gln Thr Ile Arg Leu Ile Gly Glu Phe Tyr
        195                 200                 205
Pro Asp Asp Ser Gly Leu Phe Ser Pro Leu Leu Leu Asn Val Val Lys
    210                 215                 220
Leu Asn Pro Gly Glu Ala Met Phe Leu Phe Ala Glu Thr Pro His Ala
225                 230                 235                 240
Tyr Leu Gln Gly Val Ala Leu Glu Val Met Ala Asn Ser Asp Asn Val
                245                 250                 255
Leu Arg Ala Gly Leu Thr Pro Lys Tyr Ile Asp Ile Pro Glu Leu Val
            260                 265                 270
Ala Asn Val Lys Phe Glu Ala Lys Pro Ala Asp Arg Leu Leu Thr Ala
        275                 280                 285
Pro Leu Thr Ser Gly Ala Glu Gln Asp Phe Pro Ile Pro Val Asp Asp
    290                 295                 300
Phe Ala Phe Ser Leu His Asp Leu Ser Ala Gln Gln Ala Glu Ile Ala
305                 310                 315                 320
Gln Gln Ser Ala Ala Ile Leu Phe Cys Val Glu Gly Glu Ala Thr Leu
                325                 330                 335
Arg Lys Gly Glu Gln Ser Leu Thr Leu Lys Pro Gly Glu Ser Ala Phe
            340                 345                 350
Ile Ser Ala Ala Glu Ser Pro Val Ser Val Ser Gly Ala Gly Arg Leu
        355                 360                 365
Ala Arg Val Tyr Asn Lys Leu
    370                 375                 380

385                 390

<210> SEQ ID NO 26
<211> LENGTH: 302
<212> TYPE: PRT
<213> ORGANISM: Citrobacter rodentium

<400> SEQUENCE: 26

Met Arg Ile Gly Ile Asp Leu Gly Gly Thr Lys Thr Glu Val Ile Ala
1               5                   10                  15
Leu Gly Glu Ser Gly Glu Gln Leu Phe Arg His Arg Leu Pro Thr Pro
            20                  25                  30
Arg Asn Asp Tyr Arg Gln Thr Ile Glu Thr Ile Ala Thr Leu Val Glu
        35                  40                  45
Met Ala Glu Lys Ala Thr Gly Gln Thr Gly Thr Val Gly Met Gly Ile
    50                  55                  60
Pro Gly Ser Leu Ser Pro Tyr Thr Gly Val Val Lys Asn Ala Asn Ser
65                  70                  75                  80

```
Thr Trp Leu Asn Gly Gln Pro Phe Asp Arg Asp Val Ser Ala Arg Leu
                85                  90                  95

Gln Arg Glu Val Arg Leu Ala Asn Asp Ala Asn Cys Leu Ala Val Ser
            100                 105                 110

Glu Ala Val Asp Gly Ala Ala Gly Ala Gln Thr Val Phe Ala Val
            115                 120                 125

Ile Ile Gly Thr Gly Cys Gly Ala Gly Val Ala Leu Asn Gly Arg Ala
            130                 135                 140

His Ala Gly Gly Asn Gly Thr Ala Gly Glu Trp Gly His Asn Pro Leu
145                 150                 155                 160

Pro Trp Met Asp Asp Glu Leu Arg Tyr Arg Glu Glu Val Pro Cys
                165                 170                 175

Tyr Cys Gly Lys Gln Gly Cys Ile Glu Thr Phe Ile Ser Gly Thr Gly
                180                 185                 190

Phe Ala Thr Asp Tyr Gln Arg Leu Ser Gly Asn Ser Leu Thr Gly Asn
            195                 200                 205

Glu Ile Met Arg Arg Val Glu Glu Gln Asp Pro Leu Ala Glu Leu Ala
            210                 215                 220

Leu Gly Arg Tyr Glu Leu Arg Leu Ala Lys Ser Leu Ala His Val Val
225                 230                 235                 240

Asn Ile Leu Asp Pro Asp Val Ile Val Leu Gly Gly Met Ser Asn
                245                 250                 255

Val Asp Arg Leu Tyr Asn Thr Leu Pro Ala Leu Ile Gly Gln Phe Val
                260                 265                 270

Phe Gly Gly Glu Cys Glu Thr Pro Val Arg Lys Ala Leu His Gly Asp
            275                 280                 285

Ser Ser Gly Val Arg Gly Ala Ala Trp Leu Trp Pro Gln Arg
    290                 295                 300

<210> SEQ ID NO 27
<211> LENGTH: 440
<212> TYPE: PRT
<213> ORGANISM: Citrobacter rodentium

<400> SEQUENCE: 27

Met Gln Ala Tyr Phe Asp Gln Leu Asp Arg Val Arg Phe Glu Gly Pro
1               5                   10                  15

Lys Ser Thr Asn Pro Leu Ala Phe Arg His Tyr Asn Pro Asp Glu Ile
                20                  25                  30

Val Leu Gly Lys Arg Met Glu Asp His Leu Arg Phe Ala Ala Cys Tyr
            35                  40                  45

Trp His Thr Phe Cys Trp Asn Gly Ala Asp Met Phe Gly Val Gly Ala
50                  55                  60

Phe Asp Arg Pro Trp Gln Pro Gly Glu Ala Leu Ala Leu Ala Lys
65                  70                  75                  80

Arg Lys Ala Asp Val Ala Phe Glu Phe Phe His Lys Leu Asn Val Pro
                85                  90                  95

Phe Tyr Cys Phe His Asp Val Asp Val Ser Pro Glu Gly Ala Ser Leu
            100                 105                 110

Lys Glu Tyr Lys Asn Asn Phe Ala Gln Met Val Asp Val Leu Ala Ala
            115                 120                 125

Lys Gln Glu Glu Ser Gly Val Lys Leu Leu Trp Gly Thr Ala Asn Cys
            130                 135                 140

Phe Thr Asn Pro Arg Tyr Gly Ala Gly Ala Ala Thr Asn Pro Asp Pro
145                 150                 155                 160
```

-continued

```
Glu Val Phe Ser Trp Ala Ala Thr Gln Val Val Thr Ala Met Asp Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Ile Gly Arg Phe Met Gln Met Val Val Glu His Lys His Lys Thr Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ser Leu Lys
        355                 360                 365

Ile Ala Ala Arg Met Ile Glu Asp Gly Glu Leu Asp Lys Arg Val Ala
    370                 375                 380

Lys Arg Tyr Ala Gly Trp Asn Ser Glu Leu Gly Gln Gln Ile Leu Lys
385                 390                 395                 400

Gly Gln Met Ser Leu Ser Glu Leu Ala Gln Tyr Ala Glu Gln His Asn
                405                 410                 415

Leu Ala Pro Val His Gln Ser Gly His Gln Glu Leu Leu Glu Asn Leu
            420                 425                 430

Val Asn His Tyr Leu Phe Asn Lys
        435                 440

<210> SEQ ID NO 28
<211> LENGTH: 416
<212> TYPE: PRT
<213> ORGANISM: Citrobacter youngae

<400> SEQUENCE: 28

Met Cys Arg Leu Leu Pro Leu Gly Phe Leu Gly Leu Ile Ala Ala Glu
1               5                   10                  15

Asn Ser Thr Leu Lys Gln Gly Leu Arg Met Gln Lys Leu Ile Asn Ser
            20                  25                  30

Val Gln Asn Tyr Ala Trp Gly Ser Lys Thr Ala Leu Thr Glu Leu Tyr
        35                  40                  45

Gly Met Ala Asn Pro Ala Gln Gln Pro Met Ala Glu Leu Trp Met Gly
    50                  55                  60

Ala His Pro Lys Ser Ser Ser Gln Val Leu Gly Ala Asp Gly Gln Thr
65                  70                  75                  80

Ile Ala Leu Arg Asp Val Ile Glu Arg Asp Lys Ser Ala Leu Leu Gly
```

```
                85                  90                  95
Glu Ala Val Ala Lys Arg Phe Gly Glu Leu Pro Phe Leu Phe Lys Val
            100                 105                 110

Leu Cys Ala Ala Gln Pro Leu Ser Ile Gln Val His Pro Asn Lys His
            115                 120                 125

Asn Ser Glu Ile Gly Phe Ala Lys Glu Asn Ala Ala Gly Ile Pro Met
        130                 135                 140

Asp Ala Ala Glu Arg Asn Tyr Lys Asp Pro Asn His Lys Pro Glu Leu
145                 150                 155                 160

Val Phe Ala Leu Thr Pro Phe Leu Ala Met Asn Ala Phe Arg Glu Phe
                165                 170                 175

Ser Asp Ile Val Ala Leu Leu Gln Pro Val Ser Ala Ala His Pro Ala
            180                 185                 190

Ile Ala His Phe Leu Gln Glu Pro Cys Ala Glu Arg Leu Ser Tyr Leu
        195                 200                 205

Phe Ala Ser Leu Leu Asn Met Gln Asp Glu Lys Ser His Ala Leu
    210                 215                 220

Ala Ile Leu Lys Ser Ala Leu Asn Ser Gln Gln Gly Glu Pro Trp Gln
225                 230                 235                 240

Thr Ile Arg Leu Val Ala Asp Phe Tyr Pro Asn Asp Ser Gly Leu Phe
                245                 250                 255

Ser Pro Leu Leu Leu Asn Val Val Lys Leu Asn Pro Gly Glu Ala Met
            260                 265                 270

Phe Leu Phe Ala Glu Thr Pro His Ala Tyr Leu Gln Gly Val Ala Leu
        275                 280                 285

Glu Val Met Ala Asn Ser Asp Asn Val Leu Arg Ala Gly Leu Thr Pro
290                 295                 300

Lys Tyr Ile Asp Ile Pro Glu Leu Val Ala Asn Val Lys Phe Val Ala
305                 310                 315                 320

Lys Pro Ala Asn Gln Leu Leu Thr Thr Pro Ile Lys Thr Ala Gly Glu
                325                 330                 335

Leu Asp Phe Pro Ile Pro Val Asp Asp Phe Ala Phe Ser Leu His Glu
            340                 345                 350

Leu Thr Ala Asp Gly Ala Asp Ile Ser Gln Gln Ser Ala Ala Ile Leu
        355                 360                 365

Phe Cys Ile Glu Gly Gln Ala Val Leu Ser Lys Gly Glu Gln Arg Leu
    370                 375                 380

Val Leu Gln Pro Gly Glu Ser Ala Phe Ile Ser Ala Asn Glu Ser Pro
385                 390                 395                 400

Val Asn Val Ser Gly Thr Gly Arg Leu Ala Arg Val Tyr Asn Lys Leu
                405                 410                 415

<210> SEQ ID NO 29
<211> LENGTH: 444
<212> TYPE: PRT
<213> ORGANISM: Citrobacter youngae

<400> SEQUENCE: 29

Met Glu Leu Ile Met Gln Ala Tyr Phe Asp Gln Leu Asp Arg Val Arg
1               5                   10                  15

Phe Glu Gly Thr Lys Ser Thr Asn Pro Leu Ala Phe Arg His Tyr Asn
            20                  25                  30

Pro Asp Glu Ile Val Leu Gly Lys Arg Met Glu Asp His Leu Arg Phe
        35                  40                  45
```

```
Ala Ala Cys Tyr Trp His Thr Phe Cys Trp Asn Gly Ala Asp Met Phe
 50                  55                  60
Gly Met Gly Ala Phe Asp Arg Pro Trp Gln Gln Pro Gly Glu Ala Leu
 65                  70                  75                  80
Ala Leu Ala Lys Arg Lys Ala Asp Val Ala Phe Glu Phe Phe His Lys
                 85                  90                  95
Leu Asn Val Pro Tyr Tyr Cys Phe His Asp Val Asp Val Ser Pro Glu
                100                 105                 110
Gly Ala Ser Leu Lys Glu Tyr Lys Asn Asn Phe Ala Gln Met Val Asp
            115                 120                 125
Val Leu Ala Ala Lys Gln Glu Gln Ser Gly Val Lys Leu Leu Trp Gly
130                 135                 140
Thr Ala Asn Cys Phe Thr Asn Pro Arg Tyr Gly Ala Gly Ala Ala Thr
145                 150                 155                 160
Asn Pro Asp Pro Glu Val Phe Ser Trp Ala Ala Thr Gln Val Val Thr
                165                 170                 175
Ala Met Asp Ala Thr His Lys Leu Gly Gly Glu Asn Tyr Val Leu Trp
            180                 185                 190
Gly Gly Arg Glu Gly Tyr Glu Thr Leu Leu Asn Thr Asp Leu Arg Gln
        195                 200                 205
Glu Arg Glu Gln Ile Gly Arg Phe Met Gln Leu Val Val Glu His Lys
210                 215                 220
His Lys Ile Gly Phe Gln Gly Thr Leu Leu Ile Glu Pro Lys Pro Gln
225                 230                 235                 240
Glu Pro Thr Lys His Gln Tyr Asp Tyr Asp Ala Ala Thr Val Tyr Gly
                245                 250                 255
Phe Leu Lys Gln Phe Gly Leu Glu Lys Glu Ile Lys Leu Asn Ile Glu
            260                 265                 270
Ala Asn His Ala Thr Leu Ala Gly His Ser Phe His His Glu Ile Ala
        275                 280                 285
Thr Ala Ile Ala Leu Gly Leu Phe Gly Ser Val Asp Ala Asn Arg Gly
290                 295                 300
Asp Ala Gln Leu Gly Trp Asp Thr Asp Gln Phe Pro Asn Ser Val Glu
305                 310                 315                 320
Glu Asn Ala Leu Val Met Tyr Glu Ile Leu Lys Ala Gly Gly Phe Thr
                325                 330                 335
Thr Gly Gly Leu Asn Phe Asp Ala Lys Val Arg Arg Gln Ser Thr Asp
            340                 345                 350
Lys Tyr Asp Leu Phe Tyr Gly His Ile Gly Ala Met Asp Thr Met Ala
        355                 360                 365
Leu Ser Leu Lys Ile Ala Ala Arg Met Ile Glu Asp Gly Gly Leu Asp
370                 375                 380
Gln Arg Val Ala Lys Arg Tyr Ala Gly Trp Asn Gly Glu Leu Gly Gln
385                 390                 395                 400
Gln Ile Leu Lys Gly Gln Met Thr Leu Thr Glu Ile Ala Gln Tyr Ala
                405                 410                 415
Glu Gln His Asn Leu Ala Pro Val His Gln Ser Gly His Gln Glu Gln
            420                 425                 430
Leu Glu Asn Leu Val Asn His Tyr Leu Phe Asp Lys
        435                 440

<210> SEQ ID NO 30
<211> LENGTH: 391
<212> TYPE: PRT
```

<213> ORGANISM: Salmonella enterica

<400> SEQUENCE: 30

```
Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Gln Gln Gln Pro
            20                  25                  30

Met Ala Glu Leu Trp Met Gly Ala His Pro Lys Ser Ser Arg Ile
        35                  40                  45

Thr Thr Ala Asn Gly Glu Thr Val Ser Leu Arg Asp Ala Ile Glu Lys
    50                  55                  60

Asn Lys Thr Ala Met Leu Gly Glu Ala Val Ala Asn Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys Arg Asn Ser Glu Ile Gly Phe Ala Lys Glu
            100                 105                 110

Asn Ala Ala Gly Ile Pro Met Asp Ala Ala Glu Arg Asn Tyr Lys Asp
            115                 120                 125

Pro Asn His Lys Pro Glu Leu Val Phe Ala Leu Thr Pro Phe Leu Ala
130                 135                 140

Met Asn Ala Phe Arg Glu Phe Ser Asp Ile Val Ser Leu Leu Gln Pro
145                 150                 155                 160

Val Ala Gly Ala His Ser Ala Ile Ala His Phe Leu Gln Ala Pro Asn
                165                 170                 175

Ala Glu Arg Leu Ser Gln Leu Phe Ala Ser Leu Leu Asn Met Gln Gly
            180                 185                 190

Glu Glu Lys Ser Arg Ala Leu Ala Val Leu Lys Ala Ala Leu Asn Ser
            195                 200                 205

Gln Gln Gly Glu Pro Trp Gln Thr Ile Arg Val Ile Ser Glu Tyr Tyr
        210                 215                 220

Pro Asp Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Pro Lys Pro Ala Ser Glu Leu Leu Thr Ala
        290                 295                 300

Pro Val Lys Ser Gly Ala Glu Leu Asp Phe Pro Ile Pro Val Asp Asp
305                 310                 315                 320

Phe Ala Phe Ser Leu His Asp Leu Ala Leu Gln Glu Thr Ser Ile Gly
                325                 330                 335

Gln His Ser Ala Ala Ile Leu Phe Cys Val Glu Gly Glu Ala Val Leu
            340                 345                 350

Arg Lys Asp Glu Gln Arg Leu Val Leu Lys Pro Gly Glu Ser Ala Phe
        355                 360                 365

Ile Gly Ala Asp Glu Ser Pro Val Asn Ala Ser Gly Thr Gly Arg Leu
        370                 375                 380

Ala Arg Val Tyr Asn Lys Leu
385                 390
```

<210> SEQ ID NO 31
<211> LENGTH: 440
<212> TYPE: PRT
<213> ORGANISM: Salmonella enterica

<400> SEQUENCE: 31

```
Met Gln Ala Tyr Phe Asp Gln Leu Asp Arg Val Arg Tyr Glu Gly Pro
1               5                   10                  15

Gln Ser Thr Asn Pro Leu Ala Phe Arg His Tyr Asn Pro Asp Glu Leu
            20                  25                  30

Val Leu Gly Lys Arg Met Glu Asp His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Glu Leu Ala Lys
65                  70                  75                  80

Arg Lys Ala Asp Val Ala Phe Glu Phe Phe His Lys Leu Asn Val Pro
                85                  90                  95

Phe Tyr Cys Phe His Asp Val Asp Val Ser Pro Glu Gly Ala Ser Leu
            100                 105                 110

Lys Glu Tyr Lys Asn Asn Phe Ala Gln Met Val Asp Val Leu Ala Ala
        115                 120                 125

Lys Gln Glu Gln Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Asn Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Ile Gly Arg Phe Met Gln Met Val Val Glu His Lys His Lys Met Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Val Ala Thr Val Tyr Gly Phe Leu Lys Gln
                245                 250                 255

Phe Gly Leu Glu Lys Glu Ile Lys Val Asn Ile Glu Ala Asn His Ala
            260                 265                 270

Thr Leu Ala Gly His Ser Phe His His Glu Ile Ala Thr Ala Ile Ala
        275                 280                 285

Leu Gly Ile Phe Gly Ser Val Asp Ala Asn Arg Gly Asp Ala Gln Leu
    290                 295                 300

Gly Trp Asp Thr Asp Gln Phe Pro Ile Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ser Leu Lys
        355                 360                 365

Ile Ala Ala Arg Met Val Glu Asp Gly Glu Leu Asp Lys Arg Val Ala
    370                 375                 380
```

Lys Arg Tyr Ala Gly Trp Asn Gly Glu Leu Gly Gln Gln Ile Leu Lys
385                 390                 395                 400

Gly Gln Leu Ser Leu Gly Glu Leu Ala Gln Tyr Ala Glu Gln His His
            405                 410                 415

Leu Ala Pro Val His Gln Ser Gly His Gln Glu Leu Leu Glu Asn Leu
        420                 425                 430

Val Asn Arg Tyr Leu Phe Asp Lys
        435                 440

<210> SEQ ID NO 32
<211> LENGTH: 391
<212> TYPE: PRT
<213> ORGANISM: Salmonella typhimurium

<400> SEQUENCE: 32

Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Gln Gln Gln Pro
            20                  25                  30

Met Ala Glu Leu Trp Met Gly Ala His Pro Lys Ser Ser Ser Arg Ile
        35                  40                  45

Thr Thr Ala Asn Gly Glu Thr Val Ser Leu Arg Asp Ala Ile Glu Lys
    50                  55                  60

Asn Lys Thr Ala Met Leu Gly Glu Ala Val Ala Asn Arg Phe Gly Glu
65                  70                  75                  80

Leu Pro Phe Leu Phe Lys Val Leu Cys Ala Ala Lys Pro Leu Ser Ile
                85                  90                  95

Gln Val His Pro Asn Lys Arg Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
130                 135                 140

Met Asn Ala Phe Arg Glu Phe Ser Asp Ile Val Ser Leu Leu Gln Pro
145                 150                 155                 160

Val Ala Gly Ala His Ser Ala Ile Ala His Phe Leu Gln Val Pro Asn
                165                 170                 175

Ala Glu Arg Leu Ser Gln Leu Phe Ala Ser Leu Leu Asn Met Gln Gly
            180                 185                 190

Glu Glu Lys Ser Arg Ala Leu Ala Val Leu Lys Ala Ala Leu Asn Ser
        195                 200                 205

Gln Gln Gly Glu Pro Trp Gln Thr Ile Arg Val Ile Ser Glu Tyr Tyr
    210                 215                 220

Pro Asp Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Pro Lys Pro Ala Gly Glu Leu Leu Thr Ala
    290                 295                 300

Pro Val Lys Ser Gly Ala Glu Leu Asp Phe Pro Ile Pro Val Asp Asp

```
                305                 310                 315                 320
        Phe Ala Phe Ser Leu His Asp Leu Ala Leu Gln Glu Thr Ser Ile Gly
                        325                 330                 335

Gln His Ser Ala Ala Ile Leu Phe Cys Val Glu Gly Glu Ala Val Leu
                        340                 345                 350

Arg Lys Asp Glu Gln Arg Leu Val Leu Lys Pro Gly Glu Ser Ala Phe
                        355                 360                 365

Ile Gly Ala Asp Glu Ser Pro Val Asn Ala Ser Gly Thr Gly Arg Leu
                        370                 375                 380

Ala Arg Val Tyr Asn Lys Leu
        385                 390

<210> SEQ ID NO 33
<211> LENGTH: 391
<212> TYPE: PRT
<213> ORGANISM: Enterobacter cloacae

<400> SEQUENCE: 33

Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Asp Asn Leu Pro
                20                  25                  30

Met Ala Glu Leu Trp Met Gly Ala His Pro Lys Ser Ser Ser Lys Val
            35                  40                  45

Glu Asp Ala Ser Gly Gln Val Arg Ala Leu Arg Asp Val Ile Asp Ala
        50                  55                  60

Asp Lys Ala Thr Leu Leu Gly Asn Ser Val Ala Ser Arg Phe Gly Glu
65                  70                  75                  80

Leu Pro Phe Leu Phe Lys Val Leu Cys Ala Asp Gln Pro Leu Ser Ile
                85                  90                  95

Gln Val His Pro Asn Lys Lys Ala Ser Glu Ile Gly Phe Ala Lys Glu
                100                 105                 110

Asn Ala Ala Gly Ile Pro Leu Asp Ala Ala Glu Arg Asn Tyr Lys Asp
            115                 120                 125

Pro Asn His Lys Pro Glu Leu Val Phe Ala Leu Thr Pro Phe Leu Ala
        130                 135                 140

Met Asn Ala Phe Arg Glu Phe Ser Glu Ile Ile Ser Leu Leu Gln Pro
145                 150                 155                 160

Val Ala Gly Ala His Asn Ala Ile Ala His Phe Leu Ala Asn Pro Asn
                165                 170                 175

Ala Glu Ser Leu Ser Gln Leu Phe Ala Ser Leu Leu Asn Met Gln Gly
            180                 185                 190

Asp Glu Lys Ser His Ala Arg Ala Val Leu Lys Ala Ala Leu Asp Gly
        195                 200                 205

Gln Gln Gly Glu Pro Trp Asp Thr Ile Arg Leu Ile Ser Ala Phe Tyr
    210                 215                 220

Pro Asp Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285
```

```
Ala Asn Val Lys Phe Val Ala Lys Pro Ala Ala Glu Leu Leu Thr Gln
    290                 295                 300

Pro Val Lys Asn Gly Ala Glu Leu Asp Phe Pro Ile Pro Val Asp Asp
305                 310                 315                 320

Phe Ala Phe Ser Leu His Asp Leu Ser Gln Thr Glu Thr Thr Ile Ala
                325                 330                 335

Gln Glu Ser Ala Ala Ile Leu Phe Cys Val Glu Gly Glu Ala Thr Leu
            340                 345                 350

His Lys Gly Glu Gln Arg Leu Val Leu Lys Pro Gly Glu Ser Ala Phe
        355                 360                 365

Val Ala Ala Asn Glu Ser Pro Val Ser Val Ser Gly Thr Gly Arg Leu
370                 375                 380

Ala Arg Val Phe Asn Lys Leu
385                 390

<210> SEQ ID NO 34
<211> LENGTH: 461
<212> TYPE: PRT
<213> ORGANISM: Enterobacter cloacae

<400> SEQUENCE: 34

Met Ser Ile His Tyr Tyr Ser Cys Ile Asn Asp Ser Pro His Thr Leu
1               5                   10                  15

Ile Met Glu Leu Asn Met Gln Ala Tyr Phe Asp Gln Leu Asp Arg Val
            20                  25                  30

Arg Tyr Glu Gly Pro Lys Thr Thr Asn Pro Leu Ala Phe Arg His Tyr
        35                  40                  45

Asn Pro Asp Glu Leu Val Leu Gly Lys Arg Met Glu Asp His Leu Arg
50                  55                  60

Phe Ala Ala Cys Tyr Trp His Thr Phe Cys Trp Asn Gly Ala Asp Met
65                  70                  75                  80

Phe Gly Val Gly Ser Phe Asp Arg Pro Trp Gln Gln Pro Gly Glu Ala
                85                  90                  95

Ile Glu Leu Ala Lys Arg Lys Ala Asp Val Ala Phe Glu Phe Phe His
            100                 105                 110

Lys Leu Asn Val Pro Tyr Tyr Cys Phe His Asp Val Asp Val Ser Pro
        115                 120                 125

Glu Gly Ala Ser Leu Lys Glu Tyr Leu Asn Asn Phe Ala Gln Met Val
130                 135                 140

Asp Val Leu Ala Ala Lys Gln Gln Ser Gly Val Lys Leu Leu Trp
145                 150                 155                 160

Gly Thr Ala Asn Cys Phe Thr Asn Pro Arg Tyr Gly Ala Gly Ala Ala
                165                 170                 175

Thr Asn Pro Asp Pro Glu Val Phe Ser Trp Ala Ala Thr Gln Val Val
            180                 185                 190

Thr Ala Met Asn Ala Thr His Gln Leu Gly Gly Glu Asn Tyr Val Leu
        195                 200                 205

Trp Gly Gly Arg Glu Gly Tyr Glu Thr Leu Leu Asn Thr Asp Leu Arg
210                 215                 220

Gln Glu Arg Glu Gln Ile Gly Arg Phe Met Gln Met Val Val Glu His
225                 230                 235                 240

Lys His Lys Ile Gly Phe Arg Gly Thr Leu Leu Ile Glu Pro Lys Pro
                245                 250                 255

Gln Glu Pro Thr Lys His Gln Tyr Asp Tyr Asp Val Ala Thr Val Tyr
            260                 265                 270
```

```
Gly Phe Leu Lys Gln Phe Gly Leu Glu Lys Glu Ile Lys Val Asn Ile
            275                 280                 285

Glu Ala Asn His Ala Thr Leu Ala Gly His Ser Phe His His Glu Ile
        290                 295                 300

Ala Ser Ala Ile Ala Leu Gly Ile Phe Gly Ser Val Asp Ala Asn Arg
305                 310                 315                 320

Gly Asp Ala Gln Leu Gly Trp Asp Thr Asp Gln Phe Pro Asn Ser Val
            325                 330                 335

Glu Glu Asn Ala Leu Val Met Tyr Glu Ile Ile Lys Ala Gly Gly Phe
        340                 345                 350

Thr Thr Gly Gly Leu Asn Phe Asp Ala Lys Val Arg Arg Gln Ser Thr
            355                 360                 365

Asp Lys Tyr Asp Leu Phe Tyr Gly His Ile Gly Ala Met Asp Thr Met
370                 375                 380

Ala Leu Ala Leu Lys Val Ala Ala Arg Met Ile Glu Asp Gly Glu Leu
385                 390                 395                 400

Asp Lys Arg Val Ala Lys Arg Tyr Ser Gly Trp Asn Ser Glu Leu Gly
            405                 410                 415

Gln Gln Ile Leu Lys Gly Gln Leu Ser Leu Ala Glu Ile Ala Lys Tyr
            420                 425                 430

Ala Glu Gln His Gln Leu Ala Pro Gln His Gln Ser Gly His Gln Glu
            435                 440                 445

Leu Leu Glu Asn Leu Val Asn His Tyr Leu Phe Asp Lys
450                 455                 460

<210> SEQ ID NO 35
<211> LENGTH: 391
<212> TYPE: PRT
<213> ORGANISM: Enterobacter cancerogenus

<400> SEQUENCE: 35

Met Gln Lys Leu Ile Asn Ser Val Gln Asn Tyr Ala Trp Gly Ser Lys
1               5                   10                  15

Thr Ala Leu Thr Asp Leu Tyr Gly Ile Ala Asn Pro Asp Gln Leu Pro
            20                  25                  30

Met Ala Glu Leu Trp Met Gly Ala His Pro Lys Ser Ser Ser Lys Ile
        35                  40                  45

Glu Asp Ala Ser Gly Gln Val Arg Ser Leu Arg Asp Ala Ile Asp Ala
    50                  55                  60

Asp Lys Thr Ala Leu Leu Gly Asp Lys Val Ala Ser Arg Phe Gly Glu
65                  70                  75                  80

Leu Pro Phe Leu Phe Lys Val Leu Cys Ala Asp Gln Pro Leu Ser Ile
            85                  90                  95

Gln Val His Pro Asn Lys Lys Ala Ser Glu Ile Gly Phe Ala Lys Glu
            100                 105                 110

Asn Ala Ala Gly Ile Pro Leu Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140

Met Asn Ala Phe Arg Glu Phe Ser Glu Ile Ile Ser Leu Leu Gln Pro
145                 150                 155                 160

Val Ala Gly Ala Asn Asn Ala Ile Ala His Phe Leu Glu Asn Pro Asn
            165                 170                 175

Ala Glu Gly Leu Ser Gln Leu Phe Ala Ser Leu Leu Asn Met Gln Gly
```

```
                180             185             190
Glu Glu Lys Ser His Ala Leu Ala Ile Leu Lys Ala Ala Leu Asn Asp
            195                 200                 205
Gln Gln Gly Glu Pro Trp Asp Thr Ile Arg Val Ile Ser Glu Phe Tyr
            210                 215                 220
Pro Asp Asp Ser Gly Leu Phe Ser Pro Leu Leu Asn Val Val Lys
225                 230                 235                 240
Leu Asn Pro Gly Glu Ala Met Phe Leu Phe Ala Glu Thr Pro His Ala
                245                 250                 255
Tyr Leu Gln Gly Val Ala Leu Glu Val Met Ala Asn Ser Asp Asn Val
                260                 265                 270
Leu Arg Ala Gly Leu Thr Pro Lys Tyr Ile Asp Ile Pro Glu Leu Val
            275                 280                 285
Ala Asn Val Lys Phe Val Ala Lys Pro Ala Ala Glu Leu Leu Thr Gln
                290                 295                 300
Pro Val Lys Asn Gly Ala Glu Leu Asp Phe Pro Ile Pro Val Asp Asp
305                 310                 315                 320
Phe Ala Phe Ser Leu His Asp Leu Ser Ala Asp Glu Thr Ala Ile Ala
                325                 330                 335
Gln Glu Ser Ala Ala Ile Leu Phe Cys Val Glu Gly Ala Thr Leu
                340                 345                 350
His Lys Gly Glu Gln Arg Leu Val Leu Lys Pro Gly Ser Ala Phe
                355                 360                 365
Val Ala Ala Asn Glu Ser Pro Val Ser Ile Ser Gly Lys Gly Arg Leu
370                 375                 380
Ala Arg Val Phe Asn Lys Leu
385                 390

<210> SEQ ID NO 36
<211> LENGTH: 392
<212> TYPE: PRT
<213> ORGANISM: Cronobacter turicensis

<400> SEQUENCE: 36

Met Gln Lys Leu Ile Asn Ser Val Gln Asn Tyr Ala Trp Gly Ser Lys
1               5                   10                  15
Thr Ala Leu Thr Glu Leu Tyr Gly Val Ala Asn Pro Glu Gly Leu Pro
            20                  25                  30
Met Ala Glu Leu Trp Met Gly Ala His Pro Lys Ser Ser Lys Ile
            35                  40                  45
Gln Asp Asp Gln Gly Gln Thr Arg Ala Leu Arg Glu Val Ile Asp Ala
50                  55                  60
Asp Lys Thr Ala Leu Leu Gly Ala Pro Val Ala Glu Arg Phe Gly Glu
65                  70                  75                  80
Leu Pro Phe Leu Phe Lys Val Leu Cys Ala Asp Gln Pro Leu Ser Ile
                85                  90                  95
Gln Val His Pro Asn Lys Gln Ala Ser Glu Glu Gly Phe Ala Arg Glu
                100                 105                 110
Asn Ala Ala Gly Ile Pro Leu Asp Ala Ala Glu Arg Asn Tyr Lys Asp
                115                 120                 125
Pro Asn His Lys Pro Glu Leu Val Phe Ala Leu Thr Pro Phe Leu Ala
        130                 135                 140
Met Asn Ala Phe Arg Glu Phe Ser Glu Ile Val Ser Leu Leu Gln Pro
145                 150                 155                 160
```

```
Val Ala Gly Ala His Thr Ala Ile Ala His Phe Leu Ala Glu Pro Asn
                165                 170                 175

Ala Asp Arg Leu Arg Asp Leu Phe Ala Gly Leu Leu Asn Met Gln Gly
            180                 185                 190

Glu Glu Lys Ser Arg Ala Leu Ala Val Leu Lys Ala Thr Val Ala Ser
        195                 200                 205

Gln Gln Gly Glu Pro Trp Asp Thr Ile Arg Phe Ile Ala Gln Phe Tyr
    210                 215                 220

Pro Asp Asp Ser Gly Leu Phe Ser Pro Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Val Ala Lys Pro Ala Ala Gln Leu Leu Thr Gln
    290                 295                 300

Pro Glu Lys Asp Gly Ala Ala Leu Glu Phe Pro Ile Pro Val Glu Asp
305                 310                 315                 320

Phe Ala Phe Ser Leu His Asp Leu Gln Ser Gln Pro Gln Arg Leu Ala
                325                 330                 335

Gln Glu Ser Ala Ala Ile Leu Phe Cys Val Glu Gly Glu Ala Val Leu
            340                 345                 350

Ser Lys Gly Asp Glu Arg Leu Thr Leu Lys Pro Gly Glu Ser Ala Phe
        355                 360                 365

Val Ala Ala Asn Glu Ser Pro Val Asn Val Ser Gly Val Gly Arg Leu
    370                 375                 380

Ala Arg Val Tyr Asn Lys Leu Asn
385                 390

<210> SEQ ID NO 37
<211> LENGTH: 392
<212> TYPE: PRT
<213> ORGANISM: Cronobacter sakazakii

<400> SEQUENCE: 37

Met Gln Lys Leu Ile Asn Ser Val Gln Asn Tyr Ala Trp Gly Ser Lys
1               5                   10                  15

Thr Ala Leu Thr Glu Leu Tyr Gly Val Ala Asn Pro Glu Gly Leu Pro
            20                  25                  30

Met Ala Glu Leu Trp Met Gly Ala His Pro Lys Ser Ser Ser Lys Ile
        35                  40                  45

Gln Asp Ala Gln Gly Gln Thr Arg Ala Leu Arg Glu Val Ile Asp Ala
    50                  55                  60

Asp Lys Thr Ala Leu Leu Gly Ala Pro Val Ala Glu Arg Phe Gly Glu
65                  70                  75                  80

Leu Pro Phe Leu Phe Lys Val Leu Cys Ala Asp Gln Pro Leu Ser Ile
                85                  90                  95

Gln Val His Pro Asn Lys Gln Ala Ser Glu Glu Gly Phe Ala Arg Glu
            100                 105                 110

Asn Ala Ala Gly Ile Pro Leu Ser Ala Glu Arg Asn Tyr Lys Asp
        115                 120                 125

Pro Asn His Lys Pro Glu Leu Val Phe Ala Leu Thr Pro Phe Leu Ala
    130                 135                 140
```

```
Met Asn Ala Phe Arg Glu Phe Ser Glu Ile Val Ser Leu Leu Gln Pro
145                 150                 155                 160

Val Ala Gly Ala His Thr Ala Ile Ala His Phe Leu Ala Glu Pro Asn
                165                 170                 175

Ala Asp Arg Leu Arg Glu Leu Phe Ala Gly Leu Leu Asn Met Gln Gly
            180                 185                 190

Glu Glu Lys Ser Arg Ala Leu Ala Val Leu Lys Ala Thr Val Ala Ser
        195                 200                 205

Gln Gln Gly Glu Pro Trp Glu Thr Ile Arg Phe Ile Ala Gln Phe Tyr
210                 215                 220

Pro Asp Asp Ser Gly Leu Phe Ser Pro Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Val Ala Lys Pro Ala Gly Glu Leu Leu Thr Gln
290                 295                 300

Pro Val Lys Gln Glu Ser Ala Leu Glu Phe Pro Ile Pro Val Glu Asp
305                 310                 315                 320

Phe Ala Phe Ser Leu His Asp Leu Asn Ser Gln Pro Gln Ser Leu Ala
                325                 330                 335

Gln Glu Ser Ala Ala Ile Leu Phe Cys Val Gly Glu Ala Val Leu
            340                 345                 350

Ser Lys Gly Asp Glu Arg Leu Thr Leu Lys Pro Gly Ser Ala Phe
        355                 360                 365

Val Ala Ala Ser Glu Ser Pro Val Arg Ala Ser Gly Val Gly Arg Leu
370                 375                 380

Ala Arg Val Tyr Asn Lys Leu Asn
385                 390

<210> SEQ ID NO 38
<211> LENGTH: 392
<212> TYPE: PRT
<213> ORGANISM: Klebsiella pneumoniae

<400> SEQUENCE: 38

Met Gln Lys Leu Ile Asn Ala Val Gln Asn Tyr Ala Trp Gly Ser His
1               5                   10                  15

Thr Ala Leu Thr Glu Leu Tyr Gly Ile Ala Asn Pro Asp Asn Leu Pro
            20                  25                  30

Met Ala Glu Leu Trp Met Gly Ala His Pro Lys Ser Ser Gln Ile
        35                  40                  45

Leu Ala Ala Asp Gly Gln Pro Arg Ser Leu Arg Glu Val Ile Asp Ala
    50                  55                  60

Asp Lys Thr Ala Leu Leu Gly Asp Lys Val Ala Ala Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys Gln Ala Ser Glu Glu Gly Phe Ala Arg Glu
            100                 105                 110

Asn Ala Ala Gly Ile Pro Leu Ser Ala Ala Glu Arg Asn Tyr Lys Asp
```

```
            115                 120                 125
Pro Asn His Lys Pro Glu Leu Val Phe Ala Leu Thr Pro Phe Leu Ala
    130                 135                 140

Met Asn Ala Phe Arg Glu Phe Ser Glu Ile Val Thr Leu Leu Gln Pro
145                 150                 155                 160

Val Ala Ser Ala His Pro Ala Ile Gly Ala Phe Leu Gln Gln Pro Asp
                165                 170                 175

Ala Thr His Leu Ser Gln Leu Phe Ala Ser Leu Leu Asn Met Gln Gly
            180                 185                 190

Glu Glu Lys Ala Lys Ala Leu Gln Val Leu Arg Asp Val Leu Ala Arg
        195                 200                 205

Glu Gln Gly Glu Pro Trp Gln Thr Ile Arg Leu Ile Ala Glu Phe Tyr
    210                 215                 220

Pro Asp Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Gly Glu Leu Leu Thr Gln
    290                 295                 300

Pro Gln Gln His Gly Ala Glu Leu Asp Phe Pro Ile Pro Val Glu Asp
305                 310                 315                 320

Phe Ala Phe Ser Leu His Asp Leu Ser Ala Glu Ala Ser Asp Leu Ala
                325                 330                 335

Gln Ala Ser Ala Ala Ile Ile Phe Cys Val Asp Gly Glu Ala Val Leu
            340                 345                 350

His Lys Gly Asp Gln Ser Leu Thr Leu Lys Pro Gly Glu Ser Ala Phe
        355                 360                 365

Val Ala Ala Asn Glu Ser Pro Val Gln Val Ser Gly Arg Gly Arg Val
    370                 375                 380

Ala Arg Val Phe Asn Lys Leu Gln
385                 390

<210> SEQ ID NO 39
<211> LENGTH: 304
<212> TYPE: PRT
<213> ORGANISM: Klebsiella pneumoniae

<400> SEQUENCE: 39

Met Arg Ile Gly Ile Asp Leu Gly Gly Thr Lys Thr Glu Val Ile Ala
1               5                   10                  15

Leu Ser Asp Gln Gly Glu Gln Leu Phe Arg His Arg Leu Pro Thr Pro
            20                  25                  30

Arg Glu Asp Tyr Arg Gln Thr Ile Glu Thr Ile Ala Thr Leu Val Ala
        35                  40                  45

Met Ala Glu Gln Ala Thr Gly Gln Gln Gly Thr Val Gly Met Gly Ile
    50                  55                  60

Pro Gly Ala Ile Ser Pro Tyr Thr Gly Val Val Lys Asn Ala Asn Ser
65                  70                  75                  80

Thr Trp Leu Asn Gly Gln Pro Phe Asp Lys Asp Leu Ser Leu Arg Leu
                85                  90                  95
```

```
Glu Arg Glu Val Arg Leu Ala Asn Asp Ala Asn Cys Leu Ala Val Ser
            100                 105                 110

Glu Ala Val Asp Gly Ala Ala Gly Ala Gln Thr Val Phe Ala Val
            115                 120                 125

Ile Ile Gly Thr Gly Cys Gly Ala Gly Val Ala Leu Asn Gly Arg Ala
            130                 135                 140

His Ile Gly Gly Asn Gly Asn Ala Gly Glu Trp Gly His Asn Pro Leu
145                 150                 155                 160

Pro Trp Met Asn Asp Asp Glu Leu Arg Tyr Arg Ala Glu Val Pro Cys
                165                 170                 175

Tyr Cys Gly Lys Gln Gly Cys Ile Glu Thr Phe Ile Ser Gly Thr Gly
            180                 185                 190

Phe Ala Thr Asp Tyr Gln Arg Leu Ser Gly Lys Gly Leu Thr Gly Ser
            195                 200                 205

Glu Ile Met Arg Leu Val Gly Glu Gly Asp Glu Lys Ala Glu Leu Ala
            210                 215                 220

Leu Ser Arg Tyr Glu Gln Arg Leu Ala Lys Ser Leu Ala His Val Val
225                 230                 235                 240

Asn Ile Leu Asp Pro Asp Val Ile Val Leu Gly Gly Gly Met Ser Asn
                245                 250                 255

Val Glu Arg Leu Tyr Gln Thr Val Pro Asp Leu Val Lys Gln Trp Val
            260                 265                 270

Phe Gly Gly Glu Cys Glu Thr Pro Ile Arg Lys Ala Leu His Gly Asp
            275                 280                 285

Ser Ser Gly Val Arg Gly Ala Ala Trp Leu Trp Pro Leu Gln Gly Thr
290                 295                 300

<210> SEQ ID NO 40
<211> LENGTH: 392
<212> TYPE: PRT
<213> ORGANISM: Serratia odorifera

<400> SEQUENCE: 40

Met Gln Lys Met Thr Asn Ala Val Gln Asn Tyr Ala Trp Gly Ser His
1               5                   10                  15

Glu Ala Leu Thr Lys Leu Tyr Gly Ile Ala Asn Pro Gln Gly Lys Pro
                20                  25                  30

Met Ala Glu Leu Trp Met Gly Ala His Pro Lys Ser Ser Ser Gln Val
            35                  40                  45

Pro Asp Ala Asn Gly Asp Leu Arg Ser Leu Arg Asp Val Ile Asn Gln
50                  55                  60

Asp Gln Pro Lys Gln Leu Gly Gln Asp Val Ala Thr Arg Phe Gly Glu
65                  70                  75                  80

Leu Pro Phe Leu Phe Lys Val Leu Cys Ala Asp Gln Pro Leu Ser Ile
                85                  90                  95

Gln Val His Pro Ser Lys Ser Ala Ala Glu Val Gly Tyr Ala Arg Glu
            100                 105                 110

Asn Ala Ala Gly Ile Pro Leu Asp Ala Ala Glu Arg Asn Tyr Lys Asp
            115                 120                 125

Pro Asn His Lys Pro Glu Leu Val Phe Ala Leu Thr Pro Phe Leu Ala
            130                 135                 140

Met Asn Gly Phe Arg Glu Leu Ala Asp Ile Val Ala Leu Leu Gln Pro
145                 150                 155                 160

Ile Ala Gly Ala His His Asp Ile Ala Ala Phe Leu Gln Gln Pro Asp
                165                 170                 175
```

```
Thr Glu Arg Leu Ala Lys Leu Phe Ala Ser Leu Leu Gly Met Ser Gly
            180                 185                 190

Glu Gln Lys Ser Leu Ala Leu Gly Val Leu Lys Ala Ala Leu Asn Asn
        195                 200                 205

Gln Gln Gly Glu Pro Trp Asp Thr Val Arg Phe Ile Ala Gly Phe Tyr
    210                 215                 220

Pro Glu Asp Ser Gly Leu Phe Ser Pro Leu Leu Asn Val Val Lys
225                 230                 235                 240

Leu Ala Pro Gly Glu Ala Met Phe Leu Tyr Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Phe Ile Asp Ile Pro Glu Leu Leu
        275                 280                 285

Ala Asn Leu Gln Phe Arg Pro Gln Pro Ala Ser Gly Leu Leu Thr Gln
    290                 295                 300

Pro Glu Lys Arg Gly Asp Glu Leu Phe Phe Pro Ile Pro Val Glu Asp
305                 310                 315                 320

Phe Ala Phe Ser Leu His Asp Leu Ser Ser Ala Gln Ser Leu Ala
                325                 330                 335

Gln Arg Ser Ala Ala Ile Val Phe Cys Val Glu Gly Glu Ala Arg Leu
            340                 345                 350

Glu Lys Gln Gly Gln Gln Ile Thr Leu His Pro Gly Glu Ser Cys Phe
        355                 360                 365

Ile Gly Ala Phe Glu Ser Pro Val Ser Val Ser Gly Gly Arg Ile
    370                 375                 380

Ala Arg Val Tyr Asn Gln Leu Ser
385                 390

<210> SEQ ID NO 41
<211> LENGTH: 491
<212> TYPE: PRT
<213> ORGANISM: Escherichia fergusonii

<400> SEQUENCE: 41

Met Ser Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln Asn Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Ala Leu Gly Gly Tyr Cys Ser Asn
65                  70                  75                  80

Arg Phe Gly Arg Arg Asp Ser Leu Lys Ile Ala Ala Val Leu Phe Phe
                85                  90                  95

Ile Ser Gly Val Gly Ser Ala Trp Pro Glu Leu Gly Phe Thr Ser Ile
            100                 105                 110

Asn Pro Asp Asn Thr Val Pro Val Tyr Leu Ala Gly Tyr Val Pro Glu
        115                 120                 125

Phe Val Ile Tyr Arg Ile Gly Gly Ile Gly Val Gly Leu Ala Ser
    130                 135                 140

Met Leu Ser Pro Met Tyr Ile Ala Glu Leu Ala Pro Ala His Ile Arg
```

```
            145                 150                 155                 160
Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Thr
                180                 185                 190

Trp Leu Asn Thr Asp Gly Trp Arg Tyr Met Phe Ala Ser Glu Cys Ile
                195                 200                 205

Pro Ala Leu Leu Phe Leu Met Leu Leu Tyr Thr Val Pro Glu Ser Pro
            210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Arg Leu Leu Met
                260                 265                 270

Phe Gly Val Gly Val Ile Val Ile Gly Val Met Leu Ser Ile Phe Gln
                275                 280                 285

Gln Phe Val Gly Ile Asn Val Val Leu Tyr Tyr Ala Pro Glu Val Phe
            290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335

Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Pro
                355                 360                 365

Gly Ile Val Ala Leu Leu Ser Met Leu Phe Tyr Val Ala Ala Phe Ala
                370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
                420                 425                 430

Ser Trp Leu Val Ala His Phe His Asn Gly Phe Ser Tyr Trp Ile Tyr
                435                 440                 445

Gly Cys Met Gly Val Leu Ala Ala Leu Phe Met Trp Lys Phe Val Pro
            450                 455                 460

Glu Thr Lys Gly Lys Thr Leu Glu Glu Leu Glu Ala Leu Trp Glu Pro
465                 470                 475                 480

Glu Thr Lys Lys Thr Gln Gln Thr Ala Thr Leu
                485                 490

<210> SEQ ID NO 42
<211> LENGTH: 490
<212> TYPE: PRT
<213> ORGANISM: Shigella flexneri

<400> SEQUENCE: 42

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
                20                  25                  30
```

```
Gly Thr Val Glu Ser Leu Asn Thr Val Phe Val Ala Pro Gln Asn Leu
            35                  40                  45

Ser Glu Ser Ala Ala Asn Ser Leu Leu Gly Phe Cys Val Ala Ser Ala
 50                  55                  60

Leu Ile Gly Cys Ile Ile Gly Ala Leu Gly Gly Tyr Cys Ser Asn
 65                  70                  75                  80

Arg Phe Gly Arg Arg Asp Ser Leu Lys Ile Ser Ala Val Leu Phe Phe
                 85                  90                  95

Ile Ser Gly Val Gly Ser Ala Trp Pro Glu Leu Gly Phe Thr Ser Ile
                100                 105                 110

Asn Pro Asp Asn Thr Val Pro Ile Tyr Leu Ala Gly Tyr Val Pro Glu
                115                 120                 125

Phe Val Ile Tyr Arg Ile Ile Gly Gly Ile Gly Val Gly Leu Ala Ser
        130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
                180                 185                 190

Trp Leu Asn Thr Asp Gly Arg Arg Tyr Met Phe Ala Ser Glu Cys Ile
        195                 200                 205

Pro Ala Leu Leu Phe Leu Met Leu Leu Tyr Thr Val Pro Glu Ser Pro
        210                 215                 220

Arg Trp Leu Met Ser Arg Gly Lys Gln Glu Gln Thr Glu Ser Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
                260                 265                 270

Phe Gly Val Gly Val Ile Val Ile Gly Val Met Leu Ser Ile Phe Gln
        275                 280                 285

Gln Phe Val Gly Ile Asn Val Val Leu Tyr Tyr Ala Pro Glu Val Phe
        290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335

Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Ser
                355                 360                 365

Gly Ile Val Ala Leu Leu Ser Met Leu Phe Tyr Val Ala Ala Phe Ala
        370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
                420                 425                 430

Ser Trp Leu Val Ala His Phe His Asn Gly Phe Ser Tyr Trp Ile Tyr
                435                 440                 445

Gly Cys Met Gly Val Leu Ala Ala Leu Phe Met Trp Lys Phe Val Pro
```

```
                450                 455                 460
Glu Thr Lys Gly Lys Thr Leu Glu Leu Glu Ala Leu Trp Glu Pro
465                 470                 475                 480

Glu Thr Lys Lys Thr Gln Gln Thr Ala Thr
                485                 490

<210> SEQ ID NO 43
<211> LENGTH: 491
<212> TYPE: PRT
<213> ORGANISM: Salmonella enterica

<400> SEQUENCE: 43

Met Asn Thr His Tyr Asn Ser Arg Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln His Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Gly Tyr Cys Ser Asn
65                  70                  75                  80

Arg Phe Gly Arg Arg Asp Ser Leu Lys Ile Ala Ala Leu Leu Phe Phe
                85                  90                  95

Ile Ser Gly Ile Gly Ser Ala Trp Pro Glu Leu Gly Phe Thr Thr Ile
            100                 105                 110

Asn Pro Asp Asn Ala Val Pro Val Tyr Leu Ala Gly Tyr Val Pro Glu
        115                 120                 125

Phe Val Ile Tyr Arg Ile Gly Gly Ile Gly Val Gly Leu Ala Ser
    130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Asn
            180                 185                 190

Trp Leu Asn Thr Asp Gly Trp Arg Tyr Met Phe Ala Ser Glu Ser Ile
        195                 200                 205

Pro Ala Leu Leu Phe Leu Leu Leu Tyr Thr Val Pro Glu Ser Pro
    210                 215                 220

Arg Trp Leu Met Ala Arg Gly Lys His Glu Gln Ala Glu Gly Ile Leu
225                 230                 235                 240

Arg Lys Ile Met Gly Ser Ser Leu Thr Thr Gln Ala Met Gln Glu Ile
                245                 250                 255

Asn Gln Ser Leu Glu His Gly Arg Lys Thr Gly Gly Arg Leu Leu Met
            260                 265                 270

Phe Gly Val Gly Val Ile Val Ile Gly Val Met Leu Ser Val Phe Gln
        275                 280                 285

Gln Phe Val Gly Ile Asn Val Val Leu Tyr Tyr Ala Pro Glu Val Phe
    290                 295                 300

Lys Thr Leu Gly Ala Ser Thr Asp Val Ala Leu Leu Gln Thr Ile Ile
305                 310                 315                 320

Val Gly Val Ile Asn Leu Ser Phe Thr Val Leu Ala Ile Met Thr Val
                325                 330                 335
```

-continued

```
Asp Lys Phe Gly Arg Lys Pro Leu Gln Ile Ile Gly Ala Leu Gly Met
            340                 345                 350

Ala Leu Gly Met Phe Ser Leu Gly Thr Ala Phe Tyr Thr Gln Ala Ser
        355                 360                 365

Gly Leu Ile Ala Leu Leu Ser Met Leu Phe Tyr Val Ala Ala Phe Ala
    370                 375                 380

Met Ser Trp Gly Pro Val Cys Trp Val Leu Ala Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Thr Phe Pro Met Met Asp Lys Asn
        420                 425                 430

Ser Trp Leu Val Ser His Phe His Asn Gly Phe Ser Tyr Trp Ile Tyr
        435                 440                 445

Gly Cys Met Gly Ile Leu Ala Ala Leu Phe Met Trp Lys Phe Val Pro
    450                 455                 460

Glu Thr Lys Gly Lys Thr Leu Glu Glu Leu Lys Leu Trp Thr Pro
465                 470                 475                 480

Ala Glu Glu Lys Thr Pro Lys Ala Ala Ile Gln
                485                 490
```

<210> SEQ ID NO 44
<211> LENGTH: 491
<212> TYPE: PRT
<213> ORGANISM: Citrobacter youngae

<400> SEQUENCE: 44

```
Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln His Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Gly Tyr Cys Ser Asn
65                  70                  75                  80

Arg Phe Gly Arg Arg Asp Ser Leu Lys Ile Ala Ala Leu Leu Phe Phe
                85                  90                  95

Ile Ser Gly Ile Gly Ser Ala Trp Pro Glu Leu Gly Phe Thr Thr Ile
            100                 105                 110

Asn Pro Asp Asn Ala Val Pro Val Tyr Leu Ala Gly Tyr Val Pro Glu
        115                 120                 125

Phe Val Ile Tyr Arg Ile Ile Gly Gly Ile Gly Val Gly Leu Ala Ser
    130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Asn
            180                 185                 190

Trp Leu Asn Thr Asp Gly Trp Arg Tyr Met Phe Ala Ser Glu Ser Ile
        195                 200                 205

Pro Ala Leu Leu Phe Leu Leu Leu Leu Tyr Thr Val Pro Glu Ser Pro
    210                 215                 220
```

```
Arg Trp Leu Met Ala Arg Gly Lys His Glu Gln Ala Glu Gly Ile Leu
225                 230                 235                 240

Arg Lys Ile Met Gly Asn Ser Leu Ala Thr Gln Ala Met Gln Glu Ile
            245                 250                 255

Asn Gln Ser Leu Glu His Gly Arg Lys Thr Gly Gly Arg Leu Leu Met
        260                 265                 270

Phe Gly Val Gly Val Ile Val Ile Gly Val Met Leu Ser Ile Phe Gln
    275                 280                 285

Gln Phe Val Gly Ile Asn Val Val Leu Tyr Tyr Ala Pro Glu Val Phe
    290                 295                 300

Lys Thr Leu Gly Ala Ser Thr Asp Val Ala Leu Leu Gln Thr Ile Ile
305                 310                 315                 320

Val Gly Val Ile Asn Leu Ser Phe Thr Val Leu Ala Ile Met Thr Val
            325                 330                 335

Asp Lys Phe Gly Arg Lys Pro Leu Gln Ile Ile Gly Ala Leu Gly Met
        340                 345                 350

Ala Leu Gly Met Phe Ser Leu Gly Thr Ala Phe Tyr Thr Gln Ala Ser
    355                 360                 365

Gly Leu Ile Ala Leu Leu Ser Met Leu Phe Tyr Val Ala Ala Phe Ala
    370                 375                 380

Met Ser Trp Gly Pro Val Cys Trp Val Leu Ala Glu Ile Phe Pro
385                 390                 395                 400

Asn Ala Ile Arg Gly Lys Ala Leu Ala Ile Ala Val Ala Ala Gln Trp
            405                 410                 415

Leu Ala Asn Tyr Phe Val Ser Trp Thr Phe Pro Met Met Asp Lys Asn
        420                 425                 430

Ser Trp Leu Val Ser His Phe His Asn Gly Phe Ser Tyr Trp Ile Tyr
    435                 440                 445

Gly Cys Met Gly Ile Leu Ala Ala Leu Phe Met Trp Lys Phe Val Pro
    450                 455                 460

Glu Thr Lys Gly Lys Thr Leu Glu Glu Leu Glu Glu Leu Trp Glu Pro
465                 470                 475                 480

Ala Ala Glu Lys Ala Lys Pro Ala Ser Ala Gln
                485                 490

<210> SEQ ID NO 45
<211> LENGTH: 484
<212> TYPE: PRT
<213> ORGANISM: Acidobacterium capsulatum

<400> SEQUENCE: 45

Met Ala Arg Leu Asn Lys Tyr Val Val Phe Leu Ala Leu Ile Ala Thr
1               5                   10                  15

Phe Gly Gly Leu Leu Phe Gly Tyr Asp Thr Ala Val Ile Asn Gly Ala
            20                  25                  30

Val Asp Ser Leu Lys Ala Tyr Phe Ile Asn Pro Arg Phe Ser Asp Leu
        35                  40                  45

Ala Asn Pro Ala Gln Ala Asp Ala Ala Ser Leu Leu Gly Phe Val
    50                  55                  60

Val Ser Ser Ala Leu Ile Gly Cys Ile Ile Gly Leu Met Gly Gly
65                  70                  75                  80

Trp Val Ser Thr Val Ile Gly Arg Lys Arg Gly Leu Val Ile Ala Ala
                85                  90                  95

Val Leu Phe Leu Ile Ser Ala Leu Gly Ala Ser Ala Pro Glu Phe Pro
```

```
            100                 105                 110
Phe Ala Pro Ile Gly His Gly Gly Pro Ala Tyr Met Trp Asn Phe Val
            115                 120                 125
Ile Tyr Arg Ile Leu Gly Gly Ile Gly Val Gly Leu Ala Ser Met Leu
            130                 135             140
Ser Pro Met Tyr Ile Ala Glu Ile Ala Pro Lys Val Arg Gly Asn
145                 150                 155                 160
Leu Val Ala Trp Asn Gln Phe Ala Ile Ile Phe Gly Met Leu Val Ile
                165                 170                 175
Tyr Phe Val Asn Tyr Gly Ile Ser Lys Gly Gly Asn Gly Asp Ala Trp
                180                 185                 190
Leu Asn Ser Ile Gly Trp Arg Tyr Met Phe Leu Ser Gly Ala Ile Pro
            195                 200                 205
Ala Ser Ile Phe Leu Leu Leu Leu Phe Val Pro Glu Thr Pro Arg
            210                 215                 220
Tyr Leu Met Met Lys Gly Gln Glu Ala Lys Ala Arg Thr Val Leu Asp
225                 230                 235                 240
Lys Leu Val Thr Lys Glu Glu Ala Asp Arg Glu Leu Arg Glu Ile Arg
                245                 250                 255
Ala Ser Leu Ser Gln Asn His Ser Gly Lys Leu Phe Ser Phe Gly Ala
                260                 265                 270
Phe Leu Ile Phe Ser Gly Met Leu Leu Ser Ile Phe Gln Gln Phe Val
            275                 280                 285
Gly Ile Asn Val Val Leu Tyr Tyr Ala Thr Asp Ile Phe Lys Gly Met
            290                 295                 300
Gly Met Ser Thr Asn Ala Ala Leu Met Gln Thr Ile Ile Val Gly Ala
305                 310                 315                 320
Val Asn Leu Thr Phe Thr Val Ile Ala Ile Leu Thr Val Asp Arg Phe
                325                 330                 335
Gly Arg Arg Pro Leu Gln Val Val Gly Gly Leu Ile Met Ala Ala Ser
                340                 345                 350
Met Thr Trp Leu Gly Ile Glu Leu Trp Thr Gly Gly Lys Gly Leu Gly
            355                 360                 365
Ala Leu Ile Ala Met Leu Val Tyr Thr Ala Gly Phe Ala Val Ser Trp
            370                 375                 380
Gly Pro Val Thr Trp Val Leu Leu Ser Glu Ile Phe Pro Asn Gln Ile
385                 390                 395                 400
Arg Gly Lys Ala Met Ala Ile Ala Val Ala Val Gln Trp Val Ala Asn
                405                 410                 415
Tyr Leu Val Ser Trp Thr Phe Pro Ile Leu Asn Asn Asn Pro Phe Leu
                420                 425                 430
Val Lys His Phe His His Gly Phe Ala Tyr Trp Ile Tyr Gly Val Met
            435                 440                 445
Ser Ile Leu Ala Ala Leu Phe Val Trp Arg Lys Val Pro Glu Thr Lys
            450                 455                 460
Gly Arg Thr Leu Glu Gln Met Glu Ser Leu Trp Gly Ser Leu Lys Lys
465                 470                 475                 480
Ala Ala Ile Gly

<210> SEQ ID NO 46
<211> LENGTH: 484
<212> TYPE: PRT
<213> ORGANISM: Shigella flexneri
```

```
<400> SEQUENCE: 46

Met Tyr Ile Gly Ile Asp Leu Gly Thr Ser Gly Val Lys Val Ile Leu
1               5                   10                  15

Leu Asn Glu Gln Gly Glu Val Val Ala Ser Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
    210                 215                 220

Val Pro Val Val Ala Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285

Ser Val Met Leu Ser Ala Ala Ser Cys Leu Asp Trp Ala Ala Lys Leu
    290                 295                 300

Thr Gly Leu Cys Asn Val Pro Ala Leu Ile Ala Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
        355                 360                 365

Val Gly Tyr Ala Leu Ala Asp Gly Met Asp Val His Ala Cys Gly
    370                 375                 380

Ile Lys Pro Gln Ser Val Thr Leu Ile Gly Gly Gly Ala Arg Ser Glu
385                 390                 395                 400

Tyr Trp Arg Gln Met Leu Ala Asp Ile Ser Gly Gln Gln Leu Asp Tyr
                405                 410                 415
```

```
Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
            435                 440                 445

Leu Pro Leu Glu Gln Ser His Leu Pro Asp Ala Gln Arg Tyr Ala Ala
450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 47
<211> LENGTH: 484
<212> TYPE: PRT
<213> ORGANISM: Citrobacter rodentium

<400> SEQUENCE: 47

Met Tyr Ile Gly Ile Asp Leu Gly Thr Ser Gly Val Lys Ala Ile Leu
1               5                   10                  15

Leu Asn Glu Gln Gly Glu Val Ala Ala Gln Thr Glu Lys Leu Thr
            20                  25                  30

Val Ser Arg Pro His Pro Leu Trp Ser Glu Gln Asp Pro Glu Gln Trp
            35                  40                  45

Trp Leu Ala Thr Asp Arg Ala Val Lys Ala Leu Gly Lys Gln His Ser
    50                  55                  60

Leu Ser Glu Val Lys Ala Leu Gly Ile Ala Gly Gln Met His Gly Ala
65                  70                  75                  80

Thr Leu Leu Asp Asp Gln Gln Arg Val Leu Arg Pro Ala Ile Leu Trp
                85                  90                  95

Asn Asp Gly Arg Cys Gly Glu Glu Cys Ala Leu Leu Glu Ala Gln Ala
            100                 105                 110

Pro Gln Ser Arg Ala Ile Thr Gly Asn Leu Met Met Pro Gly Phe Thr
            115                 120                 125

Ala Pro Lys Leu Leu Trp Val Lys Cys His Glu Pro Glu Ile Phe Arg
130                 135                 140

Gln Val Ala Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Glu Lys Arg Asp Trp Ser Asp Val Met Leu Glu Ala Cys
            180                 185                 190

Gly Leu Thr Arg Asp His Met Pro Ala Leu Phe Glu Gly Ser Asp Ile
            195                 200                 205

Ser Gly Thr Leu Leu Pro Glu Ile Ala Thr Ala Trp Gly Met Pro Ala
    210                 215                 220

Ala Pro Val Val Ala Gly Gly Asp Asn Ala Ala Gly Ala Val Gly
225                 230                 235                 240

Val Gly Met Ile Asp Ala Asn Gln Ala Met Leu Ser Leu Gly Thr Ser
                245                 250                 255

Gly Val Tyr Phe Ala Val Ser Asp Gly Phe Leu Ser Lys Pro Glu Ser
            260                 265                 270

Ala Val His Ser Phe Cys His Ala Leu Pro Gly Arg Trp His Leu Met
            275                 280                 285

Ser Val Met Leu Ser Ala Ala Ser Cys Leu Asp Trp Ala Ala Lys Leu
    290                 295                 300
```

```
Thr Gly Leu Glu Thr Val Pro Ala Leu Leu Asp Ala Ala Gln Thr Ala
305                 310                 315                 320

Asp Thr Ser Ala Asp Pro Val Trp Phe Leu Pro Tyr Leu Ser Gly Glu
            325                 330                 335

Arg Thr Pro His Asn Asn Pro Gln Ala Lys Gly Val Phe Phe Gly Leu
            340                 345                 350

Thr His Gln His Gly Pro Ala Glu Leu Ala Arg Ala Val Leu Glu Gly
            355                 360                 365

Val Gly Tyr Ala Leu Ala Asp Gly Met Asp Val Val His Ala Cys Gly
        370                 375                 380

Val Lys Pro Gln Ser Ile Thr Leu Ile Gly Gly Ala Arg Ser Ala
385                 390                 395                 400

Tyr Trp Arg Gln Met Leu Ala Asp Ile Ser Gly Leu Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Met Asn Pro Glu Lys Pro Leu Ser Asp Leu Leu Pro Gln
            435                 440                 445

Leu Pro Leu Glu Gln Thr His Arg Pro Asp Ala Gln Arg His Ala Asp
    450                 455                 460

Tyr Gln Gln Arg Arg Glu Thr Phe Arg Arg Leu Tyr Gln Gln Leu Leu
465                 470                 475                 480

Pro Leu Met Ser

<210> SEQ ID NO 48
<211> LENGTH: 356
<212> TYPE: PRT
<213> ORGANISM: Shigella flexneri

<400> SEQUENCE: 48

Met Leu Lys Ile Gly Tyr Val Tyr Arg Gly Asp Cys Tyr Leu Leu Lys
1               5                   10                  15

Leu Ser Ser Asn Tyr Arg Arg Pro Tyr Thr Met Lys Ile Lys Asn Ile
            20                  25                  30

Leu Leu Thr Leu Cys Thr Ser Leu Leu Leu Thr Asn Val Ala Ala His
        35                  40                  45

Ala Lys Glu Val Lys Ile Gly Met Ala Ile Asp Asp Leu Arg Leu Glu
    50                  55                  60

Arg Trp Gln Lys Asp Arg Asp Ile Phe Val Lys Lys Ala Glu Ser Leu
65                  70                  75                  80

Gly Ala Lys Val Phe Val Gln Ser Ala Asn Gly Asn Glu Glu Thr Gln
                85                  90                  95

Met Ser Gln Ile Glu Asn Met Ile Asn Arg Gly Val Asp Val Leu Val
            100                 105                 110

Ile Ile Pro Tyr Asn Gly Gln Val Leu Ser Asn Val Val Lys Glu Ala
        115                 120                 125

Lys Gln Glu Gly Ile Lys Val Leu Ala Tyr Asp Arg Met Ile Asn Asp
    130                 135                 140

Ala Asp Ile Asp Phe Tyr Ile Ser Phe Asp Asn Glu Lys Val Gly Glu
145                 150                 155                 160

Leu Gln Ala Lys Ala Leu Val Asp Ile Val Pro Gln Gly Asn Tyr Phe
                165                 170                 175

Leu Met Gly Gly Ser Pro Val Asp Asn Asn Ala Lys Leu Phe Arg Ala
            180                 185                 190
```

```
Gly Gln Met Lys Val Leu Lys Pro Tyr Val Asp Ser Gly Lys Ile Lys
            195                 200                 205
Val Val Gly Asp Gln Trp Val Asp Gly Trp Leu Pro Glu Asn Ala Leu
210                 215                 220
Lys Ile Met Glu Asn Ala Leu Thr Ala Asn Asn Lys Ile Asp Ala
225                 230                 235                 240
Val Val Ala Ser Asn Asp Ala Thr Ala Gly Ala Ile Gln Ala Leu
            245                 250                 255
Ser Ala Gln Gly Leu Ser Gly Lys Val Ala Ile Ser Gly Gln Asp Ala
            260                 265                 270
Asp Leu Ala Gly Ile Lys Arg Ile Ala Ala Gly Thr Gln Thr Met Thr
            275                 280                 285
Val Tyr Lys Pro Ile Thr Leu Leu Ala Asn Thr Ala Ala Glu Ile Ala
            290                 295                 300
Val Glu Leu Gly Asn Gly Gln Glu Pro Lys Ala Asp Thr Ser Leu Asn
305                 310                 315                 320
Asn Gly Leu Lys Asp Val Pro Ser Arg Leu Thr Pro Ile Asp Val
            325                 330                 335
Asn Lys Asn Asn Ile Lys Asp Thr Val Ile Lys Asp Gly Phe His Lys
            340                 345                 350
Glu Ser Glu Leu
        355

<210> SEQ ID NO 49
<211> LENGTH: 330
<212> TYPE: PRT
<213> ORGANISM: Citrobacter koseri

<400> SEQUENCE: 49

Met Lys Ile Lys Asn Ile Leu Leu Thr Val Cys Thr Ser Leu Leu Leu
1               5                   10                  15
Thr Ser Ile Thr Gly His Ala Lys Glu Val Lys Ile Gly Met Ala Ile
            20                  25                  30
Asp Asp Leu Arg Leu Glu Arg Trp Gln Lys Asp Arg Asp Ile Phe Val
            35                  40                  45
Ser Lys Ala Glu Ser Leu Gly Ala Lys Val Phe Val Gln Ser Ala Asn
50                  55                  60
Gly Asn Glu Glu Thr Gln Met Ser Gln Ile Glu Asn Met Ile Asn Arg
65                  70                  75                  80
Gly Val Asp Val Leu Val Ile Ile Pro Tyr Asn Gly Gln Val Leu Ser
            85                  90                  95
Asn Val Val Lys Glu Ala Lys Gln Glu Gly Ile Lys Val Leu Ala Tyr
            100                 105                 110
Asp Arg Met Ile Asn Asp Ala Asp Ile Asp Phe Tyr Ile Ser Phe Asp
            115                 120                 125
Asn Glu Lys Val Gly Glu Leu Gln Ala Gln Ala Leu Val Asp Lys Val
            130                 135                 140
Pro Glu Gly Asn Tyr Phe Leu Met Gly Gly Ser Pro Val Asp Asn Asn
145                 150                 155                 160
Ala Lys Leu Phe Arg Ala Gly Gln Met Lys Val Leu Lys Pro Tyr Ile
            165                 170                 175
Asp Ser Gly Lys Ile Asn Val Val Gly Asp Gln Trp Val Asp Gly Trp
            180                 185                 190
Leu Pro Glu Asn Ala Leu Lys Ile Met Glu Asn Ala Leu Thr Ala Asn
```

```
                195                 200                 205
Asn Asn Lys Ile Asp Ala Val Ala Ser Asn Asp Ala Thr Ala Gly
    210                 215                 220
Gly Ala Ile Gln Ala Leu Ser Ala Gln Gly Leu Ser Gly Lys Val Ala
225                 230                 235                 240
Ile Ser Gly Gln Asp Ala Asp Leu Ala Gly Ile Lys Arg Ile Val Ala
                245                 250                 255
Gly Thr Gln Thr Met Thr Val Tyr Lys Pro Ile Thr Leu Leu Ala Asn
            260                 265                 270
Thr Ala Ala Glu Ile Ala Val Glu Leu Gly Asn Gly Gln Gln Pro Lys
            275                 280                 285
Ala Asp Ala Thr Leu Asn Asn Gly Leu Lys Asp Val Pro Ser Arg Leu
        290                 295                 300
Leu Thr Pro Ile Asp Val Asn Lys Thr Asn Ile Asp Glu Thr Val Ile
305                 310                 315                 320
Lys Asp Gly Phe His Lys Lys Ser Asp Leu
                325                 330

<210> SEQ ID NO 50
<211> LENGTH: 513
<212> TYPE: PRT
<213> ORGANISM: Shigella boydii

<400> SEQUENCE: 50

Met Pro Tyr Leu Leu Glu Met Lys Asn Ile Thr Lys Thr Phe Gly Ser
1               5                   10                  15
Val Lys Ala Ile Asp Asn Val Ser Leu Arg Leu Asn Ala Gly Glu Ile
                20                  25                  30
Val Ser Leu Cys Gly Glu Asn Gly Ser Gly Lys Ser Thr Leu Met Lys
            35                  40                  45
Val Leu Cys Gly Ile Tyr Pro His Gly Ser Tyr Glu Gly Glu Ile Ile
    50                  55                  60
Phe Ala Gly Glu Glu Ile Gln Ala Ser His Ile Arg Asp Thr Glu Arg
65              70                  75                  80
Lys Gly Ile Ala Ile Ile His Gln Glu Leu Ala Leu Val Lys Glu Leu
                85                  90                  95
Thr Val Leu Glu Asn Ile Phe Leu Gly Asn Glu Ile Thr His Asn Gly
                100                 105                 110
Ile Met Asp Tyr Asp Leu Met Thr Leu Arg Cys Gln Lys Leu Leu Ala
            115                 120                 125
Gln Val Ser Leu Ser Ile Ser Pro Asp Thr Arg Val Gly Asp Leu Gly
        130                 135                 140
Leu Gly Gln Gln Gln Leu Val Glu Ile Ala Lys Ala Leu Asn Lys Gln
145                 150                 155                 160
Val Arg Leu Leu Ile Leu Asp Glu Pro Thr Ala Ser Leu Thr Glu Gln
                165                 170                 175
Glu Thr Ser Val Leu Leu Asp Ile Ile Arg Asp Leu Gln Gln His Gly
            180                 185                 190
Ile Ala Cys Ile Tyr Ile Ser His Lys Leu Asn Glu Val Lys Ala Ile
        195                 200                 205
Ser Asp Thr Ile Cys Val Ile Arg Asp Gly Gln His Ile Gly Thr Arg
    210                 215                 220
Asp Ala Ala Gly Met Ser Glu Asp Asp Ile Ile Thr Met Met Val Gly
225                 230                 235                 240
```

```
Arg Glu Leu Thr Ala Leu Tyr Pro Asn Glu Pro His Thr Thr Gly Asp
            245                 250                 255

Glu Ile Leu Arg Ile Glu His Leu Thr Ala Trp His Pro Val Asn Arg
        260                 265                 270

His Ile Lys Arg Val Asn Asp Val Ser Phe Ser Leu Lys Arg Gly Glu
    275                 280                 285

Ile Leu Gly Ile Ala Gly Leu Val Gly Ala Gly Arg Thr Glu Thr Ile
290                 295                 300

Gln Cys Leu Phe Gly Val Trp Pro Gly Gln Trp Glu Gly Lys Ile Tyr
305                 310                 315                 320

Ile Asp Gly Lys Gln Val Asp Ile Arg Asn Cys Gln Gln Ala Ile Ala
                325                 330                 335

Gln Gly Ile Ala Met Val Pro Glu Asp Arg Lys Arg Asp Gly Ile Val
            340                 345                 350

Pro Val Met Ala Val Gly Lys Asn Ile Thr Leu Ala Ala Leu Asn Lys
        355                 360                 365

Phe Thr Gly Gly Ile Ser Gln Leu Asp Asp Ala Ala Glu Gln Lys Cys
    370                 375                 380

Ile Leu Glu Ser Ile Gln Gln Leu Lys Val Lys Thr Ser Ser Pro Asp
385                 390                 395                 400

Leu Ala Ile Gly Arg Leu Ser Gly Gly Asn Gln Gln Lys Ala Ile Leu
                405                 410                 415

Ala Arg Cys Leu Leu Asn Pro Arg Ile Leu Ile Leu Asp Glu Pro
            420                 425                 430

Thr Arg Gly Ile Asp Ile Gly Val Lys Tyr Glu Ile Tyr Lys Leu Ile
        435                 440                 445

Asn Gln Leu Val Gln Gln Gly Ile Ala Val Ile Val Ile Ser Ser Glu
    450                 455                 460

Leu Pro Glu Val Leu Gly Leu Ser Asp Arg Val Leu Val Met His Glu
465                 470                 475                 480

Gly Lys Leu Lys Ala Asn Leu Ile Asn His Asn Leu Thr Gln Glu Gln
                485                 490                 495

Val Met Glu Ala Ala Leu Arg Ser Glu His His Val Glu Lys Gln Ser
            500                 505                 510

Val

<210> SEQ ID NO 51
<211> LENGTH: 513
<212> TYPE: PRT
<213> ORGANISM: Klebsiella pneumoniae

<400> SEQUENCE: 51

Met Ala Trp Leu Leu Glu Met Lys Asn Ile Thr Lys Thr Phe Gly Ala
1               5                   10                  15

Val Lys Ala Val Asp Asn Val Ser Leu Arg Leu Asn Ala Gly Glu Val
            20                  25                  30

Val Ser Leu Cys Gly Glu Asn Gly Ser Gly Lys Ser Thr Leu Met Lys
        35                  40                  45

Val Leu Cys Gly Ile Tyr Pro His Gly Ser Tyr Glu Gly Glu Ile Ile
    50                  55                  60

Phe Ala Gly Glu Thr Leu Gln Ala Asn His Ile Arg Asp Thr Glu Arg
65                  70                  75                  80

Lys Gly Ile Ala Ile Ile His Gln Glu Leu Ala Leu Val Lys His Leu
                85                  90                  95
```

```
Thr Val Leu Glu Asn Ile Phe Leu Gly Ala Glu Ile Ser Arg His Gly
                100                 105                 110

Leu Leu Asp Tyr Glu Thr Met Thr Leu Arg Cys Gln Lys Leu Leu Ala
            115                 120                 125

Gln Val Asn Leu Pro Ile Ser Pro Asp Thr Arg Val Gly Asp Leu Gly
        130                 135                 140

Leu Gly Gln Gln Gln Leu Val Glu Ile Ala Lys Ala Leu Asn Lys Gln
145                 150                 155                 160

Val Arg Leu Leu Ile Leu Asp Glu Pro Thr Ala Ser Leu Thr Glu Gln
                165                 170                 175

Glu Thr Ala Thr Leu Leu Thr Ile Ile Arg Asp Leu Gln Asn His Gly
            180                 185                 190

Ile Ala Cys Ile Tyr Ile Ser His Lys Leu Asn Glu Val Lys Ala Ile
        195                 200                 205

Ser Asp Thr Ile Cys Val Ile Arg Asp Gly Gln His Ile Gly Thr Arg
210                 215                 220

Asp Ala Ser Gly Met Ser Glu Asp Ile Ile Thr Met Met Val Gly
225                 230                 235                 240

Arg Glu Leu Thr Ala Leu Tyr Pro Ser Glu Pro His Ala His Gly Glu
                245                 250                 255

Glu Ile Leu Arg Val Glu His Leu Thr Ala Trp His Pro Val Asn Arg
            260                 265                 270

His Ile Lys Arg Val Asn Asp Val Ser Phe Ser Leu Arg Arg Gly Glu
        275                 280                 285

Ile Leu Gly Ile Ala Gly Leu Val Gly Ala Gly Arg Thr Glu Ala Val
290                 295                 300

Gln Cys Leu Phe Gly Val Trp Pro Gly Arg Trp Gln Gly Glu Ile Phe
305                 310                 315                 320

Ile Asp Gly Gln Pro Val Ser Ile Ser Asn Cys Gln Ala Ile Ala
                325                 330                 335

His Gly Ile Ala Met Val Pro Glu Asp Arg Lys Lys Asp Gly Ile Val
            340                 345                 350

Pro Val Met Ala Val Gly Lys Asn Ile Thr Leu Ala Ala Leu Asn Gln
        355                 360                 365

Phe Thr Gly Ala Met Ser Ser Leu Asp Asp Ala Ala Glu Gln His Cys
370                 375                 380

Ile Gln Gln Ser Ile Gln Arg Leu Lys Ile Lys Thr Ser Ser Pro Glu
385                 390                 395                 400

Leu Ala Ile Gly Arg Leu Ser Gly Gly Asn Gln Gln Lys Ala Ile Leu
                405                 410                 415

Ala Arg Cys Leu Leu Leu Asn Pro Arg Ile Leu Ile Leu Asp Glu Pro
            420                 425                 430

Thr Arg Gly Ile Asp Ile Gly Ala Lys Tyr Glu Ile Tyr Lys Leu Ile
        435                 440                 445

Asn Gln Leu Val Gln Gln Gly Ile Ala Val Ile Val Ile Ser Ser Glu
450                 455                 460

Leu Pro Glu Val Leu Gly Leu Ser Asp Arg Val Leu Val Met His Glu
465                 470                 475                 480

Gly Arg Leu Lys Ala Asn Leu Val Asn Gln His Leu Thr Gln Glu Gln
                485                 490                 495

Val Met Glu Ala Ala Leu Arg Ser Glu Arg His Val Glu Glu His Val
            500                 505                 510

Val
```

<210> SEQ ID NO 52
<211> LENGTH: 393
<212> TYPE: PRT
<213> ORGANISM: Citrobacter koseri

<400> SEQUENCE: 52

```
Met Ser Lys Asn Asn Pro Ser Glu Val Lys Leu Ser Ala Pro Leu Thr
1               5                   10                  15

Gly Gly Phe Pro Gly Leu Lys Ser Leu Asn Leu Gln Val Phe Val Met
                20                  25                  30

Ile Ala Ala Ile Ile Val Ile Met Leu Phe Phe Thr Trp Thr Thr Glu
            35                  40                  45

Gly Ala Tyr Leu Ser Ala Arg Asn Val Ser Asn Leu Leu Arg Gln Thr
        50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Cys Asp Val Trp Leu Gly Trp Pro Leu Pro Leu Thr
            100                 105                 110

Ile Val Val Thr Leu Ala Leu Gly Leu Leu Gly Ala Trp Asn Gly
            115                 120                 125

Trp Trp Val Ala Tyr Arg Lys Val Pro Ser Phe Ile Val Thr Leu Ala
130                 135                 140

Gly Met Leu Ala Phe Arg Gly Ile Leu Ile Gly Ile Thr Asn Gly Thr
145                 150                 155                 160

Thr Val Ser Pro Thr Ser Ser Ala Met Ser Gln Ile Gly Gln Ser Tyr
                165                 170                 175

Leu Ser Asn Gly Leu Gly Phe Thr Ile Gly Ala Ile Ser Leu Met Ala
            180                 185                 190

Phe Ile Gly Trp Gln Trp Arg Gly Arg Met Arg Arg Gln Ala Leu Ala
        195                 200                 205

Leu Ser Thr Pro Ala Ser Thr Ala Val Val Gly Arg Gln Ala Leu Thr
    210                 215                 220

Ala Val Ile Val Leu Gly Ala Ile Trp Leu Leu Asn Asp Tyr Arg Gly
225                 230                 235                 240

Val Pro Thr Pro Val Leu Leu Val Phe Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285

Lys Leu Ala Val Phe Ala Ile Asn Gly Leu Met Val Ala Ile Ala Gly
    290                 295                 300

Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335

Leu Ala Gly Gly Val Gly Ser Val Gly Ala Val Met Gly Ala Phe
            340                 345                 350

Ile Met Ala Ser Leu Asp Asn Gly Met Ser Met Met Asp Val Pro Thr
        355                 360                 365

Phe Trp Gln Tyr Ile Val Lys Gly Ala Ile Leu Leu Leu Ala Val Trp
```

```
            370                 375                 380
Met Asp Ser Ala Thr Lys Arg Arg Ser
385                 390

<210> SEQ ID NO 53
<211> LENGTH: 393
<212> TYPE: PRT
<213> ORGANISM: Shigella dysenteriae

<400> SEQUENCE: 53

Met Ser Lys Ser Asn Pro Ser Glu Val Lys Leu Ala Val Pro Thr Ser
1               5                   10                  15

Gly Gly Phe Ser Gly Leu Lys Ser Leu Asn Leu Gln Val Phe Val Met
            20                  25                  30

Ile Ala Ala Ile Ile Ala Ile Met Leu Phe Phe Thr Trp Thr Thr Asp
        35                  40                  45

Gly Ala Tyr Leu Ser Ala Arg Asn Val Ser Asn Leu Leu His Gln Thr
    50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Cys Asp Val Trp Leu Gly Trp Pro Leu Pro Leu Thr
            100                 105                 110

Ile Ile Val Thr Leu Val Leu Gly Leu Leu Gly Ala Trp Asn Gly
        115                 120                 125

Trp Trp Val Ala Tyr Arg Lys Val Pro Ser Phe Ile Val Thr Leu Ala
    130                 135                 140

Gly Met Leu Ala Phe Arg Gly Ile Leu Ile Gly Ile Thr Asn Gly Thr
145                 150                 155                 160

Thr Val Ser Pro Thr Ser Ala Ala Met Ser Gln Ile Gly Gln Ser Tyr
                165                 170                 175

Leu Pro Ala Ser Thr Gly Phe Ile Ile Gly Ala Leu Gly Leu Met Ala
            180                 185                 190

Phe Val Gly Trp Gln Trp Arg Gly Arg Met Arg Arg Gln Ala Leu Gly
        195                 200                 205

Leu Gln Ser Pro Ala Ser Thr Ala Val Val Gly Arg Gln Ala Leu Thr
    210                 215                 220

Ala Ile Ile Val Leu Gly Ala Ile Trp Leu Leu Asn Asp Tyr Arg Gly
225                 230                 235                 240

Val Pro Thr Pro Val Leu Leu Leu Thr Leu Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285

Lys Leu Ala Val Phe Ala Ile Asn Gly Leu Met Val Ala Ile Ala Gly
    290                 295                 300

Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335

Leu Ala Gly Gly Val Gly Ser Val Ala Gly Ala Val Met Gly Ala Phe
            340                 345                 350
```

```
Ile Met Ala Ser Leu Asp Asn Gly Met Ser Met Met Asp Val Pro Thr
            355                 360                 365

Phe Trp Gln Tyr Ile Val Lys Gly Ala Ile Leu Leu Leu Ala Val Trp
    370                 375                 380

Met Asp Ser Ala Thr Lys Arg Arg Ser
385                 390

<210> SEQ ID NO 54
<211> LENGTH: 393
<212> TYPE: PRT
<213> ORGANISM: Enterobacter cloacae

<400> SEQUENCE: 54

Met Ser Lys Ser Asn Pro Ser Asp Ile Lys Val Ala Val Gln Thr Pro
1               5                   10                  15

Gly Ala Phe Ala Gly Leu Lys Ala Leu Asn Leu Gln Val Phe Val Met
            20                  25                  30

Ile Ala Ala Ile Ile Ala Ile Met Leu Phe Phe Thr Trp Met Thr Asp
            35                  40                  45

Gly Ser Tyr Leu Ser Ala Arg Asn Val Ser Asn Leu Leu Arg Gln Thr
    50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Phe Asp Val Trp Leu Gly Trp Pro Leu Pro Leu Thr
            100                 105                 110

Val Ala Val Thr Leu Val Leu Gly Leu Val Leu Gly Ala Trp Asn Gly
        115                 120                 125

Trp Trp Val Ala Tyr Arg Lys Val Pro Ser Phe Ile Val Thr Leu Ala
130                 135                 140

Gly Met Leu Ala Phe Arg Gly Val Leu Ile Gly Ile Thr Asn Gly Thr
145                 150                 155                 160

Thr Val Ser Pro Thr Ser Ala Ala Met Ser Gln Ile Gly Gln Ser Tyr
                165                 170                 175

Leu Ser Asp Ser Met Gly Phe Thr Ile Gly Val Val Gly Leu Leu Ala
            180                 185                 190

Phe Val Val Trp Gln Trp Arg Gly Arg Met Arg Arg Gln Ser Leu Gly
        195                 200                 205

Leu Ala Ser Ser Pro Ser Thr Ser Val Val Gly Arg Gln Ala Leu Thr
210                 215                 220

Ala Val Ile Val Leu Gly Ala Ile Trp Leu Leu Asn Asp Tyr Arg Gly
225                 230                 235                 240

Val Pro Thr Pro Val Leu Leu Leu Ala Leu Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285

Lys Leu Ala Val Phe Ala Ile Asn Gly Leu Met Val Ala Ile Ala Gly
    290                 295                 300

Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335
```

```
Leu Ala Gly Gly Val Gly Ser Val Ala Gly Ala Val Met Gly Ala Phe
                340                 345                 350

Ile Met Ala Ser Leu Asp Asn Gly Met Ser Met Met Asp Val Pro Thr
                355                 360                 365

Phe Trp Gln Tyr Ile Val Lys Gly Ala Ile Leu Leu Leu Ala Val Trp
                370                 375                 380

Met Asp Ser Ala Thr Lys Arg Arg Thr
385                 390

<210> SEQ ID NO 55
<211> LENGTH: 321
<212> TYPE: PRT
<213> ORGANISM: Shigella dysenteriae

<400> SEQUENCE: 55

Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
                20                  25                  30

Tyr Ser Gly Leu Asp Tyr Pro Ser Leu Glu Ala Val Ile Arg Val Tyr
            35                  40                  45

Leu Glu Glu His Lys Val Glu Val Lys Asp Gly Cys Ile Ala Ile Ala
        50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Val Pro Met Leu Lys
                100                 105                 110

Lys Glu His Leu Ile Gln Phe Gly Ala Glu Pro Ile Glu Gly Lys
            115                 120                 125

Pro Ile Ala Val Tyr Gly Ala Gly Thr Gly Leu Gly Val Ala His Leu
        130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
                180                 185                 190

Pro Gly Leu Val Asn Leu Tyr Arg Ala Ile Val Lys Ala Asp Asn Arg
            195                 200                 205

Leu Pro Glu Asn Leu Lys Pro Lys Asp Ile Thr Glu Arg Ala Leu Ala
        210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
                260                 265                 270

Lys Ala Ser Gly Phe Arg Ala Ala Phe Glu Asp Lys Gly Arg Phe Lys
            275                 280                 285

Glu Tyr Val His Asp Ile Pro Val Tyr Leu Ile Val His Asp Asn Pro
        290                 295                 300

Gly Leu Leu Gly Ser Gly Ala His Leu Arg Gln Thr Leu Gly His Ile
```

Leu

<210> SEQ ID NO 56
<211> LENGTH: 321
<212> TYPE: PRT
<213> ORGANISM: Escherichia fergusonii

<400> SEQUENCE: 56

Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Asn Val Glu Val Gln Asp Gly Cys Ile Ala Ile Ala
    50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Gly Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
    210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Thr Leu Gly Thr Phe Gly
                245                 250                 255

Gly Val Tyr Ile Ala Gly Gly Ile Val Pro Arg Phe Leu Glu Phe
            260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
    290                 295                 300

Gly Leu Leu Gly Ser Gly Ala His Leu Arg Gln Thr Leu Gly His Ile
305                 310                 315                 320

Leu

<210> SEQ ID NO 57
<211> LENGTH: 371
<212> TYPE: PRT
<213> ORGANISM: Shigella dysenteriae

<400> SEQUENCE: 57

```
Met Tyr Lys Asn Gly Gly Arg Tyr Gln Arg Ser Val Arg Asn Pro Lys
1               5                   10                  15

Gln Ser Arg Leu Ala Ile Thr Val Leu Ser Ala Val Ala Leu Thr Leu
            20                  25                  30

Arg Arg Asp Ile Ile Arg Ala Asp Arg Leu His Pro Leu Thr Ser Cys
            35                  40                  45

Leu Lys Arg Asn Thr Ile Met Thr Asp Lys Leu Thr Ser Leu Arg Gln
50                  55                  60

Tyr Thr Thr Val Val Ala Asp Thr Gly Asp Ile Ala Ala Met Lys Leu
65                  70                  75                  80

Tyr Gln Pro Gln Asp Ala Thr Thr Asn Pro Ser Leu Ile Leu Asn Ala
                85                  90                  95

Ala Gln Ile Pro Glu Tyr Arg Lys Leu Ile Asp Asp Ala Val Ala Trp
            100                 105                 110

Ala Lys Gln Gln Ser Asn Asp Arg Ala Gln Gln Ile Val Asp Ala Thr
            115                 120                 125

Asp Lys Leu Ala Val Asn Ile Gly Leu Glu Ile Leu Lys Leu Val Pro
130                 135                 140

Gly Arg Ile Ser Thr Glu Val Asp Ala Arg Leu Ser Tyr Asp Thr Glu
145                 150                 155                 160

Ala Ser Ile Ala Lys Ala Lys Arg Leu Ile Lys Leu Tyr Asn Asp Ala
                165                 170                 175

Gly Ile Ser Asn Asp Arg Ile Leu Ile Lys Leu Ala Ser Thr Trp Gln
            180                 185                 190

Gly Ile Arg Ala Ala Glu Gln Leu Glu Lys Glu Gly Ile Asn Cys Asn
            195                 200                 205

Leu Thr Leu Leu Phe Ser Phe Ala Gln Ala Arg Ala Cys Ala Glu Ala
210                 215                 220

Gly Val Phe Leu Ile Ser Pro Phe Val Gly Arg Ile Leu Asp Trp Tyr
225                 230                 235                 240

Lys Ala Asn Thr Asp Lys Lys Glu Tyr Ala Pro Ala Glu Asp Pro Gly
                245                 250                 255

Val Val Ser Val Ser Glu Ile Tyr Gln Tyr Tyr Lys Glu His Gly Tyr
            260                 265                 270

Glu Thr Val Val Met Gly Ala Ser Phe Arg Asn Ile Gly Glu Ile Leu
            275                 280                 285

Glu Leu Ala Gly Cys Asp Arg Leu Thr Ile Ala Pro Ala Leu Leu Lys
290                 295                 300

Glu Leu Ala Glu Ser Glu Gly Ala Ile Glu Arg Lys Leu Ser Tyr Thr
305                 310                 315                 320

Gly Glu Val Lys Ala Arg Pro Ala Arg Ile Thr Glu Ser Glu Phe Leu
                325                 330                 335

Trp Gln His Asn Gln Asp Pro Met Ala Val Lys Leu Ala Glu Gly
            340                 345                 350

Ile Arg Lys Phe Ala Ile Asp Gln Glu Lys Leu Glu Lys Met Ile Gly
            355                 360                 365

Asp Leu Leu
        370
```

<210> SEQ ID NO 58
<211> LENGTH: 317
<212> TYPE: PRT

<213> ORGANISM: Escherichia fergusonii

<400> SEQUENCE: 58

```
Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Ser
50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Tyr Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
210                 215                 220

Ala Ser Phe Arg Asn Met Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Val Glu Arg Lys Leu Ser Phe Ser Gly Glu Val Lys Ala Arg
            260                 265                 270

Pro Glu Arg Ile Thr Glu Ser Glu Phe Leu Trp Gln His Asn Gln Asp
        275                 280                 285

Pro Met Ala Val Asp Lys Leu Ala Asp Gly Ile Arg Lys Phe Ala Val
290                 295                 300

Asp Gln Glu Lys Leu Glu Lys Met Ile Gly Glu Leu Leu
305                 310                 315
```

<210> SEQ ID NO 59
<211> LENGTH: 673
<212> TYPE: PRT
<213> ORGANISM: Shigella dysenteriae

<400> SEQUENCE: 59

```
Met Pro Phe Ile Ile Arg Ser Gly Val Lys Met Ser Ser Arg Lys Glu
1               5                   10                  15

Leu Ala Asn Ala Ile Arg Ala Leu Ser Met Asp Ala Val Gln Lys Ala
            20                  25                  30

Lys Ser Gly His Pro Gly Ala Pro Met Gly Met Ala Asp Ile Ala Glu
```

```
            35                  40                  45
Val Leu Trp Arg Asp Phe Leu Lys His Asn Pro Gln Asn Pro Ser Trp
 50                  55                  60

Ala Asp Arg Asp Arg Phe Val Leu Ser Asn Gly His Gly Ser Met Leu
 65                  70                  75                  80

Ile Tyr Ser Leu Leu His Leu Thr Gly Tyr Asp Leu Pro Met Glu Glu
                 85                  90                  95

Leu Lys Asn Phe Arg Gln Leu His Ser Lys Thr Pro Gly His Pro Glu
                100                 105                 110

Val Gly Tyr Thr Ala Gly Val Glu Thr Thr Thr Gly Pro Leu Gly Gln
            115                 120                 125

Gly Ile Ala Asn Ala Val Gly Met Ala Ile Ala Glu Lys Thr Leu Ala
        130                 135                 140

Ala Gln Phe Asn Arg Pro Gly His Asp Ile Val Asp His Tyr Thr Tyr
145                 150                 155                 160

Ala Phe Met Gly Asp Gly Cys Met Met Glu Gly Ile Ser His Glu Val
                165                 170                 175

Cys Ser Leu Ala Gly Thr Leu Lys Leu Gly Lys Leu Ile Ala Phe Tyr
            180                 185                 190

Asp Asp Asn Gly Ile Ser Ile Asp Gly His Val Glu Gly Trp Phe Thr
        195                 200                 205

Asp Asp Thr Ala Met Arg Phe Glu Ala Tyr Gly Trp His Val Ile Arg
210                 215                 220

Asp Ile Asp Gly His Asp Ala Ala Ser Ile Lys Arg Ala Val Glu Glu
225                 230                 235                 240

Ala Arg Ala Val Thr Asp Lys Pro Ser Leu Leu Met Cys Lys Thr Ile
                245                 250                 255

Ile Gly Phe Gly Ser Pro Asn Lys Ala Gly Thr His Asp Ser His Gly
            260                 265                 270

Ala Pro Leu Gly Asp Ala Glu Ile Ala Leu Thr Arg Glu Gln Leu Gly
        275                 280                 285

Trp Lys Tyr Ala Pro Phe Glu Ile Pro Ser Glu Ile Tyr Ala Gln Trp
290                 295                 300

Asp Ala Lys Glu Ala Gly Gln Ala Lys Glu Ser Ala Trp Asn Glu Lys
305                 310                 315                 320

Phe Ala Ala Tyr Ala Lys Ala Tyr Pro Gln Glu Ala Ala Glu Phe Thr
                325                 330                 335

Arg Arg Met Lys Gly Glu Met Pro Ser Asp Phe Asp Ala Lys Ala Lys
            340                 345                 350

Glu Phe Ile Ala Lys Leu Gln Ala Asn Pro Ala Lys Ile Ala Ser Arg
        355                 360                 365

Lys Ala Ser Gln Asn Ala Ile Glu Ala Phe Gly Pro Leu Leu Pro Glu
370                 375                 380

Phe Leu Gly Gly Ser Ala Asp Leu Ala Pro Ser Asn Leu Thr Leu Trp
385                 390                 395                 400

Ser Gly Ser Lys Ala Ile Asn Glu Asp Ala Ala Gly Asn Tyr Ile His
                405                 410                 415

Tyr Gly Val Arg Glu Phe Gly Met Thr Ala Ile Ala Asn Gly Ile Ser
            420                 425                 430

Leu His Gly Gly Phe Leu Pro Tyr Thr Ser Thr Phe Leu Met Phe Val
        435                 440                 445

Glu Tyr Ala Arg Asn Ala Val Arg Met Ala Ala Leu Met Lys Gln Arg
450                 455                 460
```

```
Gln Val Met Val Tyr Thr His Asp Ser Ile Gly Leu Gly Glu Asp Gly
465                 470                 475                 480

Pro Thr His Gln Pro Val Glu Gln Val Ala Ser Leu Arg Val Thr Pro
            485                 490                 495

Asn Met Ser Thr Trp Arg Pro Cys Asp Gln Val Glu Ser Ala Val Ala
            500                 505                 510

Trp Lys Tyr Gly Val Glu Arg Gln Asp Gly Pro Thr Ala Leu Ile Leu
            515                 520                 525

Ser Arg Gln Asn Leu Ala Gln Gln Glu Arg Thr Glu Glu Gln Leu Ala
            530                 535                 540

Asn Ile Ala Arg Gly Gly Tyr Val Leu Lys Asp Cys Ala Gly Gln Pro
545                 550                 555                 560

Glu Leu Ile Phe Ile Ala Thr Gly Ser Glu Val Glu Leu Ala Val Ala
                565                 570                 575

Ala Tyr Glu Lys Leu Thr Ala Glu Gly Val Lys Ala Arg Val Val Ser
            580                 585                 590

Met Pro Ser Thr Asp Ala Phe Asp Lys Gln Asp Ala Ala Tyr Arg Glu
            595                 600                 605

Ser Val Leu Pro Lys Ala Val Thr Ala Arg Val Ala Val Glu Ala Gly
610                 615                 620

Ile Ala Asp Tyr Trp Tyr Lys Tyr Val Gly Leu Asn Gly Ala Ile Val
625                 630                 635                 640

Gly Met Thr Thr Phe Gly Glu Ser Ala Pro Ala Glu Leu Leu Phe Glu
                645                 650                 655

Glu Phe Gly Phe Thr Val Asp Asn Val Val Ala Lys Ala Lys Glu Leu
            660                 665                 670

Leu

<210> SEQ ID NO 60
<211> LENGTH: 663
<212> TYPE: PRT
<213> ORGANISM: Escherichia fergusonii

<400> SEQUENCE: 60

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160
```

```
Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205

Gly Trp His Val Ile Arg Gly Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575
```

```
Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
            610                 615                 620

Leu Asn Gly Ala Ile Ile Gly Met Asn Thr Phe Gly Glu Ser Ala Pro
625                 630                 635                 640

Ala Glu Gln Leu Phe Glu Glu Phe Gly Phe Thr Val Asp Asn Val Val
                645                 650                 655

Ala Lys Ala Lys Ala Leu Leu
            660

<210> SEQ ID NO 61
<211> LENGTH: 51
<212> TYPE: DNA
<213> ORGANISM: Artificial
<220> FEATURE:
<223> OTHER INFORMATION: oligonucleotide

<400> SEQUENCE: 61
ggtaccaagg aaggactgat catgagttct gaaagtagtc agggtctagt c          51

<210> SEQ ID NO 62
<211> LENGTH: 28
<212> TYPE: DNA
<213> ORGANISM: Artificial
<220> FEATURE:
<223> OTHER INFORMATION: oligonucleotide

<400> SEQUENCE: 62
ctgcagctac ttctgggagc gccacatc                                    28

<210> SEQ ID NO 63
<211> LENGTH: 46
<212> TYPE: DNA
<213> ORGANISM: Artificial
<220> FEATURE:
<223> OTHER INFORMATION: oligonucleotide

<400> SEQUENCE: 63
ctgcagaagg aaggactgat cgtgcgtata ggtatcgatt taggcg                46

<210> SEQ ID NO 64
<211> LENGTH: 30
<212> TYPE: DNA
<213> ORGANISM: Artificial
<220> FEATURE:
<223> OTHER INFORMATION: oligonucleotide

<400> SEQUENCE: 64
tctagattac tcttgtggcc ataaccacgc                                  30

<210> SEQ ID NO 65
<211> LENGTH: 51
<212> TYPE: DNA
<213> ORGANISM: Artificial
<220> FEATURE:
<223> OTHER INFORMATION: oligonucleotide

<400> SEQUENCE: 65
tctagaaagg aaggtcgact catgcaaaaa ctcattaact cagtgcaaaa c          51
```

```
<210> SEQ ID NO 66
<211> LENGTH: 35
<212> TYPE: DNA
<213> ORGANISM: Artificial
<220> FEATURE:
<223> OTHER INFORMATION: oligonucleotide

<400> SEQUENCE: 66
gagctcttac agcttgttgt aaacacgcgc taaac                              35

<210> SEQ ID NO 67
<211> LENGTH: 28
<212> TYPE: DNA
<213> ORGANISM: Artificial
<220> FEATURE:
<223> OTHER INFORMATION: oligonucleotide

<400> SEQUENCE: 67
gttctatcga ttgggttaat gccagtgg                                      28

<210> SEQ ID NO 68
<211> LENGTH: 26
<212> TYPE: DNA
<213> ORGANISM: Artificial
<220> FEATURE:
<223> OTHER INFORMATION: oligonucleotide

<400> SEQUENCE: 68
ggaacatctg cggtgcataa tacagc                                        26

<210> SEQ ID NO 69
<211> LENGTH: 21
<212> TYPE: DNA
<213> ORGANISM: Artificial
<220> FEATURE:
<223> OTHER INFORMATION: oligonucleotide

<400> SEQUENCE: 69
gcgaggttgc agcgggaagt g                                             21

<210> SEQ ID NO 70
<211> LENGTH: 27
<212> TYPE: DNA
<213> ORGANISM: Artificial
<220> FEATURE:
<223> OTHER INFORMATION: oligonucleotide

<400> SEQUENCE: 70
aatttcactg cctttcagcg catgtcc                                       27

<210> SEQ ID NO 71
<211> LENGTH: 22
<212> TYPE: DNA
<213> ORGANISM: Artificial
<220> FEATURE:
<223> OTHER INFORMATION: oligonucleotide

<400> SEQUENCE: 71
cgctgacgcc tttccttgcg at                                            22

<210> SEQ ID NO 72
<211> LENGTH: 24
<212> TYPE: DNA
<213> ORGANISM: Artificial
<220> FEATURE:
<223> OTHER INFORMATION: oligonucleotide
```

```
<400> SEQUENCE: 72
gcggtgtttc agcgaacagg aaca                                              24

<210> SEQ ID NO 73
<211> LENGTH: 23
<212> TYPE: DNA
<213> ORGANISM: Artificial
<220> FEATURE:
<223> OTHER INFORMATION: oligonucleotide

<400> SEQUENCE: 73
cgactcacta tagggagagc ggc                                               23

<210> SEQ ID NO 74
<211> LENGTH: 24
<212> TYPE: DNA
<213> ORGANISM: Artificial
<220> FEATURE:
<223> OTHER INFORMATION: oligonucleotide

<400> SEQUENCE: 74
aagaacatcg attttccatg gcag                                              24

<210> SEQ ID NO 75
<211> LENGTH: 17
<212> TYPE: DNA
<213> ORGANISM: Artificial
<220> FEATURE:
<223> OTHER INFORMATION: oligonucleotide

<400> SEQUENCE: 75
gtaaaacgac ggccagt                                                      17

<210> SEQ ID NO 76
<211> LENGTH: 25
<212> TYPE: DNA
<213> ORGANISM: Artificial
<220> FEATURE:
<223> OTHER INFORMATION: oligonucleotide

<400> SEQUENCE: 76
ctcgagccgg aattgccagc tgggg                                             25

<210> SEQ ID NO 77
<211> LENGTH: 30
<212> TYPE: DNA
<213> ORGANISM: Artificial
<220> FEATURE:
<223> OTHER INFORMATION: oligonucleotide

<400> SEQUENCE: 77
catatgaaac gatcctcatc ctgtctcttg                                        30

<210> SEQ ID NO 78
<211> LENGTH: 35
<212> TYPE: DNA
<213> ORGANISM: Artificial
<220> FEATURE:
<223> OTHER INFORMATION: oligonucleotide

<400> SEQUENCE: 78
catatgacaa agtatgcatt agtcggtgat gtggg                                  35

<210> SEQ ID NO 79
<211> LENGTH: 42
```

```
<212> TYPE: DNA
<213> ORGANISM: Artificial
<220> FEATURE:
<223> OTHER INFORMATION: oligonucleotide

<400> SEQUENCE: 79
gtcgacttac agaatgtgac ctaaggtctg gcgtaaatgt gc                    42

<210> SEQ ID NO 80
<211> LENGTH: 52
<212> TYPE: DNA
<213> ORGANISM: Artificial
<220> FEATURE:
<223> OTHER INFORMATION: oligonucleotide

<400> SEQUENCE: 80
ggatccatga ggatcgtttc gcatgagttc tgaaagtagt cagggtctag tc        52

<210> SEQ ID NO 81
<211> LENGTH: 34
<212> TYPE: DNA
<213> ORGANISM: Artificial
<220> FEATURE:
<223> OTHER INFORMATION: oligonucleotide

<400> SEQUENCE: 81
gagctcctac ttctgggagc gccacatctc ctcg                            34

<210> SEQ ID NO 82
<211> LENGTH: 45
<212> TYPE: DNA
<213> ORGANISM: Artificial
<220> FEATURE:
<223> OTHER INFORMATION: oligonucleotide

<400> SEQUENCE: 82
attagggccc aaggaggtta cagcatgcaa gcctattttg accag                45

<210> SEQ ID NO 83
<211> LENGTH: 31
<212> TYPE: DNA
<213> ORGANISM: Artificial
<220> FEATURE:
<223> OTHER INFORMATION: oligonucleotide

<400> SEQUENCE: 83
attgcccggg ttatttgtcg aacagataat g                               31

<210> SEQ ID NO 84
<211> LENGTH: 45
<212> TYPE: DNA
<213> ORGANISM: Artificial
<220> FEATURE:
<223> OTHER INFORMATION: oligonucleotide

<400> SEQUENCE: 84
attgcccggg aaggaggtta cagcatgtat atcgggatag atctt                45

<210> SEQ ID NO 85
<211> LENGTH: 31
<212> TYPE: DNA
<213> ORGANISM: Artificial
<220> FEATURE:
<223> OTHER INFORMATION: oligonucleotide

<400> SEQUENCE: 85
```
cccgactagt ttacgccatt aatggcagaa g    31

<210> SEQ ID NO 86
<211> LENGTH: 44
<212> TYPE: DNA
<213> ORGANISM: Artificial
<220> FEATURE:
<223> OTHER INFORMATION: oligonucleotide

<400> SEQUENCE: 86
cccgactagt aaggaggtta cagcatgaat acccagtata attc    44

<210> SEQ ID NO 87
<211> LENGTH: 31
<212> TYPE: DNA
<213> ORGANISM: Artificial
<220> FEATURE:
<223> OTHER INFORMATION: oligonucleotide

<400> SEQUENCE: 87
attgccgcgg ttacagcgta gcagtttgtt g    31

<210> SEQ ID NO 88
<211> LENGTH: 46
<212> TYPE: DNA
<213> ORGANISM: Artificial
<220> FEATURE:
<223> OTHER INFORMATION: oligonucleotide

<400> SEQUENCE: 88
cccgactagt aaggaggcta cagcatgaaa ataaagaaca ttctac    46

<210> SEQ ID NO 89
<211> LENGTH: 30
<212> TYPE: DNA
<213> ORGANISM: Artificial
<220> FEATURE:
<223> OTHER INFORMATION: oligonucleotide

<400> SEQUENCE: 89
attgccgcgg tcaagaacgg cgtttggttg    30

<210> SEQ ID NO 90
<211> LENGTH: 24
<212> TYPE: DNA
<213> ORGANISM: Artificial
<220> FEATURE:
<223> OTHER INFORMATION: oligonucleotide

<400> SEQUENCE: 90
aaaaccgcgg cggctcggaa gtcg    24

<210> SEQ ID NO 91
<211> LENGTH: 23
<212> TYPE: DNA
<213> ORGANISM: Artificial
<220> FEATURE:
<223> OTHER INFORMATION: oligonucleotide

<400> SEQUENCE: 91
cgactcacta tagggagagc ggc    23

<210> SEQ ID NO 92
<211> LENGTH: 24
<212> TYPE: DNA
<213> ORGANISM: Artificial

```
<220> FEATURE:
<223> OTHER INFORMATION: oligonucleotide

<400> SEQUENCE: 92
aagaacatcg attttccatg gcag                                          24

<210> SEQ ID NO 93
<211> LENGTH: 17
<212> TYPE: DNA
<213> ORGANISM: Artificial
<220> FEATURE:
<223> OTHER INFORMATION: oligonucleotide

<400> SEQUENCE: 93
gtaaaacgac ggccagt                                                  17

<210> SEQ ID NO 94
<211> LENGTH: 17
<212> TYPE: DNA
<213> ORGANISM: Artificial Sequence
<220> FEATURE:
<223> OTHER INFORMATION: oligonucleotide

<400> SEQUENCE: 94
gtaaaacgac ggccagt                                                  17

<210> SEQ ID NO 95
<211> LENGTH: 16
<212> TYPE: DNA
<213> ORGANISM: Artificial Sequence
<220> FEATURE:
<223> OTHER INFORMATION: oligonucleotide

<400> SEQUENCE: 95
aacagctatg accatg                                                   16
```

MICROORGANISMS WITH EXTENDED SUBSTRATE UTILIZATION RANGE

CROSS-REFERENCE TO RELATED PATENT APPLICATIONS

The present application claims the benefit of priority under 35 U.S.C. §119(e) to U.S. Provisional Patent Application No. 61/364,898, filed on Jul. 16, 2010, and the present application claims the benefit of priority under 35 U.S.C. §119(a) to European Patent Application No. 10169808.2, filed on Jul. 16, 2010.

FIELD OF INVENTION

The present invention relates to new microorganisms having improved capability of utilizing monomeric sugars found in renewable resources, in particular lignocellulose. More specifically, the invention relates to genetically modified *Ralstonia* and *Cupriavidus* hosts and methods of using them.

BACKGROUND

Lignocellulose is the main renewable resource with several applications, including feedstock for bulk chemicals. The main components of lignocellulose are cellulose, hemicellulose and lignin. The cellulose fraction comprises polymers of the hexose sugar, glucose. The hemicellulose fraction is mainly comprised of polymers of the pentose sugars xylose, and arabinose, and the hexose sugars mannose, glucose and galactose. These are abundant in the lignocellulosic biomass of soft woods, whereas xylose occurs in both soft and hard woods.

There are numerous examples for efforts to utilize lignocelluloses more effectively by microorganisms and to extend the substrate utilization range of microorganisms towards low-cost and abundant carbon sources. For example, attempts have been made to broaden the utilization of unfermentable pentoses like xylose and arabinose occurring in lignocellulosic biomass in many microorganisms. Many of these investigations aimed at the extension of carbohydrate metabolism in ethanol producers, such as *Zymomonas mobilis* and *Saccharomyces cerevisiae* for ethanol fermentation bioprocess. WO 2009/08190, for example, describes genetical modification of ethanol producing bacterium belonging to the genus *Zymomonas* to utilize glucose, mannose, and xylose.

Bacteria belonging to genus *Ralstonia* and *Cupriavidus* are chemolithoautotrophs which are capable of accumulating large amounts of polyhydroxyalkanoates (PHAs) from renewable resources or from carbon dioxide. Strains of the genus *Ralstonia* and *Cupriavidus*, in particular, *R. eutropha* (new name *Cupriavidus necator*) have been shown to possess large biotechnological potential as these strains can be cultivated to high cell densities in large scale (Schlegel et al. 1961) and is suitable for large-scale industrial bioprocesses. Unfortunately, *Cupriavidus* and *Ralstonia* have a very narrow carbohydrate substrate range limited to fructose, N-acetylglucosamine and gluconate. Attempts to broaden the substrate utilization range of *R. euthropha* H16 have been described in the prior art (Pries et al. 1990, Schlegel and Gottschalk, 1965). A spontaneous glucose-utilizing mutant of *R. euthropha* H16 which presumably transported this sugar into the cell by a passive transporter has been reported to be isolated (Schlegel and Gottschalk 1965, König, et al. 1969). Furthermore, Pries et al. 1990 have reported of the introduction of β-galactosidase gene and the gal operon from *E. coli* into *R. eutropha* strain H16 and utilization of lactose and galactose by this bacterium.

Further, Buchholz et al. 1994 have described the construction of a genomic library of *Pseudomonas saccharophila* and its transfer to *Alcaligenes eutrophus* (*Ralstonia eutropha*). An insert containing xyl genes encoding xylose isomerase and xylulokinase made the host *A. eutrophus* (pGN3) to grow on xylose.

In spite of the previous attempts to extend the substrate utilization range of certain microorganisms towards low-cost and abundant carbon sources, there is still a need for new methods and microorganisms for more efficient utilization of renewable resources, in particular lignocelluloses.

SUMMARY

One object of the present invention is to provide a process for effectively utilizing lignocelluloses, in particular monomeric sugars found in lignocelluloses.

Another object of the present invention is to provide new microorganisms capable of utilizing lignocelluloses, in particular monomeric sugars found in lignocellulose.

To achieve these objects the invention is characterized by the features that are enlisted in the independent claims. Other claims represent the preferred embodiments of the invention.

The invention described herein provides, in one aspect, a new microorganism, which is genetically modified to express genes broadening its capability of using different monomeric sugars which are present in lignocellulose.

The present invention provides, in one aspect, a microorganism of the genus *Cupriavidus* or *Ralstonia*, which is capable of using mannose as carbon source.

In another aspect the invention provides a microorganism of the genus *Cupriavidus* or *Ralstonia*, which is capable of using xylose as carbon source.

In one embodiment the microorganism is genetically modified to express phosphomannose isomerase (EC 5.3.1.8) and facilitated diffusion protein for mannose uptake (EC 1.3.1.74) and/or xylose proton symporter E, and optionally mannofructokinase (EC 2.7.1.4). Typically, microorganisms of the genus *Cupriavidus* or *Ralstonia* are incapable of utilizing mannose without said modification, whereas the modified microorganisms are capable of utilizing mannose. The genes used for said genetic modification may be exogenous or endogenous, typically they are exogenous. In various embodiments, when the microorganism is genetically modified to express a gene encoding facilitated diffusion protein for mannose uptake (EC 1.3.1.74), in particular gene glf, the microorganism host is surprisingly capable of utilizing also glucose.

In one embodiment the microorganism is genetically modified to express xylose isomerase (EC 5.3.1.5), xylulokinase (EC 2.7.1.17) and a high affinity ABC-transporter (Xyl G, EC 3.6.3.17, Xyl F, and/or Xyl H) and/or xylose proton symporter E. Typically, microorganisms of the genus *Cupriavidus* or *Ralstonia* are incapable of utilizing xylose without said modification, whereas the modified microorganisms are capable of utilizing xylose. The genes used for said genetic modification may be exogenous or endogenous, typically they are exogenous. Typically, said microorganisms are incapable of utilizing arabinose without said genes, whereas in various embodiments the modified microorganisms are surprisingly capable of utilizing arabinose as the carbon source. Furthermore, when the microorganisms are genetically modified to express high affinity ABC-transporter (in particular genes Xyl G, (EC 3.6, 3.17), Xyl F and Xyl H), the microorganism hosts are surprisingly capable of utilizing glucose and galactose.

In one further embodiment of the invention the microorganism hosts are genetically modified to express glucokinase (EC 2.7.1.2). This modification makes the genetically modified micoorganism to be also capable of utilizing glucose.

The microorganisms are thus capable of utilizing glucose as carbon source in addition to mannose, or in addition to mannose, xylose and arabinose.

In a preferred embodiment of the invention the microorganisms are capable of utilizing mannose, glucose, galactose, xylose and arabinose as carbon source.

In one further embodiment the microorganisms are genetically modified to express transaldolase (EC 2.2.1.2) and/or transketolase (EC 2.2.1.1). The genes encoding transaldolase and/or transketolase improve the fastness of growth of the modified microorganism in particular on pentoses, such as xylose and arabinose.

The microorganism may be any species or strains belonging to the genus *Cupriavidus* or *Ralstonia*. Preferably, the microorganism belongs to *C. necator* (earlier *R. eutropha* or *Alkaligenes eutrophus*) species.

In one aspect the invention provides a vector comprising a gene encoding phosphomannose isomerase (EC 5.3.1.8), a gene encoding facilitated diffusion protein for mannose uptake (EC 1.3.1.74), a gene encoding xylose proton symporter E and/or a gene encoding mannofructokinase (EC 2.7.1.4), and regulatory elements for regulating expression of said genes in *Cupriavidus* or *Ralstonia*. Said genes may be in the same or separate vectors.

In another aspect the vector may comprise a gene encoding xylose isomerase (EC 5.3.1.5), xylulokinase (EC 2.7.1.17), a high affinity ABC-transporter (Xyl G, EC 3.6.3.17, Xyl F, and/or Xyl H) and/or xylose proton symporter E, and regulatory elements for regulating expression of said genes in *Cupriavidus* or *Ralstonia*. Said genes may be in the same or separate vectors.

In one embodiment the vector may comprise a gene encoding transaldolase (EC 2.2.1.2) and/or transketolase (EC 22.1.1). Said genes may be in the same or separate vectors.

In one further embodiment the vector may comprise a gene encoding glucokinase (EC 2.7.1.2). Said gene may be in the same or separate vectors as the above listed genes.

In one still further embodiment a vector comprise any one or any combination of the above listed genes.

Any promoter that can be expressed in strains of the genera *Ralstonia* or *Cupriavidus* can be used in the vector.

Suitable promoters comprise for example lac-promoter, neokanamycin-promoter, glyceraldehyde-3-phophate dehydrogenase promoter, P2, hydrogenase (SH) promoter and $P_L$.

In one preferred embodiment the vector is a broad host range plasmid which can be used to extend the substrate utilization range of various different host strains of *Cupriavidus* or *Ralstonia*.

In one aspect the invention provides a method for modifying the microorganisms of the genera *Ralstonia* or *Cupriavidus*. The method comprises the hosts are genetically modified to express one or more nucleotide sequences selected from the group comprising a nucleotide sequence or sequences encoding phosphomannose isomerase (EC5.3.1.8) and facilitated diffusion protein for mannose uptake (EC1.3.1.74) and/or xylose proton symporter E, and optionally mannofructokinase (EC2.7.1.4), wherein said microorganism is capable of growing on mannose and optionally also on glucose as the carbon source, and/or a nucleotide sequence or sequences encoding xylose isomerase (EC 5.3.1.5), xylulokinase (E 2.7.1.17) and a high affinity ABC-transporter and/or xylose proton symporter E, wherein said microorganism is capable of growing on xylose, or xylose and arabinose, and optionally also on glucose and galactose as the carbon source.

In one embodiment the method may further comprise that the microorganism is genetically modified to express transaldolase (EC2.2.1.2) and/or transketolase (EC2.2.1.1).

In one embodiment the method may further comprise that the microorganism is genetically modified to express glucokinase (EC 2.7.1.2).

In one still further aspect the invention provides a method for cultivating the modified microorganism in a cultivation medium comprising mannose, glucose, galactose, xylose or arabinose, any of them, any combination of them, or all of them, as carbon source.

In one embodiment the cultivation medium may comprise mannose as carbon source and optionally glucose.

In another embodiment the cultivation medium may comprise either or both xylose and arabinose as carbon source, and optionally also glucose and/or galactose.

In one further embodiment the cultivation medium may comprise mannose and either or both xylose and arabinose as carbon source, and optionally also glucose and/or galactose.

In one further aspect the method comprises that the microorganism is allowed to synthesize bulk chemicals, such as lipids, for example polyhydroxyalkanoates, fatty acids or fatty acid derivatives, and the chemical is recovered from the cells, or from the cultivation medium.

Considerable advantages are obtained by means of the present invention. By means of the invention new microorganisms belonging to genus *Cupriavidus* or *Ralstonia* are obtained, said microorganisms having an extended substrate utilization range. The modified microorganisms as described herein can utilize effectively low-cost carbohydrates, in particular lignocellulose comprising monomeric sugars. Xylose, mannose and arabinose are wood sugars present in a polymerized form in the hemicelluloses of plant cell walls. The microorganisms of the present invention are also able to use monomeric glucose, which is found in particular in sucrose and starch and also in cellulose and hemicellulose fractions in lignocellulosic materials. The modified microorganisms of the present invention are suitable for producing many bulk chemicals.

DETAILED DESCRIPTION OF THE INVENTION

Figure 1:
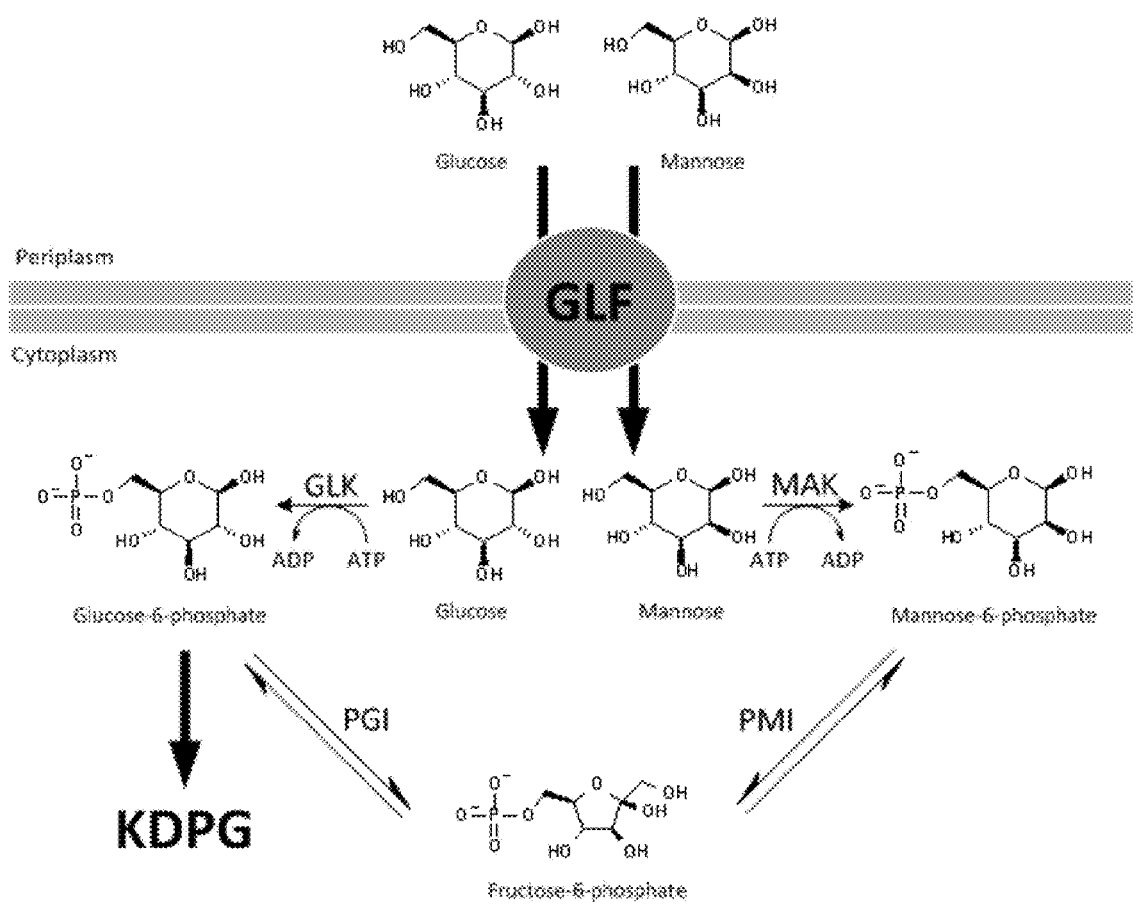
FIG. 1. Pathways of mannose and glucose utilization established in *R. eutropha* strain H16. GLF, glucose-facilitated diffusion transporter; KDPG, Entner-Doudoroff pathway; MAK, mannofructokinase; PMI, phosphomannose isomerase, GLK, glucokinase; PGI, phosphoglucose isomerase.

"A genetically modified microorganism" refers here to a microorganism whose genetic material has been altered using genetic engineering techniques. These techniques involve the use of nucleic acid molecules from different sources, for example from another microorganism or they may be at least partly synthetic. Nucleic acid molecules from different sources may be combined to one or more molecules. These constructions may be transferred into a microorganism, giving it modified or novel genetic constructions.

"A gene" refers here typically to a nucleotide sequence encoding a specific product, here usually an enzyme. The coding region is typically operationally linked into regulatory regions, in particular into a promoter, which is able to function in the host cell. Into a host cell is here typically introduced a genetic construct, which consist essentially of a coding region of a gene and a regulatory region, in particular a promoter, functional in the host cell. A suitable vector may be used to introduce the desired genetic construct into a host cell. "A gene" may refer to one or more genes.

Genetical modification may mean that one or more exogenous genes are introduced into and expressed in a microorganism host, or that one or more of the expressed genes are endogenous and one or more are exogenous, or that the expression of one or more endogenous genes is increased in a host compared to the parent host.

Microorganism hosts in various embodiments of the invention are preferably bacteria belonging to the genus *Cupriavidus* or *Ralstonia*.

A microorganism refers here typically to an isolated microorganism, i.e. a microorganism is used as a pure culture.

In one embodiment the species may be any *Ralstonia* species including, but not limited to *Ralstonia insidiosa, R. mannitolytica, R. pickettii, R. solanacearum* and *R. syzygii*. In another embodiment the species may be any *Cupriavidus* species including, but not limited to *Cupriavidus basilensis, C. campinensis, C. gilardii, C. laharis, C. metallidurans, C. necator, C. oxalaticus, C. pauculus, C. pinatubonensis, C. respiraculi* and *C. taiwanensis* (Bacterial Nomenclature up-to-date (approved lists, validation list), May 2010, compiled by DSMZ—Deutsche Sammlung von Mikroorganismen und Zellkulturen GmbH). Preferred species are *R. eutropha* and *C. metallidurans*. Most preferred species is *R. eutropha* (present name *C. necator*, earlier names *Alcaligenes eutrophus* and *Hydrogenomonas eutropha*). *Cupriavidus* and *Ral-*

*stonia* strains are available to the public from microbial culture collections, such as ATCC, DSMZ and NCIB.

The invention has been exemplified by using *R. eutropha* strain H 16 (present name *C. necator*). This strain is a wild type strain, which is available from Deutsche Sammlung von Mikroorganismen und Zellkulturen, DSMZ, under accession number DSM428, from American Type Culture Collection under accession number ATCC17699, and from National Collection of Industrial and Marine Bacteria, NCIBM, under Accession number NCIB10442. All these strains are available to the public.

Deposited *R. eutropha* H16 strains, which can be used in the invention are *Ralstonia eutropha* H16, DSMZ Accession No.: DSM428, DSM 15443 (mutant of DSM 428)

Taxonomy ID: 381666; Inherited blast name: b-proteobacteria
Other names:
synonyms: *Cupriavidus necator* H16, *Alcaligenes eutropha* H16, *Wautersia eutropha* H16, *Cupriavidus necator* ATCC 17699, *Ralstonia eutropha* ATCC 17699;
equivalentic names: *Ralstonia eutropha* strain H16, *Ralstonia eutropha* str. H16
Other *R. eutropha* strains which can be used in the invention are:
*Ralstonia eutropha* H850
DSMZ Accession No.: DSM 13439
Taxonomy ID: 53482; Inherited blast name: b-proteobacteria
Other names:
synonyms: *Wautersia eutropha* H850, *Cupriavidus necator* H850, *Alcaligenes eutrophus* H850
*Ralstonia eutropha* JMP134
DSMZ Accession No.: DSM 4058
Taxonomy ID: 264198; Inherited blast name: b-proteobacteria
Other names:
synonyms: *Cupriavidus pinatubonensis* JMP134, *Cupriavidus necator* JMP134, *Wautersia eutropha* JMP134, *Ralstonia* sp. JMP134;
equivalent names: *Ralstonia eutropha* str. JMP134 and *Ralstonia eutropha* strain JMP134

In addition, also the following other *Ralstonia eutropha* strains can be used in the invention:
*Ralstonia eutropha* 335 (DSMZ Accession No.: DSM 531, ATCC 17697)
*Ralstonia eutropha* N9A (DSMZ Accession No.: DSM 518;
*Ralstonia eutropha* B19 (DSMZ Accession No.: DSM 515):
*Ralstonia eutropha* G27 (DSMZ Accession No.: DSM 516):
*Ralstonia eutropha* G29 (DSMZ Accession No.: DSM 517):
*Ralstonia eutropha* 336 (DSMZ Accession No.: DSM 529, ATCC 17698)
*Ralstonia eutropha* 338 (DSMZ Accession No.: DSM 530, ATCC 17700);
*Ralstonia eutropha* TA06 (DSMZ Accession No.: DSM 4182);
*Ralstonia eutropha* H850 (DSMZ Accession No.: DSM 5536; NRRL B-15940)
*Ralstonia eutropha* $KTO_2$ (DSMZ Accession No.: DSM 6519);
*Ralstonia eutropha* Tfa17 (DSMZ Accession No.: DSM 11098)
*Ralstonia eutropha* N-1 (DSMZ Accession No: DSM 13513; ATCC 43291)
*Ralstonia eutropha* NRRL B-2804 (DSMZ Accession No.: DSM 30029, ATCC 25207, NRRL B-2804);

"Lignocellulosic biomass" refers here to plant biomass that comprises mainly cellulose, hemicelluloses and lignin. Lignocellulosic biomass is for example agricultural residues (e.g. wheat, barley or rice straw, husk (chaff), corn stover, sugar cane bagasse), energy crops, wood or plant materials or residues and municipal waste, e.g. paper waste.

"Bulk chemical" refers to any useful chemicals, which may be produced from inexpensive raw materials in high amounts. Examples of useful bulk chemicals are lipids, for example polyhydroxyalkanoates, in particular polyhydroxybutyrate (PHB), or other lipids, such as fatty acids and/or fatty acid derivatives, for example acylglyserols.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty acid esters, phospholipids, glycolipids, sphingolipids and acylglycerols. The terms lipids and oils are used in this description synonymously.

The term "acyglycerol" refers to an ester of glycerol and fatty acids. Acylglycerols occur naturally as fats and fatty oils. Examples of acylglycerols include triacylglycerols (TAGs, triglycerides) diacylglycerols (diglycerides) and monoacylglycerols (monoglycerides).

"Raw materials" or "starting materials" are materials which form or are included to the cultivation medium of a *Cupriavidus* or *Ralstonia* host and which the microorganism can use for its growth and/or production of desired chemicals. Advantageously the materials are inexpensive and available in large amounts. Suitable starting materials are for example lignocellulosic biomass (e.g. wood or plant materials, their fractions or residues) and agricultural waste(s) or residue(s), micro- or macroalgae and any materials, which comprise carbohydrates, such as glucose, galactose, mannose, xylose, or arabinose or combinations thereof. Some starting materials may comprise mainly xylose (hemicelluloses), some may comprise mainly glucose (cellulose or starch), and some may comprise mainly mannose (galactoglucomannan based hemicelluloses).

Sugars, mannose, glucose, xylose, arabinose, and galactose need to be provided to microorganisms as monomeric sugars. The raw materials containing these sugars in polymeric form, e.g. lignocelluloses, can be treated with any known method to hydrolyse the sugar polymers into monomeric sugars that are utilizable by microorganisms according to the present invention.

In the cultivation of *Cupriavidus* or *Ralstonia* can be used any cultivation medium comprising components suitable for *Cupriavidus* or *Ralstonia* growth.

In industrial applications the cultivation medium typically comprises monomeric sugars orinating from lignocellulosic materials as carbon source, and in addition usually nutrients and salts or components thereof as micro- and macronutrients, and water. A cultivation medium may comprise mannose, glucose, galactose, xylose, or arabinose or any combination thereof as carbon source, typically as the main carbon source, in some embodiments as the sole carbon source.

In the cultivation of *Cupriavidus* or *Ralstonia* can be used cultivation conditions suitable for cultivation of *Cupriavidus* or *Ralstonia*. Such cultivation conditions are well known to a person skilled in the art. In the cultivation can be used liquid or solid media. Liquid cultures may be agitated, suitable agitation 50-1000 rpm, typically 100-600 rpm. The cultivation temperature may be 15 to 45° C., preferably 25 to 37° C., typically 30° C. The incubation time may be 1 day to 14 days, typically 2 to 7 days, preferably 24 to 72 hours. The cultivation may be a batch, fed-batch or continued cultivation.

The term "endogenous gene" refers here to a gene which is natural to the *Cupriavidus* or *Ralstonia* host.

The term "exogenous gene" refers here to a gene which is not natural to the *Cupriavidus* or *Ralstonia* host.

The genes introduced into the *Ralstonia* or *Cupriavidus* host may be endogenous or exogenous, typically they are exogenous, if/since the host does not possess the genes naturally. In some embodiments the endogenous genes naturally produced by the host may be overexpressed in the host for example by expressing the coding region under a strong promoter.

A gene encoding "phosphomannose isomerase" may be any gene which encodes an enzyme having phosphomannose isomerase activity. According to Enzyme Classification the enzyme has EC number 5.3.1.8. In a specific embodiment of the invention the gene may be a gene encoding phosphomannose isomerase (PMI) or mannose-6-phosphate isomerase from *Escherichia coli* strain K12 (EC 5.3.1.8) (ACCESSION No. P00946) (gene name: pmi, origin: *Escherichia coli* strain K12) (SEQ ID NO:1).

A gene encoding "facilitated diffusion protein for mannose uptake" may be any gene which encodes facilitated diffusion protein for mannose uptake activity (EC 1.3.1.74) or a gene encoding xylose proton symporter E. In a specific embodiment of the invention the gene may be a gene encoding glucose facilitated diffusion transporter (GLF) from *Zymomonas mobilis* (EC 1.3.1.74) (ACCESSION No. P21906) (gene name: glf, origin: *Zymomonas mobilis*) (SEQ ID NO:2). Surprisingly, a *Ralstonia* or *Cupriavidus* host introduced to express a gene encoding facilitated diffusion protein for mannose uptake activity, in particular glf, can use glucose as carbon source.

A gene encoding "mannofructokinase" may be any gene which encodes mannofructokinase (EC 2.7.1.4) activity. In a specific embodiment of the invention the gene may be a gene encoding mannofructokinase (MAK) (EC 2.7.1.4) from *Escherichia coli*, in particular from strain K12 (ACCESSION No. P23917) (gene name: mak, origin: *Escherichia coli* strain K12) (SEQ ID NO:3).

A gene encoding "xylose isomerase" may be any gene, which encodes xylose isomerase (EC 5.3.1.5) activity. In a specific embodiment of the invention the gene may be a gene encoding D-xylose isomerase (XylA) from *Escherichia coli* strain K12 (ACCESSION No. P00944) (EC 5.3.1.5) (gene name: xylA, origin: *Escherichia coli* strain K12) (SEQ ID NO:4).

A gene encoding "xylulokinase" may be any gene, which encodes xylulokinase activity (EC 2.7.1.17). In a specific embodiment of the invention the gene may be a gene encoding xylulose kinase (XylB) from *Escherichia coli* strain K12 (ACCESSION No. P09099) (EC 2.7.1.17) (gene name: xylB, origin: *Escherichia coli* strain K12) (SEQ ID NO:5).

A gene encoding "xylose proton symporter E" may be any gene, which encodes xylose proton symporter E. In a specific embodiment of the invention the gene may be a gene encoding D-xylose-proton symporter (XylE) from *Escherichia coli* strain K12 (gene name: xylE, origin: *Escherichia coli* strain K12) (ACCESSION No. P0AGF4) (SEQ ID NO:6).

A gene encoding "high affinity ABC-transporter" may be any gene, which encodes high affinity ABC-transporter. In a specific embodiment of the invention the gene may be a gene encoding D-xylose-binding periplasmic protein (XylF) from *Escherichia coli* strain K12 (gene name: xylF, origin: *Escherichia coli* strain K12) (ACCESSION No. P37387) (SEQ ID NO:7), or a gene encoding xylose import ATP-binding protein (XylG) from *Escherichia coli* strain K12 (gene name: xylG, origin: *Escherichia coli* strain K12) (AC-CESSION No. P37388) (EC 3.6.3.17) (SEQ ID NO:8), or a gene encoding xylose transport system permease protein (XylH) from *Escherichia coli* strain K12 (gene name: xylH, origin: *Escherichia coli* strain K12) (ACCESSION No. P0AGI4) (SEQ ID NO:9). Surprisingly, a *Ralstonia* or *Cupriavidus* host introduced to express genes, which encode high affinity ABC-transporter, in particular genes encoding XyI F, XyI G and XyI H, can use glucose and galactose as carbon source.

A gene encoding "transaldolase" may be any gene, which encodes transaldolase (EC 2.2.1.2). In a specific embodiment of the invention the gene may be a gene encoding transaldolase B (TalB) from *Escherichia coli* strain K12 (gene name: talB, origin: *Escherichia coli* strain K12) (ACCESSION No. BAB96586) (EC 2.2.1.2) (SEQ ID NO:10).

A gene encoding "ketolase" may be any gene, which encodes transketolase (EC 2.2.1.1). In a specific embodiment of the invention the gene may be a gene encoding transketolase 1 (TktA) from *Escherichia coli* strain K12 (gene name: tktA, origin: *Escherichia coli* strain K12) (ACCESSION No. P27302) (EC 2.2.1.1) (SEQ ID NO: 11).

A gene encoding "glucokinase" may be any gene, which encodes glucokinase (EC 2.7.1.2). In a specific embodiment of the invention the gene may be a gene encoding glucokinase (glk) from *Escherichia coli* strain K12 (gene name: glk, origin: *Escherichia coli* strain K12) (ACCESSION No, P0A6V8.1) (EC 2.7.1.2) GLK_ECOLI RecName: Full=Glucokinase; AltName: Full=Glucose kinase [*Escherichia coli* K-12] (SEQ ID NO: 12).

A *Ralstonia* or *Cupriavidus* host introduced to express glucokinase is capable of utilizing glucose.

Within the scope of the present invention is any gene, the gene product of which is known to catalyze the reaction of interest. Within the scope of the present invention are also genes, which encode the same or equivalentic function and are highly homologous to the genes of interest. This means, for example, that the proteins encoded by the genes have high identity % when compared to each other.

For example the following genes may be used:

The respective genes from different *Escherichia* strains (e.g. *Escherichia albertii* [phosphomannose isomerase ZP_02903372.1, mannose-6-phosphate isomerase, class I [*Escherichia albertii* TW07627] (SEQ ID NO:13); mannofructokinase ZP_02902328.1, manna kinase [*Escherichia albertii* TW07627] (SEQ ID NO:14); *Escherichia fergusonii* [phosphomannose isomerase YP_002382576.1, mannose-6-phosphate isomerase [*Escherichia fergusonii* ATCC 35469] (SEQ ID NO:15); xylose isomerase YP_002384641.1]) xylose isomerase [*Escherichia fergusonii* ATCC 35469] (SEQ ID NO:16); *Shigella* strains (e.g. *Shigella flexneri* [phosphomannose isomerase NP_837299.1], mannose-6-phosphate isomerase [*Shigella flexneri* 2a str. 2457T] (SEQ ID NO:17); *Shigella sonnei* [phosphomannose isomerase YP_310481.1, mannose-6-phosphate isomerase [*Shigella sonnei* Ss046] (SEQ ID NO:18); xylose isomerase YP_312597.1] xylose isomerase [*Shigella sonnei* Ss046] (SEQ ID NO:19); *Shigella dysenteriae* [phosphomannose isomerase ZP_03064125.1, mannose-6-phosphate isomerase, class I [*Shigella dysenteriae* 1012] (SEQ ID NO:20); mannofructokinase ZP_03064822.1, manno(fructo)kinase [*Shigella dysenteriae* 1012] (SEQ ID NO:21); xylose isomerase ZP_03063610.1]), xylose isomerase [*Shigella dysenteriae* 1012] (SEQ ID NO:22); *Citrobacter* strains (e.g. *Citrobacter koseri* [phosphomannose isomerase P_001453192.1, hypothetical protein CKO_01624 [*Citrobacter koseri* ATCC BAA-895] (SEQ ID NO:23); xylose isomerase YP_001456500.1], xylose isomerase [*Citrobacter* koseri ATCC BAA-895] (SEQ ID NO:24); *Citrobacter rodentium* [phosphomannose isomerase YP_003365034, mannose-6-phosphate isomerase [*Citrobacter rodentium* ICC168] (SEQ ID NO:25); mannofructokinase YP_003364074.1, probable manno(fructo)kinase [*Citrobacter* rodentium ICCM] (SEQ ID NO:26); xylose isomerase YP_003367655.1], D-xylose isomerase [*Citrobacter rodentium* ICC168] (SEQ ID NO:27); *Citrobacter youngae* [phosphomannose isomerase ZP_06352970.2, mannose-6-phosphate isomerase, class I [*Citrobacter youngae* ATCC 29220] (SEQ ID NO:28); xylose isomerase ZP_06571492.1]), xylose isomerase [*Citrobacter youngae* ATCC 29220] (SEQ ID NO:29); *Salmonella* strains (e.g. *Salmonella enterica* [phosphomannose isomerase YP_002146578.1, mannose-6-phosphate isomerase, class I [*Salmonella enterica* subsp. *enterica* serovar Agona str. SL483] (SEQ ID NO:30; xylose isomerase ZP_02342859.1], xylose isomerase [*Salmonella enterica* subsp, *enterica* serovar Saintpaul str. SARA29] (SEQ ID NO:31); *Salmonella typhimurium* [phosphomannose isomerase CAA40399.1]), phosphomannose isomerase [*Salmonella typhimurium*] (SEQ ID NO:32); *Enterobacter* strains (e.g. *Enterobacter cloacae* [phosphomannose isomerase ABF71065.1, mannose-6-phosphate isomerase [*Enterobacter cloacae*](SEQ ID NO:33); xylose isomerase YP_003610718.1], xylose isomerase [*Enterobacter cloacae* subsp. *cloacae* ATCC 13047] (SEQ ID NO:34); *Enterobacter cancerogenus* [phosphomannose isomerase ZP_05967481.1]), mannose-6-phosphate isomerase, class I [*Enterobacter cancerogenus* ATCC 35316] (SEQ ID NO:35); *Cronobacter* strains (e.g. *Cronobacter turicensis* [phosphomannose isomerase YP_003210382.1], mannose-6-phosphate isomerase [*Cronobacter turicensis* 23032] (SEQ ID NO:36); *Cronobacter sakazakii* [phosphomannose isomerase YP_001438057.1]), hypothetical protein ESA_01965 [*Cronobacter sakazakii* ATCC BAA-894] (SEQ ID NO:37); *Klebsiella* strains (e.g. *Klebsiella pneumoniae* [phosphomannose isomerase YP_002238770.1, mannose-6-phosphate isomerase, class I [*Klebsiella pneumoniae* 342] (SEQ ID NO:38); mannofructokinase YP_002240149.1]), manno(fructo)kinase [*Klebsiella pneumoniae* 342] (SEQ ID NO:39); *Serratia* strains (e.g. *Serratia odorifera* [phosphomannose isomerase ZP_06640499.1]), mannose-6-phosphate isomerase [*Serratia odorifera* DSM 4582] (SEQ ID NO:40).

Furthermore, the following genes may be used:
D-xylose transporter XylE [*Escherichia fergusonii* ATCC 35469] YP_002385136.1 (SEQ ID NO: 41);
D-xylose transporter XylE [*Shigella flexneri* 2a str. 301] NP_709888.1 (SEQ ID NO: 42);
D-xylose-proton symporter (D-xylose transporter) [*Salmonella enterica* subsp. *enterica* serovar Schwarzengrund str. SL480], Xyl E, ZP_02664392.1 (SEQ ID NO: 43);
sugar transporter family protein [*Citrobacter youngae* ATCC 29220], Xyl E, ZP_06356420.1 (SEQ ID NO: 44);
D-xylose:proton symporter [*Acidobacterium capsulatum* ATCC 51196], Xyl E, YP_002753901.1 (SEQ ID NO: 45):
xylulokinase [*Shigella flexneri* 2a str. 301] NP_709351.1 (SEQ ID NO: 46); xylulose kinase [*Citrobacter rodentium* ICC168] YP_003367656.1 (SEQ ID NO: 47);
D-xylose transporter subunit XylF [*Shigella flexneri* 5 str. 8401] YP_691285.1 (SEQ ID NO: 48);
D-xylose transporter subunit XylF [*Citrobacter koseri* ATCC BAA-895] YP_001456501.1 (SEQ ID NO: 49);
D-xylose ABC transporter, ATP-binding protein [*Shigella boydii* CDC 3083-94] YP_001882237.1 Xyl G, (SEQ ID NO: 50);
D-xylose ABC transporter, periplasmic D-xylose-binding protein [*Klebsiella pneumoniae* 342], Xyl G, YP_002236058.1 (SEQ ID NO: 51);
xylose transporter ATP-binding subunit [*Citrobacter koseri* ATCC BAA-895]YP_001456502.1, Xyl G, (SEQ ID NO: 52);
D-xylose ABC transporter, permease protein [*Shigella dysenteriae* 1012] ZP_03063638.1, Xyl H, (SEQ ID NO: 53);
inner-membrane translocator [*Enterobacter cloacae* subsp. *cloacae* ATCC 13047] YP_003610715.1, Xyl H, (SEQ ID NO: 54);
glucokinase [*Shigella dysenteriae* 1012] ZP_03065183.1 (SEQ ID NO: 55);
glucokinase [*Escherichia fergusonii* ATCC 35469]YP_002381954.1 (SEQ ID NO: 56);
transaldolase [*Shigella dysenteriae* 1012] ZP_03066451.1 (SEQ ID NO: 57);
transaldolase B [*Escherichia fergusonii* ATCC 35469] YP_002381239.1 (SEQ ID NO: 58);
transketolase [*Shigella dysenteriae* 1012] ZP_03063878.1 (SEQ ID NO: 59);
transketolase [*Escherichia fergusonii* ATCC 35469] YP_002383968.1 (SEQ ID NO: 60)
can be used in the invention.

Alternative sources for various genes encoding the desired enzyme activities are for example:
Alternative Sources for Glucokinases:
glucokinase [*Shigella boydii* Sb227]Yp_408803.1
glucokinase [*Escherichia albertii* TW07627]ZP_02901664.1
glucokinase [*Salmonella enterica* subsp. *enterica* serovar Typhimurium str. LT2] NP_461344.1
glucokinase [*Citrobacter youngae* ATCC 29220]ZP_06351950.1
Glucokinase [*Citrobacter rodentium* ICC168]YP_003366335.1
glucokinase [*Enterobacter cloacae* subsp. *cloacae* NCTC 9394] CBK87115.1
glucokinase [*Citrobacter koseri* ATCC BAA-895] YP_001452005.1
glucokinase [*Cronobacter sakazakil* ATCC BAA-894]YP_001436959.1
glucokinase [*Enterobacter cancerogenus* ATCC 35316]ZP_05968594.1
glucokinase [*Klebsiella pneumoniae* subsp. *pneumoniae* MGH 78578] YP_001336384.1
glucokinase [*Serratia odorifera* DSM 4582] ZP_06639362.1
Glucokinase [*Erwinia billingiae* Eb661] CAX60782.1
Glucokinase [*Erwinia amylovora* CFBP1430] YP_003531826.1
Alternative Sources for Mannofructokinases are for Example:
fructokinase [*Shigella sonnei* Ss046] YP_309383.2
hypothetical protein CKO_02777 [*Citrobacter* koseri ATCC BAA-895] YP_0014543191
fructokinase [*Enterobacter* sp. 638] YP_001175599.1
fructokinase [*Escherichia fergusonii* ATCC 35469] YP_002383736.1
fructokinase [*Enterobacter cloacae* subsp. *cloacae* ATCC 13047] YP_003611661.1
Alternative Sources for Facilitated Diffusion Transporter, GLF and XylE are for Example:
D-xylose transporter XylE [*Shigella sonnei* Ss046]YP_312943.1
xylose-proton symport [*Citrobacter* sp. 30_2] ZP_04558597.1 sugar transporter family protein [*Citrobacter youngae* ATCC 29220] ZP_06356420.1
D-xylose transporter XylE [*Salmonella enterica* subsp. *arizonae serovar* 6224,z23:-] YP_001572426.1
D-xylose-proton symporter (D-xylose transporter) [*Citrobacter rodentium* ICC168] YP_003367154.1
D-xylose transporter XylE [*Mannheimia succiniciproducens* MBEL55E] YP_089566.1
D-xylose transporter XylE [*Actinobacillus succinogenes* 130Z] YP_001343806.1
D-xylose transporter XylE [*Bacillus cereus* ATCC 10987] NP_978526.1
xylose permease [*Bacillus megaterium* DSM319] YP_003597063.1

Due to high homology between facilitated diffusion protein for mannose uptake (EC1.3.1.74), in particular GLF, and xylose proton symporter E, xyl E, genes encoding xylose proton symporter E, xyl E, may be used instead of genes encoding facilitated diffusion protein for mannose uptake, and vice versa.

Alternative Sources for Xylulokinases are for Example:
xylulokinase [*Shigella* sp. D9] ZP_05434777.1
xylulokinase [*Escherichia fergusonii* ATCC 35469] YP_002384640.1
xylulokinase [*Citrobacter* sp. 30_2] ZP_04559359.1
xylulokinase [*Shigella boydii* Sb227] YP_409882.1
xylulose kinase [*Salmonella enterica* subsp. *enterica serovar* Paratyphi C strain RKS4594]YP_002639258.1
hypothetical protein CKO_05020 [*Citrobacter koseri* ATCC BAA-895] Yp_001456499.1
xylulokinase [*Shigella sonnei* Ss046] YP_312598.1
xylulokinase [*Citrobacter youngae.* ATCC 29220] ZP_06355683.1
xylulokinase [*Klebsiella* sp. 1_1_55] ZP_06551221.1
hypothetical protein ECL_00202 [*Enterobacter cloacae* subsp. *cloacae* ATCC 13047] YP_003610719.1
xylulokinase [*Klebsiella pneumoniae* 342] YP_002236061.1
xylulokinase [*Klebsiella variicola* At-22]YP_003437118.1
Xylulose kinase [*Cronobacter turicensis* z3032] YP_003212435.1
Xylulose kinase [*Yersinia intermedia* ATCC 29909] ZP_04636833.1
Xylulokinase [*Erwinia billingiae* Eb661] CAX60830.1
xylulokinase [*Serratia odorifera* DSM 4582] ZP_06638097.1

Alternative Sources for XylF are for Example:
D-xylose transporter subunit XylF [*Shigella boydii* Sb227] YP_409884.1
D-xylose transporter subunit XylF [*Enterobacter* sp. 638] YP_001174896.1
D-xylose transporter subunit XylF [*Cronobacter sakazakii* ATCC BAA-894]YP_001440178.1
D-xylose-binding periplasmic protein [*Cronobacter turicensis* z3032] YP_003212438.1
D-xylose transporter subunit XylF [*Enterobacter cloacae* subsp. *cloacae* ATCC 13047] YP_003610717.1
hypothetical protein ENTCAN_08293 [*Enterobacter cancerogenus* ATCC 35316] ZP_05969667.2
D-xylose ABC transporter, periplasmic substrate-binding protein [*Erwinia billingiae* Eb661] CAX60828.1
xylose ABC superfamily ATP binding cassette transporter, binding protein [*Serratia odorifera* DSM 4582] ZP_06638100.1
D-xylose transporter subunit XylF [*Actinobacillus succinogenes* 130Z] YP_001343809.1

Alternative Sources for XylG are for Example:
xylose transporter ATP-binding subunit [*Shigella flexneri* 5 str. 8401] YP_691284.1
D-xylose ABC transporter, ATP-binding protein [*Shigella dysenteriae* 1012] ZP_03063359.1
xylose transporter ATP-binding subunit [*Enterobacter cloacae* subsp. *cloacae* ATCC 13047] YP_003610716.1
D-xylose ABC transporter, ATP-binding protein [*Klebsiella pneumoniae* 342] YP_002236058.1
hypothetical protein ENTCAN_08292 [*Enterobacter cancerogenus* ATCC 35316] ZP_05969666.1
xylose transporter ATP-binding subunit [*Cronobacter sakazakii* ATCC BAA-894] YP_001440177.1
Xylose import ATP-binding protein xylG [*Cronobacter turicensis* z3032] YP_003212439.1
D-xylose ABC transporter, ATPase subunit [*Erwinia billingiae* Eb661] CAX60827.1 xylose ABC superfamily ATP binding cassette transporter, ABC protein [*Serratia odorifera* DSM 4582] ZP_06638101.1
COG1129: ABC-type sugar transport system, ATPase component [*Actinobacillus pleuropneumoniae serovar* 1 str. 4074] ZP_001349182

Alternative Sources for XylH are for Example:
hypothetical protein CKO_05024 [*Citrobacter koseri* ATCC BAA-895]YP_001456503.1
xylose ABC transporter membrane protein [*Enterobacter cloacae* subsp. *cloacae* NCTC 9394] CBK87790.1
hypothetical protein ENTCAN_08291 [*Enterobacter cancerogenus* ATCC 35316] ZP_05969665.1
inner-membrane translocator [*Enterobacter* sp. 638] YP_001174894.1
hypothetical protein ESA_04159 [*Cronobacter sakazakii* ATCC BAA-894]YP_001440176.1
D-xylose ABC transporter, permease protein [*Klebsiella pneumoniae* 342] YP_002236057.1
Xylose transport system permease protein xylH *Cronobacter turicensis* z3032] YP_003212440.1
sugar transport system permease protein [*Yersinia enterocolitica* subsp. *enterocolitica* 8081] YP_001008391.1
D-xylose ABC transporter, permease protein [*Erwinia billingiae* Eb661]CAX60826.1
monosaccharide-transporting ATPase [*Serratia proteamaculans* 568] YP_001476339.1
xylose ABC superfamily ATP binding cassette transporter, membrane protein [*Serratia odorifera* DSM 4582] ZP_06638102.1
monosaccharide-transporting ATPase [*Actinobacillus succinogenes* 130Z] YP_001343807.1

Alternative Sources for Transaldolase are for Example
transaldolase B [*Shigella boydii* Sb227] YP_406573.1
transaldolase [*Citrobacter youngae* ATCC 29220] ZP_06354813.1
transaldolase B [*Citrobacter koseri* ATCC BAA-895] YP_001454897.1
transaldolase B [*Salmonella enterica* subsp. *arizonae serovar* 62:z4,z23:-YP_001571972.1
transaldolase B [*Citrobacter rodentium* ICC168] YP_003363651.1
transaldolase B [*Enterobacter* sp. 638] YP_001175308.1
hypothetical protein ENTCAN_05194 [*Enterobacter cancerogenus* ATCC 35316]ZP_05966848.1
transaldolase B [*Citrobacter* sp. 30_2] ZP_04559788.1
transaldolase [*Enterobacter cloacae* subsp. *cloacae* NCTC 9394] CBK87626.1
transaldolase B [*Klebsiella pneumoniae* 342] YP_002240539.1
transaldolase B [*Enterobacter cloacae* subsp. *cloacae* ATCC 13047]YP_003611333.1 transaldolase B [*Cronobacter sakazakii* ATCC BAA-894] YP_001439387.1
transaldolase B [*Cronobacter turicensis* z3032] YP_003208998.1
transaldolase [*Escherichia albertii* TW07627] ZP_02902842.1
transaldolase [*Yersinia kristensenii* ATCC 33638] ZP_04625574.1
transaldolase A [*Serratia odorifera* DSM 4582] ZP_06637249.1
transaldolase B [*Erwinia amylovora* CFBP1430] YP_003532302.1
transaldolase B [*Erwinia amylovora* ATCC 49946] YP_003537736.1
transaldolase B [*Erwinia pyrifoliae* DSM 12163] CAY73102.1
Alternative Transketolases are for Example:
transketolase [*Shigella flexneri* 2a str. 24571] NP_838419.1
transketolase [*Shigella boydii* CDC 3083-94] YP_001881708.1
transketolase [*Escherichia albertii* TW07627] ZP_02900973.1
transketolase [*Citrobacter koseri* ATCC BAA-895] YP_001455802.1
transketolase [*Citrobacter* sp. 30_2] ZP_04560349.1
transketolase [*Citrobacter youngae* ATCC 29220] ZP_06355044.1
transketolase [*Enterobacter cancerogenus* ATCC 35316] ZP_05970189.1
transketolase [*Enterobacter cloacae* subsp. *cloacae* NCTC 9394] CBK86553.1
transketolase [*Klebsiella pneumoniae* subsp. *pneumoniae* MGH 78578] YP_001336984.1
transketolase 1 [*Citrobacter rodentium* ICC168] YP_003368408.1
transketolase [*Klebsiella variicola* At-22] YP_003440166.1
transketolase [*Klebsiella pneumoniae* 342] Yp_002239249.1
Transketolase 1 [*Cronobacter turicensis* z3032]YP_003211835.1
transketolase [*Cronobacter sakazakii* ATCC BAA-894] YP_001436540.1
transketolase [*Enterobacter cloacae* subsp. *cloacae* ATCC 13047]YP_003614730.1
transketolase [*Erwinia tasmaniensis* Et1/99] YP_001908733.1
transketolase [*Serratia odorifera* DSM 4582] ZP_06641778.1

The accession numbers are derived from NCBI database (National Center for Biotechnology information, U.S. National Library of Medicine, 8600 Rockville Pike, Bethesda Md., 20894 USA). The date of providing the accession numbers was 2nd June 2010.

Within the scope of the present invention are proteins encoded by any of the above listed genes, in particular those comprising the amino acid sequences SEQ ID NO:1 to 60, preferably sequences SEQ ID NO: 1 to 12.

It is evident that small variations in the nucleotide sequence of a gene do not significantly change the catalytic properties of the encoded protein. For example many changes in the nucleotide sequence do not change the amino acid sequence of the encoded protein. Also an amino acid sequence may have variations, which do not change the functional properties of a protein, in particular they do not prevent an enzyme from carrying out its catalytic function. As it is known to a person skilled in the art, variations can exist or can be made to regions which are outside of the region critical to the function of the enzyme and still result in an active polypeptide. Such variations in the nucleotide sequence or DNA molecules or in an amino acid sequence are known as "functional equivalents", because they do not significantly change the function of the gene to encode a protein with a particular function, e.g. catalyzing a particular reaction or, respectively, change the particular function of the protein. Within the scope of the present invention are functional equivalents, including fragments or derivatives, or closest homologues of the listed proteins, in particular functional equivalents of sequences SEQ ID NO: 1 to 60, preferably sequences SEQ ID NO: 1 to 12.

Within the scope of the present invention are genes encoding amino acid sequences showing at least 50%, preferably at least 60% identity, preferably at least 65%, preferably at least 70%, preferably at least 75%, preferably at least 80%, preferably at least 85%, more preferably at least 90%, still more preferably at least 95%, more and more preferably at least 98% identity to any of the amino acid sequences of the above listed proteins, in particular sequences SEQ ID NO: 1 to 60, preferably sequences SEQ ID NO: 1 to 12.

Within the scope of the present invention are genes encoding proteins comprising any of the amino acid sequences SEQ ID NO:1 to 60, preferably sequences SEQ ID NO: 1 to 12.

Within the scope of the present invention are also genes encoding amino add sequences showing at least 50%, preferably at least 60% identity, preferably at least 65%, preferably at least 70%, preferably at least 75%, preferably at least 80%, preferably at least 85%, more preferably at least 90%, still more preferably at least 95%, more and more preferably at least 98% identity to any of the amino acid sequences SEQ ID NO:1 to 60, preferably sequences SEQ ID NO: 1 to 12. The term "identity" refers to the identity between two nucleic acid or amino acid sequences, respectively compared to each other from the first nucleic acid to the last nucleic acid or from the first amino acid encoded by the corresponding gene to the last amino acid. The identity of the full-length sequences can be measured by using BLAST program (Altschul, S. F., T. L. Madden, A. A. Schäffer, J. Zhang, Z. Zhang, W. Miller and D. J. Lipman 1997. Gapped BLAST and PSI-BLAST: a new generation of protein database search programs. Nucleic Acids Res. 25:3389-3402). In the comparison is preferably used the mature sequences of the proteins.

Bacteria belonging to genus *Cupriavidus* or *Ralstonia* and capable of expressing genes encoding phosphomannose isomerase and facilitated diffusion protein for mannose uptake or xylose proton symporter E and optionally mannofructokinase are capable of growing on mannose as the carbon source. A *Cupriavidus* host introduced to express a gene encoding facilitated diffusion protein for mannose uptake activity, in particular glf, can use also glucose as carbon source.

Mannose can be found in wood and plant materials, especially in hemicelluloses of soft woods (e.g. pine or spruce) consisting of galactoglucomannane polymer, in some fruits or berries (e.g. cranberry), and in cell structures of various microorganisms such as fungi (yeasts and filamentous fungi) and microalgae (e.g. *Chlorella, Nannochloropsis* and *Phaeodacylum*).

Bacteria belonging to genus *Cupriavidus* or *Ralstonia* and capable of expressing genes encoding xylose isomerase and xylulokinase and a high affinity ABC-transporter or xylose proton symporter E are capable of growing on xylose or xylose and arabinose as the carbon source. A *Cupriavidus* host introduced to express genes, which encode high affinity ABC-transporter, in particular genes encoding Xyl F, Xyl G and Xyl H, are able to use also glucose and galactose as carbon source.

In addition the microorganism may be genetically modified to express transaldolase and/or transketolase making the growth of the microorganism faster.

As is described herein a microorganism introduced to express a gene encoding facilitated diffusion protein for mannose uptake is capable of using also glucose. This is achieved in particular by gene glf.

The microorganism host is capable of utilizing glucose also, if to the host is introduced to express a gene encoding glucokinase EC 2.7.1.2).

In one embodiment a microorganism according to this disclosure is capable of utilizing one or more of mannose, glucose, galactose, xylose and/or arabinose as carbon source.

In one embodiment a microorganism according to this disclosure is capable of utilizing mannose and optionally glucose as carbon source.

In one further embodiment a microorganism according to this disclosure is capable of utilizing xylose, or xylose and arabinose, and optionally glucose and/or galactose as carbon source.

A microorganism introduced to express xylose isomerase, xylulokinase and a high affinity ABC-transporter or xylose protein symporter E, is capable of utilizing xylose. Surprisingly, the microorganism host is capable of utilizing also arabinose. To the best knowledge of the present inventors, this is the first time a *Ralstonia* or *Cupriavidus* host has obtained the capability to use arabinose. In the prior art Buchholz et al. (1994) transferred an *Alcaligenes eutrophus* host by a 28-kb insert, 16.4 of which comprised the minimal information required for xylose utilization by *A. eutrophus*. Buchholz et al. assumed that the xyl genes encoding xylose isomerase and xylulokinase were located within this region, since they were induced during growth on xylose. Buchholz et al. obtained three transconjugants which grew on xylose as sole source of carbon and energy, but ribose or arabinose-utilizing strains were not obtained. As herein disclosed the microorganism host has been introduced to express inserts which consist essentially of nucleotide sequences needed for xylose utilization. Surprisingly the constructions make the host capable of utilizing also arabinose.

A microorganism introduced to express a high affinity ABC-transporter, in particular genes encoding Xyl F, Xyl G and Xyl H, is surprisingly capable of using also glucose and galactose as carbon source.

The activity of MAK (mannofructokinase), PMI (phosphomannose isomerase), GLK (glucokinase) can be assayed by methods well known in the art. Soluble protein fractions of recombinant host strain can be applied for MAK, PMI and GLK activity measurements at 30° C. using a Nicolet Evolution™ 100 UV/VIS spectrophotometer (Thermo Electron Corporation, Cambridge, UK). Activity of MAK can be assayed with an NADH-coupled system as described by Sebastian and Asensio (1972) with some modifications as described in the examples.

PMI activity can be measured with an NADP-coupled assay (Kang and Markovitz 1967) with some modifications as described in the examples.

GLK activity can be measured with an NADPH-coupled system according to the method of Gottschalk (Gottschalk et al. 1964) with modifications as described in the examples.

XylA and XylB activity can be assayed by methods well known in the art. Soluble protein tractions or recombinant host strain can be applied for XylA and XylB activity measurements at 30° C. using a Nicolet Evolution™ 100 UV/VIS spectrophotometer (Thermo Electron Corporation, Cambridge, UK). Activity of XylA (Gao et al, 2002, Mejnen et al. 2008) or XylB (Shamanna and Sangerson 1979, Eliasson et al. 2000) can be assayed with an NADH-coupled system with some modifications, using sorbitol dehydrogenase or pyruvate kinase and lactate dehydrogenase, respectively, as auxiliary enzymes as described in the examples.

"Regulatory elements" refer here to regulatory elements which can regulate the expression of a foreign gene introduced into a host cell, here in particular into *Cupriavidus* or *Ralstonia*. Regulatory elements include promoters, terminators, enhancers and signal sequences.

"Vector" refers here to a nucleic acid molecule, typically a DNA molecule, which can be used to transfer foreign genetic material into a host cell. A vector may be a plasmid, bacteriophage, virus or cosmid, here it is typically a plasmid. Preferably the vector is a broad host range vector. In one embodiment the vector may be an episomal vector not incorporated to the genome of the host cell. In another embodiment the vector may be integrated into the genome of the host cell.

Broad-host-range plasmids permit replication in diverse bacterial species and are not restricted to bacteria of a certain genus or species.

In one embodiment of the invention a vector may comprise a gene encoding phosphomannose isomerase, a gene encoding facilitated diffusion protein for mannose uptake, a gene encoding xylose proton symporter E and/or a gene encoding mannofructokinase. The genes may be in the same or in separate vectors.

In another embodiment of the invention a vector may comprise a gene encoding xylose isomerase, xylulokinase, xylose proton symporter E, and/or a high affinity ABC-transporter A. The genes may be in the same or in separate vectors.

In one embodiment of the invention the vector may be a broad host range vector, This provides the advantage that the extension of the substrate range can be achieved with the broad host range vectors in any species or strains of *Cupriavidus* or *Ralstonia*.

Preferably the vector is a high copy number vector.

Furthermore, the vector comprises regulatory elements, in particular a promoter, for regulating expression of said genes in *Cupriavidus* or *Ralstonia*. Preferably the vector comprises a strong promoter for expression of the desired genes in *Cupriavidus* or *Ralstonia*.

In one embodiment regulatory elements in the vector may comprise neokanamycin-promoter, lac-promoter, or glyceraldehyde-3-phophate dehydrogenase promoter. In addition, the following promoters can be used: promoter P2, typically from *Pseudomonas syringae* (Solaiman and Swingle 2010), in particular of plasmid pBS29-P2 (Solaiman et al. 2010), the hydrogenase (SH) promoter, typically from *R. eutropha* (Porthun et al. 2002, Schwartz et al. 1998), and the promoter $P_L$, typically from the cbb operon (Jeffke at al. 1999, Schäferjohann et al. 1996, Windhövel and Bowien 1990). Preferably the promoters are constitutive.

Suitable promoters are here in particular a constitutive lac-promoter ($P_{lac}$) (Siedow et al. 1999), neokanamycin-promoter ($P_{nk}$), glyceraldehyde-3-phosphate dehydrogenase (GAPDH) promoter ($P_{GAPDH}$).

Vectors, suitable for use in the invention are for example pBBR1MCS and its derivatives pBBR1MCS-2, pBBR1MCS-3, pBBR1MCS-4 and pBBR1MCS-5 (Kovach et al. 1995).

Furthermore, the shuttle plasmid pBHR1 can be used (MoBiTec GmbH, Göttingen, Germany) (Aneja at al. 2009) in the invention.

Plasmid pKT230 (Park at al. 1995), which is derived from the broad host range plasmid RSF1010 (Franklin et al. 1981) can also be used in the invention.

Also plasmid pBS29 (Swingle et al. 2008) or pBS29-P2 (Solaiman at al. 2010), which are derived from plasmid pUCP26 capable of replicating in *E. coli* and *Pseudomonas* species (West et al. 1994), can be used in this invention.

Within the scope of the present invention is also the production of desired chemicals by using the modified microorganisms according to the invention. The desired chemicals may be products naturally produced by the host, such as polyhydrolyalkanoates (Reinecke and Steinbüchel 2009 and Verlinden et al. 2007) or the host may be introduced to express the desired chemicals, for example lipids. Genes which can be used to genetically modify microorganism hosts to express various lipids has been disclosed in WO 2007136762. The capability of a *Cupriavidus* or *Ralstonia* host to produce lipids was exemplified by introducing a *Cupriavidus* or *Ralstonia* host to express fatty acid ethyl esters (FAEE). This was carried out by expressing in a polyhydroxy butyrate (PHB)-negative mutant of *R. eutropha* H16 host genes encoding wax ester synthase/diacylglycerol acyltransferase (atfA), pyruvate decarboxylase (pdc) and alcohol dehydrogenase B (adhB).

The benefit of this invention is an extended substrate utilization range of *Cupriavidus* or *Ralstonia* towards abundant and low-cost carbohydrates. The extension of substrate range was achieved by using broad host range plasmids, which make it possible to extend the substrate range in any species or strain of the *Cupriavidus* or *Ralstonia* host. By chemical methods it is possible to introduce a mutation only in a specific strain. Furthermore, in chemically induced mutants there is the risk of additional mutations that might affect the productiveness and/or may lead to unfavourable side effects.

The present invention was exemplified by constructing two different recombinant strains of *Ralstonia*, more specifically two *R. eutropha* H16 strains. The strains were developed to be capable of utilizing mannose/glucose, and xylose/arabinose respectively, by metabolic engineering. The induction of different gene in *R. eutropha*, necessary for either glucose/mannose uptake and utilization of mannose, or for xylose uptake and utilization, receptively, complemented the lacking parts of either glucose/mannose or xylose/arabinose catabolism, respectively. The recombinant strains of *R. eutropha* with the extended substrate utilization range synthesized poly(3-hydroxybutyrate) PHB from glucose, mannose, xylose and arabinose in similar amounts than from gluconate.

In one embodiment of the invention in *Cupriavidus* or *Ralstonia* may be expressed genes, which are responsive of sugar uptake and conversion. Hexokinases from other prokaryotes, such as *Leuconostoc mesenteroides* or *Streptomyces* sp., which also exhibit an activity for mannose (Anderson and Sapico 1975, Coulombel et al. 1982), may be expressed in *Cupriavidus* or *Ralstonia* to improve sugar conversion in the host. An overexpression of the chromosomally encoded hexokinase with its side activity for mannose may be used to enhance mannose utilization in *Ralstonia*. The pBBR plasmids used in the examples can be replaced for example with high copy number vectors and/or with stronger promoters (Kovach et al. 1995, Siedow et al. 1999), or other vectors more suitable for expression of the desired genes for mannose utilization. The lac-promoter may be replaced with a stronger constitutive promoter, for example the neokanamycin-promoter as described herein and which give elevated expression levels. The desired genes may also be integrated into the genome of *Cupriavidus* or *Ralstonia* giving advantages, such as stability. Furthermore, mutants containing marker-free integrations in their genomes are not subjected to any selection, which save costs especially for large scale cultivations.

According to one further embodiment the present invention provides a method, which comprises that the microorganism is allowed to synthesize bulk chemicals, such as lipids, for example polyhydroxyalkanoates, fatty acids or fatty acid derivatives, and the chemical is recovered from the cultivation medium or from the cells.

In the cultivation of *Cupriavidus* or *Ralstonia* can be used any cultivation medium comprising components suitable for *Cupriavidus* or *Ralstonia* growth. Typically they include a carbon and/or a nutrient source, salts, typically mineral salts, and water. Selection markers, such as antibiotic resistance genes may be needed to confirm the presence of desired genes in the host cells.

The substrate utilization of *Ralstonia* has been here exemplified by cultivating *Cupriavidus* or *Ralstonia* in a mineral salts medium (MSM) described by Schlegel et al. (1961). In industrial applications the cultivation medium typically comprises monomeric sugars urinating from lignocellulosic materials, as carbon source, and in addition possibly nutrients and salts or components thereof as micro- and macronutrients, and water.

In the cultivation of *Cupriavidus* or *Ralstonia* can be used cultivation conditions suitable for cultivation of *Cupriavidus* or *Ralstonia*. Such cultivation conditions are well known to a person skilled in the art. In the cultivation can be used liquid or solid media. Liquid cultures may be agitated, suitable agitation 50-1000 rpm, typically 100-600 rpm. The cultivation temperature is typically 15 to 45, preferably 25 to 37° C., typically 30° C. The incubation time may be 1 day to 14 days, typically 2 to 7 days, preferably 24 to 72 hours. The cultivation may be a batch, fed-batch or continued cultivation.

*Escherichia coli* and *Zymomonas mobilis* were cultivated by methods well known to a person skilled in the art and described in the examples.

As herein described recombinant *Ralstonia* strains and wild type strains were cultivated on different carbon sources. Cells were incubated on MSM agar plates containing 1% (wt/vol) of the respective carbon source for 5 days at 30° C. Visible colony growth was phenotypically examined. Characters: (++) growth after an incubation time of 24-72 h, (+) growth after more than 72 h of incubation, (−) no visible growth detectable. The use of the following carbon sources were examined: L-Arabinose, D-fructose, D-Galactose, D-Gluconate, D-Glucose, D-glycerol, D-maltose-mannitol, D-mannose, N-acetyl-D-glucosamine, pyruvate, D, ribose, D-trehalose and D-xylose.

The activity of MAK (mannofructokinase), PMI (phosphomannose isomerase), (glucokinase) can be assayed by methods well known in the art. Soluble protein fractions of recombinant host strain can be applied for MAK, PMI and GLK activity measurements at 30° C. using a Nicolet Evolution™ 100 UV/VIS spectrophotometer (Thermo Electron Corporation, Cambridge, UK). Activity of MAK can be assayed with an NADH-coupled system as described by Sebastian and Asensio (1972) with some modifications as described in the examples.

PMI activity can be measured with an NADP-coupled assay (Kang and Markovitz 1967) with some modifications as described in the examples.

GLK activity can be measured with an NADPH-coupled system according to the method of Gottschalk (Gottschalk et al. 1964) with modifications as described in the examples.

The present invention has been exemplified by generating recombinants of *R. eutropha* strain H16 which, in contrast to the wild type, were able to utilize mannose and/or glucose as sole carbon sources. Up to four genes (glf, glk, mak, pmi) were introduced episomally in *R. eutropha* strain H16 under control of a constitutive neokanamycin- or lac-promoter, enabling uptake and conversion of glucose and mannose into intermediates of the KDPG pathway.

Bacteria belonging to the genera *Ralstonia* and *Cupriavidus* typically have a very narrow substrate utilization spectrum and are only limited amount of sugars. E.g. the capability of *Ralstonia* eutropha H 16 to use carbohydrates and related compounds is limited to fructose, N-acetylglucosamine and Gluconate. To broaden the substrate utilization range of *Ralstonia* and *Cupriavidus* strains, the strains were engineered to use mannose as sole carbon source for growth.

The genes for a facilitated diffucion protein (glf) from *Zymomonas mobilis* and for mannofructokinase (mak), phosphomannose isomerase (pmi) and glucokinase (glk) from *E. coli* either alone or in combination constitutively expressed in *R. eutropha* under control of the lac-promoter, using an episomal broad host range vector. Recombinant strains harboring pBBR1MCS-3::glf::mak::pmi or pBBRMCS-3::glf::pmi grew on mannose, whereas pBBR1MCS-3::glf::mak and pBBR1MCS-3::glf did not confer the ability to utilize mannose as carbon source to *R. eutropha*. The recombinant strains harboring pBBR1MCS-3::glf::mak::pmi exhibited faster growth than pBBR1MCS-3::glf::pmi on mannose. These data indicated that phosphomannose isomerase is required to convert mannose-6-phosphate into fructose-6-phophate for subsequent catabolism via. Entner-Doudoroff pathway. In addition, surprisingly all plasmids conferred to *Ralstonia* also the ability to grow in the presence of glucose.

Furthermore, expression of the respective enzymes was demonstrated at the transcriptional level and by measuring the activities of mannofructokinase (0.14 U mg-1 protein), and phosphomannose isomerase (0.25 U mg-1 protein).

To identify genes in the genome of *R. eutropha* H16 coding for functional enzymes required for uptake and catabolism of D-xylose, a protein-protein-BLAST-analysis (Altschul et al. 1980) using an amino acid sequence database of *R. eutropha* H16 (Pohlmann et al. 2006) was performed. No genes encoding a transporter specific for D-xylose could be identified (Pohlmann et al. 2006). Also no genes encoding enzymes catabolizing D-xylose, e.g. a xylose isomerase or xylulose kinase, were identified. Indeed, *R. eutropha* H16 possesses genes for a fructokinase and a glucokinase (Pohlmann at al. 2006). All other genes, encoding enzymes of the non-oxidative pentose phosphate pathway for further catabolism of D-xylulose-5-phosphate are present in *R. eutropha* strain H16.

The construction of *Ralstonia* hosts to use xylose as sole carbon source for growth was exemplified by using *R. eutropha* strains. The genes for a low-affinity D-xylose-proton-symporter (xylE), a high-affinity ABC transporter (xylFGH), a xylose isomerase (xylA), and a xylulokinase (xylB), from *E. coli* were in combination constitutively expressed in *Ralstonia* hosts under control of a lac-promoter and glyceraldehyde-3-phosphate dehydrogenase (GADPH) promoter, respectively, using an episomal broad host range vector. Recombinant strains harboring pBBR1MCS-3::xylABFGH grew on xylose conferring the ability to utilize xylose as carbon source to *Ralstonia*. In addition, surprisingly, plasmids conferring xylose-utilization to *Ralstonia* conferred also the ability to grow in the presence of arabinose.

To exemplify the ability of recombinant *R. eutropha* strains to produce PHB from mannose or glucose, *Ralstonia* cells were cultivated under conditions permissive for PHB accumulation in MSM containing 1% (wt/vol) mannose, glucose or sodium gluconate as sole carbon source containing tetracycline or kanamycin, respectively, for selection and 0.05% (wt/vol) $NH_4Cl$. The PHB contents of the cells were analyzed gas chromatographically as described in the materials and methods section. Cultures containing gluconate as a sole carbon source served as a reference for the recombinant strain, and samples were taken in the early stationary growth phase. GC analysis of the cells revealed a PHB content of 63% (wt/wt) of cell dry mass. Cells grown in presence of 1% (wt/vol) glucose or mannose were also examined in the stationary growth phase, and PHB contents of 65 and 67% (wt/wt) of cell dry mass, respectively, were determined.

To exemplify the ability of recombinant *R. eutropha* strains to produce PHB from xylose and arabinose, cells were cultivated under conditions permissive for PHB accumulation in MSM containing 1% (wt/vol) D-xylose, L-arabinose or sodium gluconate as sole carbon source containing tetracycline, respectively, for selection and 0.05% (wt/vol) $NH_4Cl$. The PHB contents of the cells were analyzed gas chromatographically as described in the Examples in the materials and methods section. Cultures containing gluconate as a sole carbon source served as a reference for the recombinant strain, and samples were taken in the early stationary growth phase. GC analysis of the cells revealed that the cells were able to produce PHB. Cells grown in presence of 1% (wt/vol) L-arabinose or D-xylose were also examined in the stationary growth phase, and production of PHB was shown.

The recombinant strains of *R. eutropha* with the extended substrate utilization range were thus able to synthesize poly (3-hydroxybutyrate) PHB from glucose, mannose, xylose and arabinose in similar amounts than from gluconate.

EXAMPLES

Example 1

Materials and Methods

Bacterial Strains, Plasmids, Oligonucleotides and Cultivation Conditions.

Alt bacteria, plasmids and primers used in this application are listed in Table 1. Cells of *R. eutropha* strain H16 were cultivated in mineral salts medium (MSM) as described by Schlegel et al. (1961). Carbon sources were added to liquid MSM as indicated in the text. Liquid cultures in Erlenmeyer flasks were incubated on a horizontal rotary shaker at an agitation of 110 rpm. Solid media were prepared by addition of 1.5% (wt/vol) agar-agar, Cells of *Escherichia coli* were cultivated at 37° C. in Lysogeny Broth (LB) [Sambrook et al. 1989]. Cells of *Zymomonas mobilis* were cultivated in a medium containing 10 g/L. Bacto peptone, 10 g/L yeast extract, and 20 g/L glucose. Antibiotics were applied according to Sambrook at al. (1989) and as indicated in the text.

TABLE 1

Bacterial strains, plasmids and oligonucleotides

| Strain, plasmid or primer | Relevant characteristics | Source or reference |
|---|---|---|
| Strains | | |
| *E. coli* K-12 | Wild type | DSM 426 |
| *E. coli* TOP10 | F⁻ mcrA, Δ(mrr-hsdRMS-mcrBC) f80lacZ ΔM15, ΔlacX74, deoR, recA1, araD139, Δ(ara-leu)7697, galU, galK, rpsL, endA1, nupG | Invitrogen |
| *E. coli* S17-1 | recA1, thi1, hsdR17($r_k^-$, $m_k^+$), proA, tra-genes of RP4 plasmid chromosomally integrated (Mobilization strain) | Simon et al. 1983 |

TABLE 1-continued

Bacterial strains, plasmids and oligonucleotides

| Strain, plasmid or primer | Relevant characteristics | Source or reference |
|---|---|---|
| E. coli JE5511 | Hfr, manA4, lpp-1, pps-6 | E. coli Genetic Stock Center (Hirota et al. 1977) |
| R. eutropha strain H16 | Wild type | DSM 428 |
| Z. mobilis subsp. mobilis | Wild type | DSM 424 ATCC 10988 |
| Z. mobilis subsp. mobilis | Wild type | DSM3580 ATCC 29191 |
| Plasmids | | |
| pJET1.2/blunt | Ap$^r$ | Fermentas |
| pCR2.1 | Ap$^r$, Km$^r$, LacZ-α | Invitrogen |
| pJET1.2::glf | with glf as blunt end PCR product | in the examples |
| pJET1.2::mak | with mak as blunt end PCR product | in the examples |
| pJET1.2::pmi | with pmi as blunt end PCR product | in the examples |
| pCR2.1::P$_{nk}$ | with neokanamycin promoter as XhoI/NdeI fragment | in the examples |
| pCR2.1::P$_{nk}$::glk | with neokanamycin promoter and glk as XhoI/EcoRI fragment | in the examples |
| pBBR1MCS-3 | TC$^r$, LacZ-α, mob, rep | Kovach et al. 1995 |
| pBBR1MCS-2::P$_{nk}$::glf | with neokanamycin promoter and glf as XhoI/SacI fragment | in the examples |
| pBBR1MCS-2::P$_{nk}$::glk::glf | with neokanamycin promoter, glk and glf as XhoI/SacI fragment | in the examples |
| pBBR1MCS-3::glf | with glf as KpnI/PstI fragment | in the examples |
| pBBR1MCS-3::glf::mak | with glf and mak as KpnI/XbaI fragment | in the examples |
| pBBR1MCS-3::glf::pmi | with glf as KpnI/PstI fragment and pmi XbaI/SacI fragment | in the examples |
| pBBR1MCS-3::glf::mak::pmi | with glf, mak and pmi as KpnI/SacI fragment | in the examples |
| Oligonucleotides | | |
| Pglf_KpnI_f | 5'GGTACCAAGGAAGGACTGATCATG AGTTCTGAAAGTAGTCAGGGTCTA GTC3' (SEQ ID NO: 61) | |
| Pglf_PstI_r | 5'CTGCAGCTACTTCTGGGAGCGCCA CATC3' (SEQ ID NO: 62) | |
| Pmak_PstI_f | 5'CTGCAGAAGGAAGGACTGATC GTGCGTATAGGTATCGATTTAGGCG3' (SEQ ID NO: 63) | |

TABLE 1-continued

Bacterial strains, plasmids and oligonucleotides

| Strain, plasmid or primer | Relevant characteristics | Source or reference |
|---|---|---|
| Pmak_XbaI_r | 5'<u>TCTAGA</u>TTACTCTTGTGGCCATAA<br>CCACGC3'<br>(SEQ ID NO: 64) | |
| Ppmi_XbaI_f | 5'<u>TCTAGA</u>AAGGAAGGTCGACTC<br>ATGCAAAAACTCATTAACTCAGTG CAAAAC3'<br>(SEQ ID NO: 65) | |
| Ppmi_SacI_r | 5'<u>GAGCTC</u>TTACAGCTTGTTGTAAAC<br>ACGCGCTAAAC3'<br>(SEQ ID NO: 66) | |
| glf_RT_f | 5'GTTCTATCGATTGGGTTAATGCCA<br>GTGG3'<br>(SEQ ID NO: 67) | |
| glf_RT_r | 5'GGAACATCTGCGGTGCATAATACAGC3'<br>(SEQ ID NO: 68) | |
| mak_RT_f | 5'GCGAGGTTGCAGCGGGAAGTG3'<br>(SEQ ID NO: 69) | |
| mak_RT_r | 5'AATTTCACTGCCTTTCAGCGCATGTCC3'<br>(SEQ ID NO: 70) | |
| pmi_RT_f | 5'CGCTGACGCCTTTCCTTGCGAT3'<br>(SEQ ID NO: 71) | |
| pmi_RT_r | 5'GCGGTGTTTCAGCGAACAGGAACA3'<br>(SEQ ID NO: 72) | |
| pJET1.2 forward sequencing primer, 23-mer | 5'CGACTCACTATAGGGAGAGCGGC3'<br>(SEQ ID NO: 73) | Fermentas |
| pJET1.2 reverse sequencing primer, 24-mer | 5'AAGAACATCGATTTTCCATGGCAG3'<br>(SEQ ID NO: 74) | Fermentas |
| M13/pUC-forward, 17-mer | 5'GTAAAACGACGGCCAGT3'<br>(SEQ ID NO: 75) | Jena Bio-science |
| F_Pnk_XhoI | 5'<u>CTCGAG</u>CCGGAATTGCCAGCTGGGG3'<br>(SEQ ID NO: 76) | |
| R_Pnk_NdeI | 5'<u>CATATG</u>AAACGATCCTCATCCTGTCTCTTG3'<br>(SEQ ID NO: 77) | |
| F_glk_NdeI | 5'<u>CATATG</u>ACAAAGTATGCATTAGTCGGTGATGTGGG3'<br>(SEQ ID NO: 78) | |
| R_glk_SalI | 5'<u>GTCGAC</u>TTACAGAATGTGACCTAAGGTCTGGCGTAA<br>ATGTGC3'<br>(SEQ ID NO: 79) | |
| F_glf_BamHI | 5'<u>GGATCC</u>ATGAGGATCGTTTCGCATGAGTTCTGAAAG<br>TAGTCAGGGTCTAGTC3'<br>((SEQ ID NO: 80) | |
| R_glf_SacI | 5'<u>GAGCTC</u>CTACTTCTGGGAGCGCCACATCTCCTCG3'<br>(SEQ ID NO: 81) | |

TABLE 2

Growth of recombinant R. eutropha strain H16 and of the wild type (negative control) on different carbon sources. Cells were incubated on MSM agar plates containing 1% (wt/vol) of the respective carbon source for 5 days at 30° C. Visible colony growth was phenotypically examined.

| Carbon source | R. eutropha strain H16 wild type | R. eutropha harboring pBBR1MCS-3::glf::mak::pmi | R. eutropha harboring pBBR1MCS-2::$P_{nk}$::glk::glf |
|---|---|---|---|
| L-Arabinose | − | − | − |
| D-Fructose | ++ | ++ | ++ |
| D-Galactose | − | − | − |
| D-Gluconate | ++ | ++ | ++ |
| D-Glucose | − | + | ++ |
| D-Glycerol | + | + | + |
| D-Maltose | − | − | − |
| D-Mannitol | − | − | − |
| D-Mannose | − | + | − |
| N-Acetyl-D-glucosamine | ++ | ++ | ++ |
| Pyruvate | ++ | ++ | ++ |
| D-Ribose | − | − | − |
| D-Trehalose | − | − | − |
| D-Xylose | − | − | − |

Characters:
++ growth after an incubation time of 24-72 h,
+ growth after more than 72 h of incubation,
− no visible growth detectable.

Isolation, Analysis and Modification of DNA.

Plasmid DNA was prepared from crude lysates by the alkaline extraction method (Birnboim and Doly 1979). Total DNA of Z. mobilis DSM 424 or DSM3580 and of E. coli strain K-12 was prepared using the Qiagen DNeasy™ Blood & Tissue Kit (Qiagen, Hilden, Germany) according to the manufacturer's protocol. DNA was restricted with restriction endonucleases (Gibco/BRL Gaithersburg, USA) under conditions recommended by the manufacturer. All other genetic procedures and manipulations were conducted as described by Sambrook et al. (1989).

Constructions of Plasmids and its Transfer into R. eutropha Strain H16.

Figure 2:
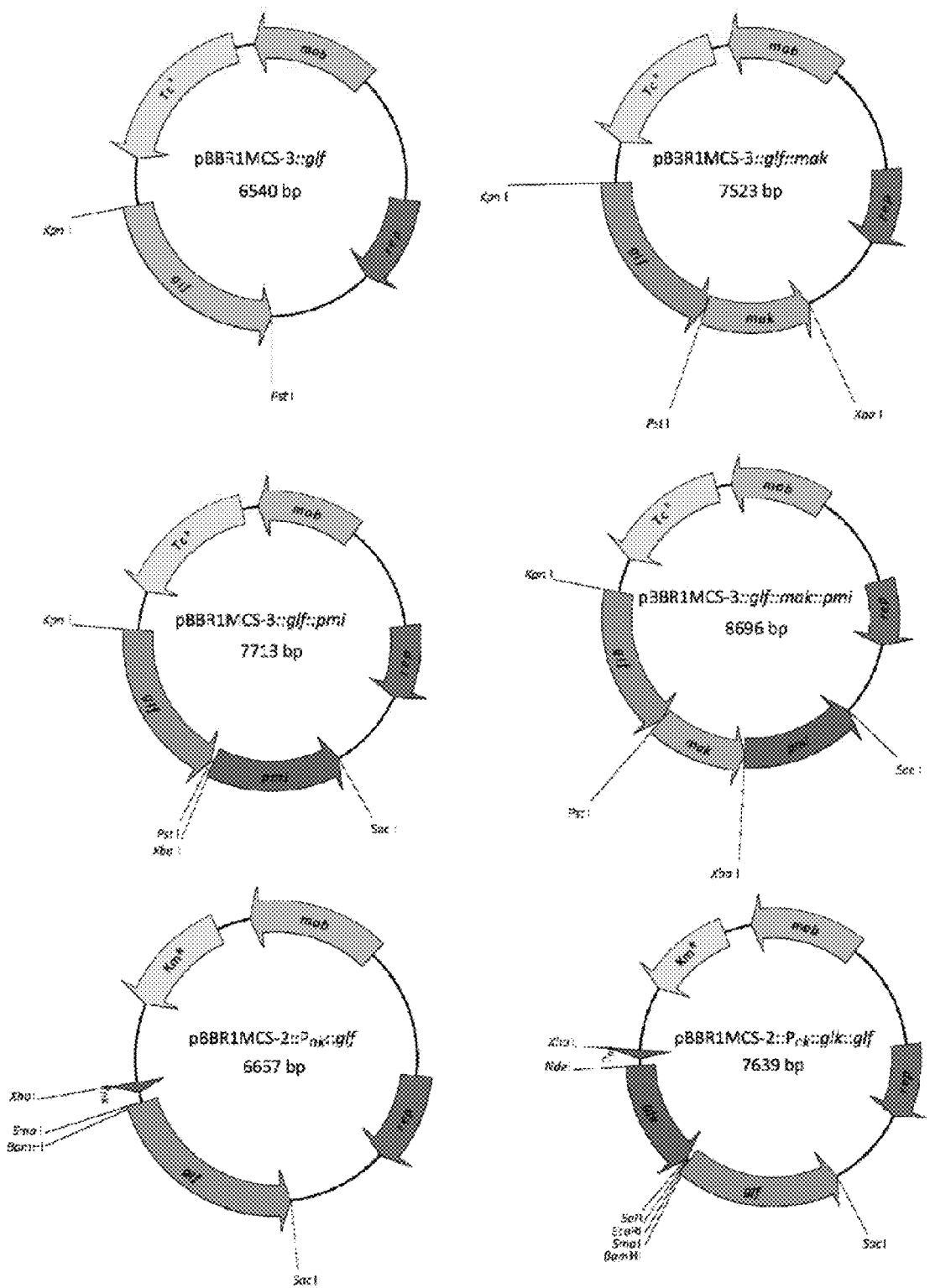
FIG. 2. Physical maps of the constructed plasmids pBBR1MCS-3::glf, pBBR1 MCS-3::glf::mak, pBBR1MCS-3::glf::pmi, pBBR1MCS-3::glf::mak::pmi, pBBR1MCS-2::$P_{nk}$::glf and pBBR1MCS-2::$P_{nk}$::glf. The genes glf, glk, mak and pmi, respectively, were excised from hybrid plasmids of pJET1.2 or pCR2.1 after subcloning using the indicated restriction sites, and were then ligated in various arrays to the linearized expression vectors pBBR1MCS-2 and pBBR1MCS-3. Relevant cleavage sites and structural genes are indicated ($Km^R$, kanamycin resistance cassette, $Tc^R$, tetracycline resistance cassette; mob, mobilization site; rep, origin of replication; glf, gene encoding the glucose-facilitated diffusion transporter (GLF) from *Z. mobilis*; glk, gene encoding the glucokinase (GLK) from *E. coli*; mak, gene encoding a mannofructokinase (MAK) from *E. coli*; pmi, gene encoding a phosphomannose isomerase (PMI) from *E. coli*).

The coding regions of glf from Z. mobilis mobilis DSM424 and DSM3580, and of glk, mak and pmi from E. coli, respectively, were amplified by PCR using oligonucleotides Pglf_KpnI_f, Pglf_PstU_r, F_glf_BamHI and R_glf_SacI for amplification of glf, F_Pnk_XhoI and R_Pnk_NdeI for $P_{nk}$, F_glk_NdeI and R_glk_SalI for glk, Pmak_PstI_f and Pmak_XbaI_r for amplification of mak, or Ppmi_XbaI_f and Ppmi_SacI_r for amplification of pmi, respectively (Table 1). For PCR, KOD Hot Start DNA Polymerase (Merck, Darmstadt, Germany) was used according to the manufacturer's instructions. PCR products were then cloned into the pJET1.2/blunt cloning vector (Fermentas, Germany) using T4 DNA ligase (Gibco BRL, Gaithersburg, USA) or into cloning vector pCR2.1 (Invitrogen, Karlsbad, Germany) and transferred into E. coli strain TOP10. Plasmids were isolated from ampicillin resistant clones, and the cloned fragments were excised by restriction with respective suitable restriction enzymes for further cloning, extracted from gel after separation using the E.Z.N.A gel extraction kit (Omega Bio-tec, Bangalore, India). For expression experiments in R. eutropha strain H16, the broad host range vectors pBBR1MCS-2 and pBBR1MCS-3 were used for cloning of glf, glk, mak and pmi. Vector pBBR1MCS-2 conferred kanamycin resistance, whereas pBBR1MCS-3 conferred tetracycline resistance for selection to E. coli and R. eutropha strain H16. The coding region of glf was excised by restriction with KpnI and PstI and ligated to KpnI/PstI linearized plasmid pBBR1MCS-3, yielding plasmids pBBR1MCS-3::glf (FIG. 2). The coding sequence of the neokanamycin-promoter $P_{nk}$ was amplified using primers F_Pnk_XhoI and R_Pnk_NdeI using isolated vector pBBR1MCS-2 and further ligated into the vector pCR2.1 (Invitrogen, Carlsbad, USA) according to the manufacturer's instructions yielding pCR2.1::$P_{nk}$. The glk-gene was amplified by tailored PCR from total DNA of E. coli/K12 using oligonucleotides F_glk_NdeI and R_glk_SalI as primers. The resulting PCR product was cloned as NdeI/SalI fragment into pCR2.1::$P_{nk}$, yielding pCR2.1::$P_{nk}$::glk. The glf gene was amplified by tailored PCR from total DNA of Z. mobilis DSM3580 using oligonucleotides F_glf_BamHI and R_glf_SacI as primers. The resulting PCR product was cloned as BamHI/SacI fragment into pBBR1MCS-2, yielding pBBR1MCS-2::glf. To obtain plasmid pBBR1MCS-2::$P_{nk}$::glk::glf, the coding region of $P_{nk}$::glk was excised by restriction with XhoI and EcoRI from plasmid pCR2.1::$P_{nk}$::glk and ligated into XhoI/EcoRI linearized pBBR1MCS-2::glf. The coding sequence of glk was further excised by restriction with NdeI/SalI from plasmid pBBR1MCS-2::$P_{nk}$::glk::glf, the linearized plasmid was blunted using T4 Polymerase (Gibco BRL, Gaithersburg, USA) and religated using T4 DNA ligase (Gibco BRL, Gaithersburg, USA) yielding plasmid pBBR1MCS-2::$P_{nk}$::glf. To obtain plasmids pBBR1MCS-3::glf::mak and pBBR1MCS-3::glf::pmi, the coding regions of mak and pmi were excised by restriction with PstI and XbaI or XbaI and SacI, respectively, and ligated to PstI/XbaI and XbaI/SacI linearized plasmid pBBR1MCS-3::glf, respectively (FIG. 2). The excised coding regions of mak and pmi were also ligated together to PstI/SacI linearized plasmid pBBR1MCS-3::glf yielding pBBR1MCS-3::glf::mak::pmi (FIG. 2). All plasmids were transferred to E. coli strain S17-1 by transformation (Hanahan 1983).

Transfer of DNA by Conjugation.

Transfer of plasmids pBBR1MCS-2, pBBR1MCS-2::$P_{nk}$::glf, pBBR1MCS-2::$P_{nk}$::glk::glf pBBR1MCS-3, pBBR1MCS-3::glf, pBBR1MCS-3::glf::mak, pBBR1MCS-3::glf::pmi and pBBR1MCS-3::glf::mak::pmi (Table 1) was performed by conjugation applying a previously described protocol (Friedrich et al. 1981), using E. coli S17-1 as donor and R. eutropha strain H16 as recipient.

DNA Sequence Analysis.

DNA was sequenced in a 48-capillary 3730 DNA Analyzer™ electrophoresis system (Applied Biosystems, Foster City, Calif.). For sequencing of inserts in the pJET1.2/blunt cloning vector (Fermentas, Germany) the pJET1.2 forward sequencing primer, 23-mer and pJET1.2 reverse sequencing primer, 24-mer were used. The universal M13/pUC-forward primer and the M13/pUC-reverse primer were used for sequencing inserts in plasmids pBBR1MCS-2 and pBBR1MCS-3 (Kovach et al. 1995).

RT-PCR Analysis of Total RNA Isolated from R. eutropha Strain H16.

DNA-free total RNA of R. eutropha strain H16 was prepared using the RNeasy™ RNA purification kit (Qiagen, Hilden, Germany) according to the manufacturer's protocol. For identification of glf-, mak- and pmi-derived mRNA, RT-PCR was applied using oligonucleotides glf_RT_f, glf_RT_r, mak_RT_f, mak_RT_r, pmi_RT_f and pmi_RT_r (Table 1). RT-PCR was carried out using a Qiagen OneStep RT-PCR kit (Qiagen, Hilden, Germany) according to the manufacturer's protocol and 0.5 ng RNA as template. To exclude any DNA contamination that could serve as template for PCR, template RNA was added in a control experiment, after inactivation of reverse transcriptase for 15 min at 95° C. in presence of Taq-polymerase. Absence of PCR products indicated that the RT-PCR products were not derived from contaminating DNA.

Preparation of Soluble Protein Fraction from *R. eutropha* Strain H16.

Cells of recombinant strains of *R. eutropha* strain H16 were cultivated as described above in presence of 1% (wt/vol) sodium gluconate as sole carbon source. Cells were harvested by centrifugation for 15 min at 4° C. and 3,500×g, washed with 100 mM MOPS buffer (pH 7.0) and resuspended in two volumes of the same buffer. Disruption was done by sonication employing a Sonifer® 250 ultrasonic homogenizer (Branson Sonic Power Company) with an amplitude of 16 μm (1 min/ml; 50% output control). During ultrasonication, samples were cooled with an ice-NaCl mixture. Soluble membrane-free protein fractions were prepared by 60 min ultracentrifugation of the crude extracts at 100,000×g and 4° C.

Solubilisation of Membrane Proteins.

Recombinant cells of *R. eutropha* H16 were cultivated as described above in presence of 1% (wt/vol) glucose as sole carbon source. After 48 h cells were harvested by 15 min centrifugation at 3,500×g and 4° C., washed once with 0.9% (wt/vol) NaCl and resuspended in one volume of 100 mM Tris/HCl buffer (pH 7.0). Cell disruption was carried out by a threefold passage through a precooled French Pressure Cell at 1,000 MPa. The obtained lysates were centrifugated as before in order to remove residual cells. The membrane fraction was prepared by 1 h centrifugation of the supernatant at 100,000×g and 4° C., resuspended in 2 mL of 20 mM Tris/HCl buffer (pH 7.4) containing 200 mM NaCl and 2% (vol/vol) Triton™ X-114 non-ionic detergent and incubated for 12 h on ice on a rotary shaker (VV3, VWR international GmbH, Darmstadt, Germany). The lysate was centrifugated for 20 min at 3,500×g and 4° C. The supernatant was incubated for 5 min at 37° C. and centrifugated for 20 min at 3.500×g and 37° C. to remove Triton™ X-114 non-ionic detergent according to Bordier (Bordier, 1981). The supernatant was further diluted with 2 volumes of the same buffer without Triton™ X-114 non-ionic detergent to decrease the detergent concentration.

One-Dimensional PAGE.

Protein samples were resuspended in gel loading buffer (0.6% (wt/vol) SOS; 1.25% (vol/vol) β-mercaptoethanol; 0.25 mM EDTA; 10% (vol/vol) glycerol; 0.001% (wt/vol) bromophenol blue; 12.5 mM Tris/HCl, pH 6.8) and were separated in 12.5% (wt/vol). SDS-polyacrylamide gels as described by Laemmli (1970). The proteins were stained with Coomassie brilliant blue R-250 (Weber and Osborn, 1969). Samples of crude extracts and solubilized membrane proteins were analyzed by this method.

MAK, PMI and GLK Activity Assays.

Soluble protein fractions of recombinant *R. eutropha* strain H16 were applied for MAK, PMI and GLK activity measurements at 30° C. using a Nicolet Evolution™ 100 UV/VIS spectrophotometer (Thermo Electron Corporation, Cambridge, UK). Activity of MAK was assayed with an NADH-coupled system as described by Sebastian and Asensio (1972) with some modifications, using pyruvate kinase and lactate dehydrogenase as auxiliary enzymes. The buffered reaction mixture (100 mM MOPS, pH 7.0) contained 2 mM $MgCl_2$, 2 mM ATP, 0.2 NADH, 5 mM mannose, 0.2 mM PEP, 5 U $ml^{-1}$ pyruvate kinase, 5 U $ml^{-1}$ lactate dehydrogenase and 5 to 100 μl of soluble extract. PMI activity was measured with an NADP-coupled assay (Kang and Markovitz 1967) with some modifications, using phosphoglucose isomerase and glucose-6-phosphate dehydrogenase as auxiliary enzymes. The buffered reaction mixture (100 mM MOPS, pH 7.0) contained 5 mM $MgCl_2$, 1 mM NADP, 3 mM mannose-6-phosphate, 1 U $ml^{-1}$ phosphoglucose: isomerase, 1 U $ml^{-1}$ glucose-6-phosphate dehydrogenase and 10 to 100 μl of soluble extract.

GLK activity was measured with an NADPH-coupled system according to the method of Gottschalk (Gottschalk et al. 1964) with modifications concerning the buffer. The buffer mixture (100 mM Tris/HCl, pH 7.6) contained 7 mM $MgCl_2$, 0.9 mM NADP, 460 mM D-glucose, 0.7 mM ATP, 0.35 U $ml^{-1}$ glucose-6-phosphate-dehydrogenase and 10 to 50 μl of enzyme preparation.

Analysis of PHB Content of Recombinant *R. eutropha* Cells by GC.

Lyophilized cell material was subjected to methanolysis in presence of methanol and sulfuric acid (85% vol/vol, MeOH and 15%, vol/vol, $H_2SO_4$) for 4 h at 100° C., and the resulting methylesters of the PHA constituents were characterized by gas chromatography using an Agilent™ 6850 GC (Agilent Technologies, Waldbronn, Germany) equipped with a BP21 capillary column (50 m by 0.22 mm; film thickness, 250 nm; SGE, Darmstadt, Germany) and a flame ionization detector (Agilent Technologies). A 2 μl portion of the organic phase was analyzed after split injection (split ratio, 1:5), and as constant hydrogen flow of 0.6 ml $min^{-1}$ was used as carrier gas. The temperatures of the injector were 250° C. and 220° C., respectively. The following temperature program was applied: 120° C. for 5 min, increase of 3° C. $min^{-1}$ to 180° C. and increase of 10° C. $min^{-1}$ to 220° C. and 220° C. for 31 min. Substances were identified by comparison of their retention times to those of standard fatty acid methyl ester.

The *Z. mobilis* glf gene plus the *E. coli* mak and pmi genes were episomally introduced and expressed in *R. eutropha* and characterized the recombinant strains. The engineered pathways of glucose and mannose catabolism in the recombinant *R. eutropha* strain are depicted in FIG. 1.

Construction of Different pBBR1 Expression Vectors for *R. eutropha* Strain H16.

The coding regions of the *Z. mobilis* glf gene (1,449 bp) and the *E. coli* genes mak (936 bp), pmi (1,203 bp) and glk (966 bp) were amplified by PCR from genomic gDNA of *Z. mobilis* DSM 424 and *E. coli* strain K-12, respectively. The four PCR products comprised beside the coding regions also suitable ribosome binding sites for *R. eutropha* upstream of the respective start codon to enable expression in this host. These fragments were cloned via the pJET1.2/blunt or pCR2.1 vector into the broad-host range vectors pBBR1MCS-2 and pBBR1MCS-3 under the control of the neokanamycin- or lac-promoter, respectively, which allow constitutive expression of the cloned genes in *R. eutropha* H16, yielding plasmids pBBR1MCS-2::$P_{nk}$::glf, pBBR1MCS-2::$P_{nk}$::glk::glf, pBBR1MCS-3::glf, pBBR1MCS-3::glf::mak, pBBR1MCS-3::glf::pmi and pBBR1MCS-3::glf::mak::pmi (FIG. 2). Accurate construction of these plasmids was confirmed by sequencing. Additionally, the functionality of the pmi gene in pBBR1MCS-3::glf::pmi and pBBR1MCS-3::glf::mak::pmi was confirmed by complementation of the pmi (manA) deficient *E. coli* mutant JE5511 (Hirota et al. 1977). The recombinant *E. coli* manA mutants exhibited good growth on solid M9 medium containing 0.5% (wt/vol) mannose as a sole carbon source after two days of incubation at 37° C. In contrast, the pBBR1MCS-3 vector did not confer growth to the manA mutant.

Transfer of Plasmids to *R. eutropha* Strain H16 and Establishment of Glucose and Mannose Utilization.

Both plasmids pBBR1MCS-2::$P_{nk}$::glf and pBBR1MCS-2::$P_{nk}$::glk::glf were transferred via conjugation from *E. coli*

S17-1 to *R. eutropha* strain H16. Transconjugants were selected on MSM agar plates containing 1% (wt/vol) sodium gluconate and kanamycin (300 µg/ml), and were from there transferred to MSM plates containing 1% (wt/vol) glucose as sole carbon source. Only recombinant strains harboring either pBBR1MCS-2::P$_{nk}$::glf or pBBR1MCS-2::P$_{nk}$::glk::glf exhibited significant growth after 5 days of incubation.

To investigate if all three genes are necessary for mannose utilization, all constructed plasmids and plasmid pBBR1MCS-3 were mobilized from *E. coli* strain S17-1 to *R. eutropha* strain H16. The transconjugants were selected on MSM agar plates containing 1% (wt/vol) sodium gluconate as a sole carbon source and tetracycline (12.5 µg/ml). They were then transferred to MSM agar plates containing mannose as a sole carbon source at various concentrations (0.2, 0.5, 1.0, 2.0, 4.0% [wt/vol]). Only recombinant strains harboring pBBR1MCS-3::glf::pmi or pBBR1MCS-3::glf::mak::pmi exhibited significant growth in presence of any tested mannose concentration. Whereas cells harboring plasmid pBBR1MCS-3::glf::mak::pmi exhibited distinct growth on mannose after 3-4 days of incubation, cells with pBBR1MCS-3::glf::pmi only showed growth after an incubation time of 5-6 days. In contrast, recombinant strains harboring plasmid pBBR1MCS-3::glf or pBBR1MCS-3::glf::mak, respectively, exhibited barely no growth even after an incubation period of 30 days. Only after prior exposure of the latter recombinant strains on MSM plates containing fructose instead of gluconate, slight growth occurred after a prolonged time of incubation.

Control of Expression of glf, glk, mak and pmi.

Figure 3:
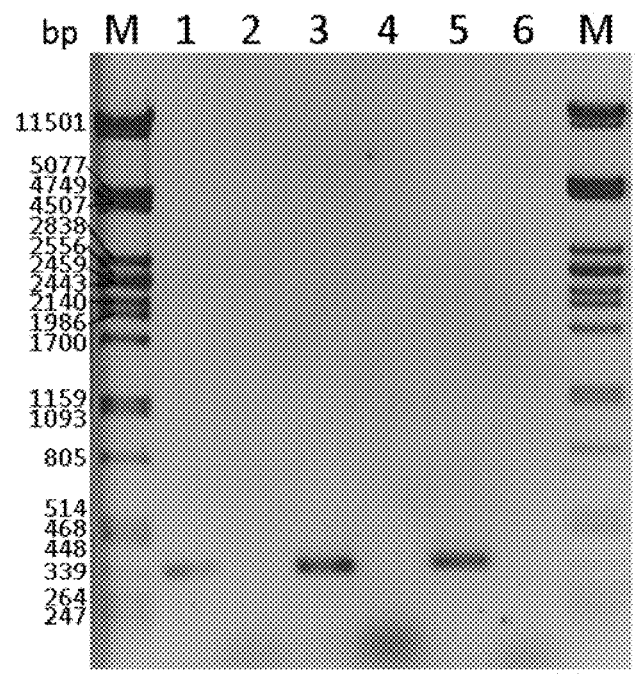
FIG. 3. Transcription analysis of glf, mak and pmi in *R. eutropha* strain H16 harboring pBBR1MCS-3::glf::mak::pmi and in the negative control harboring only the vector pBBR1MCS-3. Expression of glf, mak and pmi was analyzed by RT-PCR in samples containing total RNA isolated from cells of the exponential growth phase of *R. eutropha* strain H16 harboring pBBR1MCS-3::glf::mak::pmi and of *R. eutropha* strain H16 harboring the vector pBBR1MCS-3. Cells were grown in MSM containing 1% (wt/vol) sodium gluconate as sole carbon source. The resulting PCR products were separated by agarose gel electrophoresis and stained with ethidium bromide. Lanes 1, 3 and 5 represent the RT-PCR assay for glf, mak and pmi, respectively, for *R. eutropha* strain H16 harboring pBBR1MCS-3::glf::mak::pmi, whereas lanes 2, 4 and 6 represent the negative controls to detect whether there is any expression of glf, mak and pmi in the strain harboring only the vector pBBR1MCS-3. A λ/PstI DNA Marker (lanes M, Fermentas, Germany) served for size comparison.

To confirm the presence of glf, mak, and pmi derived mRNA, transcriptional analyses of the recombinant strains were performed. For this, cells of the recombinant strains of *R. eutropha* harboring pBBR1MCS-3::glf::mak::pmi or pBBR1MCS-3 were cultivated in MSM containing 1% (wt/vol) sodium gluconate as a sole carbon source. Since P$_{lac}$ is a constitutive promoter in *R. eutropha* strain H16 (Siedow et al. 1999), all three genes should be expressed constitutively without further induction. Transcriptional analyses were done by one-step RT-PCR. Total RNA from cells of late logarithmic growth phase served for RT-PCR using primers glf_RT_f, glf_RT_r, mak_RT_f, mak_RT_r, pmi_RT_f and pmi_RT_r specific for glf, mak and pmi (Table 1). PCR products of the expected size of 351 bp for glf, mak and pmi, respectively, were obtained if RNA isolated from recombinant pBBR1MCS-3::glf::mak::pmi harboring cells of strain 1-416 was analyzed. This clearly demonstrated that glf, mak and pmi were only transcribed in cells of the recombinant strain of *R. eutropha* strain H16 harboring pBBR1MCS-3::glf::mak::pmi but not in the negative control harboring only the vector pBBR1MCS-3. The absence of PCR products in the control without any activity of reverse transcriptase indicated that the RT-PCR product was not derived from contaminating DNA (FIG. 3).

Figure 4:
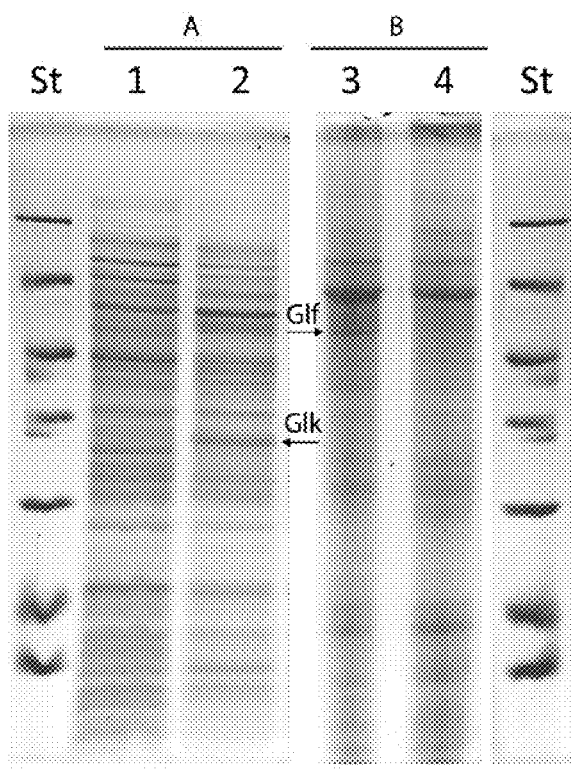
FIG. 4. Crude extracts and solubilized membrane proteins of recombinant *R. eutropha* strain H16 harboring pBBR1MCS-2 or pBBR1MCS-2::$P_{nk}$::glk::glf. Cells were grown for 48 h in MSM medium containing 1% (wt/vol) sodium glucose as carbon source. Proteins were separated in 12.5% (wt/vol) SDS-polyacrylamide gels and stained with Coomassie brilliant blue. A, crude extracts. Lane 1: *R. eutropha* strain H16 pBBR1MCS-2, lane 2: *R. eutropha* strain H16 pBBR1MCS-2::$P_{nk}$::glk::glf; B, solubilized membrane proteins. Lane 3: *R. eutropha* strain H16 pBBR1MCS-2, lane 4: *R. eutropha* strain H16 pBBR1MCS-2::$P_{nk}$::glk::glf. St, molecular weight standard. Arrows indicate detected recombinant proteins glucokinase (Glk) and glucose transporter (Glf).

To further confirm the transcription of glk and glf in recombinant strains harboring plasmid pBBR1MCS-2::P$_{nk}$::glk::glf at the protein level, an analysis by SDS-PAGE was performed. As Glf is a transmembrane protein (Parker et al. 1995), membrane proteins of both *R. eutropha* strain H16 harboring vector pBBR1MCS-2 and *R. eutropha* strain H16 harboring plasmid pBBR1MCS-2::P$_{nk}$::glk::glf were solubilized and separated by PAGE. The electropherogram showed a distinct protein band with an apparent mass of 50 kDa representing Glf, that was absent in the control. Similarly, analysis of the soluble cell fraction showed a distinct protein band at 35 kDa, representing Glk (FIG. 4).

The presence of functional active MAK, PMI and GLK in the recombinant strains was confirmed by enzymatic analyses. Coupled enzyme assays employing the soluble protein fractions obtained from cells of the recombinant strain of H16 harboring pBBR1MCS-3::glf::mak::pmi, or pBBR1MCS-2::P$_{nk}$::glk::glf cultivated in MSM containing 1% (wt/vol) sodium gluconate as sole carbon source, demonstrated the presence of active PMI (0.25 U mg$^{-1}$), MAK (0.14 U mg$^{-1}$) and also GLK (0.52 U mg$^{-1}$), respectively, whereas these activities except GLK (0.02 U mg$^{-1}$) were absent in the soluble protein fractions of the negative control of strain H16 harboring plasmids pBBR1MCS-2 or pBBR1MCS-3, respectively, thus indicating the absence of PMI and MAK in the negative control strain.

Investigations on Utilization of Several Carbon Sources by the Recombinant Strains of *R. eutropha* H16.

In comparison to the other recombinant strains, *R. eutropha* strain H16 harboring plasmids pBBR1MCS-2::P$_{nk}$::glk::glf or pBBR1MCS-3::glf::mak::pmi exhibited the fastest growth on glucose or mannose of all tested substrates, respectively, as a sole carbon source. These strains were therefore further investigated with regard to the utilization of several other carbon sources employing MSM agar plates each containing 1% (wt/vol) of L-arabinose, D-fructose, D-galactose, D-gluconate, D-glucose, glycerin, maltose, D-mannitol, D-mannose, N-acetyl-D-glucosamine, pyruvate, D-ribose, trehalose, or D-xylose as sole carbon source. The wild type of *R. eutropha* served as negative control. The results are summarized in Table 2. Both, the wild type strain and the recombinant strains, were able to grow in presence of D-fructose, D-gluconate, glycerol, N-acetylglucosamine, and pyruvate (Table 2). All other carbon sources mentioned above were not utilized for growth, except mannose by the recombinant harboring pBBR1MCS-3::glf::mak::pmi and glucose by the recombinant strains harboring pBBR1MCS-2::P$_{nk}$::glk::glf or pBBR1MCS-3::glf::mak::pmi (Table 2).

Growth of the Recombinant *R. eutropha* with Glucose as Sole Carbon Source.

Figure 5:
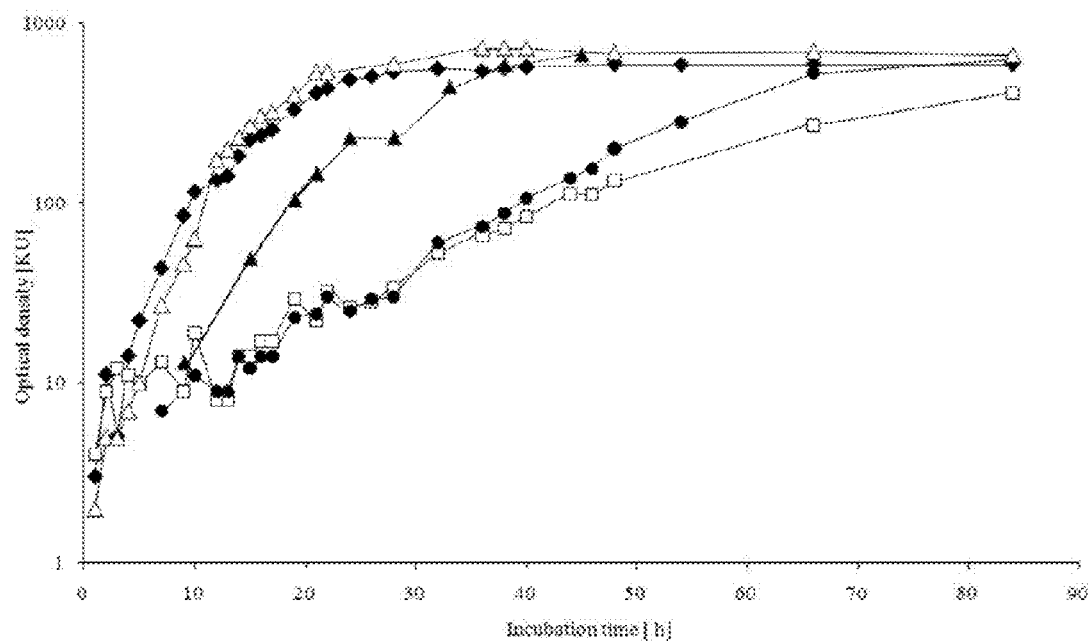
FIG. 5. Growth of recombinant *R. eutropha* strain H16. Recombinant strains of *R. eutropha* harboring different plasmids. Cells were cultivated in liquid MSM containing 1% (wt/vol) glucose as sole carbon source. □ pBBR1MCS-3::glf; ● pBBR1MCS-2::$P_{nk}$::glf; Δ pBBR1MCS-2::$P_{nk}$::glk::glf; ▲ pBBR1MCS-3::glf::mak::pmi; ◆ control *R. eutropha* H16 strain G$^{+}$1. Cultivations were done in Erlenmeyer flasks incubated on a horizontal rotary shaker at 110 rpm at 30° C. The optical density was measured at 600 nm in a Klett™ photometer.

Recombinant strains of *R. eutropha* strain H16 were cultivated in liquid MSM containing 1% (wt/vol) glucose. Although all strains exhibited growth on glucose, recombinant strain harboring pBBR1MCS-2::P$_{nk}$::glk::glf showed fastest growth ($\mu$=0.32 h$^{-1}$) in comparison to the recombinant strain harboring pBBR1MCS-3::glf::mak::pmi ($\mu$=0.12 h$^{-1}$) (FIG. 5). This was in the same order as the positive control strain G$^+$1 ($\mu$=0.30 h$^{-1}$). Interestingly, recombinant cells harboring plasmids carrying only the glf gene either under the control of the neokanamycin- or lac-promoter exhibited a strongly diminished growth ($\mu$=0.085 and 0.073, respectively) when compared to recombinant cells harboring plasmids with also the other genes (FIG. 5).

Growth of the Recombinant *R. eutropha* with Mannose or Gluconate as Sole Carbon Source.

Figure 6:
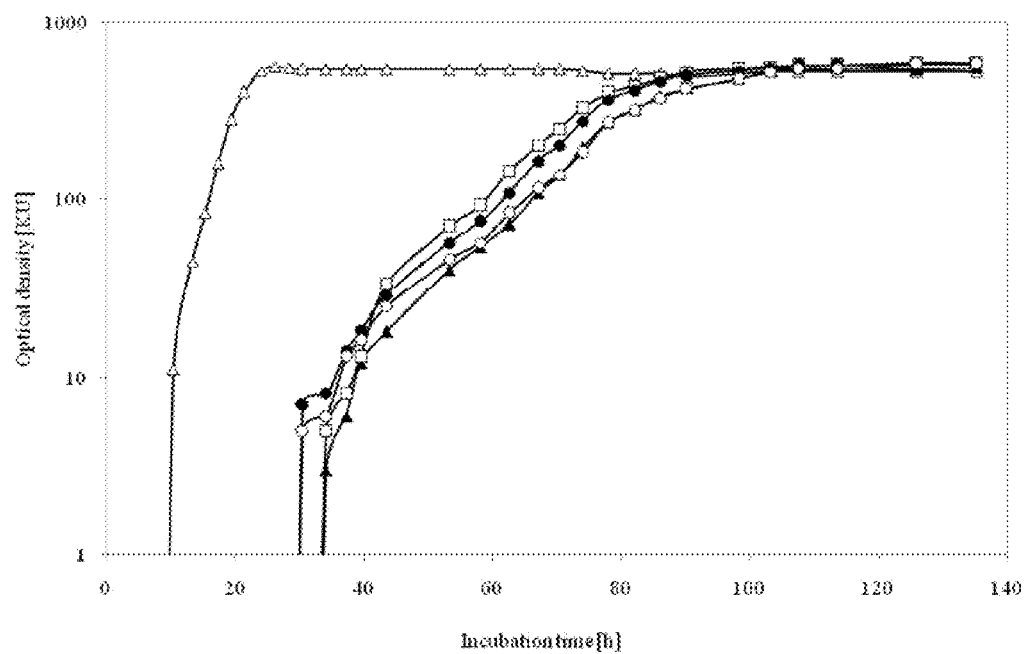
FIG. 6. Recombinant strains of *R. eutropha* harboring plasmid pBBR1MCS-3::glf::mak::pmi. Cells were cultivated in liquid MSM containing tetracycline (12.5 μg/ml) and Δ 0.5% (wt/vol) sodium gluconate, ▲ 0.5% (wt/vol) mannose, □ 1% (wt/vol) mannose, ◆ 2% (wt/vol) mannose, or ○ 4% (wt/vol) mannose as sole carbon source. Cultivations were done in Erlenmeyer flasks incubated on a horizontal rotary shaker at 130 rpm and at 30° C. The optical density was measured at 600 nm in a Klett™ photometer.

Recombinant cells of *R. eutropha* strain H16 harboring plasmid pBBR1MCS-3::glf::mak::pmi were cultivated in liquid MSM containing different concentrations of mannose as sole carbon source to evaluate optimal concentration for maximal growth. Furthermore, it was examined if the introduced genes are affecting growth of the recombinant strain in comparison to wild type strain H16 in MSM containing 0.5% (wt/vol) sodium gluconate as sole carbon source. According to our expectations, the recombinant strain H16 harboring pBBR1MCS-3::glf::mak::pmi exhibited faster growth on gluconate ($\mu$=0.33 h$^{-1}$) than on mannose ($\mu$=0.078 h$^{-1}$). Maximal growth on mannose occurred at 1% (wt/vol) mannose, whereas lower and higher concentrations of this sugar yielded slightly slower growth (FIG. 6). With gluconate as sole carbon source growth of the recombinant strain was only slightly diminished in comparison to the wild type.

Example 2

Bacterial Strains, Plasmids, Oligonucleotides and Cultivation Conditions.

All bacteria, plasmids and primers used in this study are listed in Table 3 and 4, respectively. Cells of *R. eutropha* strain H16 were cultivated in nutrient broth, or mineral salts medium (MSM) as described by Schlegel et al. (1961). Carbon sources were added to liquid MSM as indicated in the text. Liquid cultures in Erlenmeyer flasks were incubated on a horizontal rotary shaker at an agitation of 110 rpm. Solid media were prepared by addition of 1.5% (wt/vol) agar-agar.

Cells of *Escherichia coli* were cultivated at 37° C. in Lysogeny Broth (LB, [Sambrook et al. 1989]), or M9 mineral salts medium (Sambrook et al. 1989) with D-xylose as sole carbon source. Antibiotics were applied according to Sambrook et al. (1989) and as indicated in the text.

Isolation, Analysis and Modification of DNA.

Plasmid DNA was prepared from crude lysates by the alkaline extraction method (Birnboim and Doly 1979). Total DNA of *E. coli* strain K-12 was prepared using the Qiagen DNeasy™ Blood & Tissue Kit (Qiagen, Hilden, Germany) according to the manufacturer's protocol. DNA was restricted with restriction endonucleases (Gibco/BRL, Gaithersburg, USA) under conditions recommended by the manufacturer. All other genetic procedures and manipulations were conducted as described by Sambrook et al. (1989).

TABLE 3

Bacterial strains, plasmids and oligonucleotides used in this study

| Strain, plasmid or primer | Relevant characteristics | Source or reference |
|---|---|---|
| Strains | | |
| *E. coli* K-12 | Wild type | DSM 426 |
| *E. coli* TOP10 | F⁻ mcrA, Δ(mrr-hsdRMS-mcrBC) f80lacZ ΔM15, ΔlacX74, deoR, recA1, araD139, Δ(ara-leu)7697, galU, galK, rpsL, endA1, nupG | Invitrogen |
| *E. coli* S17-1 | recA1, thi1, hsdR17($r_k^-$, $m_k^+$), proA, tra-genes of RP4 plasmid chromosomally integrated (Mobilization strain) | Simon et al. 1983 |
| *E. coli* HB101 | hsdS, recA, proA, lacy, 9alK, xyl-5, mtl | *E. coli* Genetic Stock Center (Hirota et al. 1977) |
| *E. coli* JWL255 | xyl91pR | *E. coli* Genetic Stock Center (Hirota et al. 1977) |
| *E. coli* LR2-168 | thi, arg, met, his, gal, xyl-7 | *E. coli* Genetic Stock Center (Hirota et al. 1977) |
| *R. eutropha* strain H16 | Wild type | DSM 428 |
| Plasmids | | |
| pJET1.2/blunt | Ap^r | Fermentas |
| pJET1.2::xylA | with xylA as blunt end PCR product | in the examples |
| pJET1.2::xylB | with xylB as blunt end PCR product | in the examples |
| pJET1.2::xylE | with xylE as blunt end PCR product | in the examples |
| pBBR1MCS-3 | Tc^r, LacZ-α, mob, rep | Kovach et al. 1995 |
| pBBR1MCS-3::xylFGH | with xylFGH as SpeI/SacII fragment | in the examples |
| pBBR1MCS-3::xylAB | with xylAB as ApaI/SpeI fragment | in the examples |
| pBBR1MCS-3::xylABE | with xylABE as ApaI/SacII fragment | in the examples |
| pBBR1MCS-3::xylABFGH | with xylABE as ApaI/SacII fragment | in the examples |

TABLE 4

PCR and sequencing primers used in this study

| Oligonucleotides | Sequence (5'→3') | Function |
|---|---|---|
| P_xylA_ApaI_f | ATT AGG GCC CAA GGA GGT TAC AGC ATG CAA GCC TAT TTT GAC CAG (SEQ ID NO: 82) | 5'-primer for the amplification of the coding region of xylA. The primer contains the restriction site for ApaI (underlined). |
| P_xylA_SmaI_r | ATT GCC CGG GTT ATT TGT CGA ACA GAT AAT G (SEQ ID NO: 83) | 3'-primer for the amplification of the coding region of xylA. The primer contains the restriction site for SmaI (underlined). |

TABLE 4-continued

PCR and sequencing primers used in this study

| Oligonucleotides | Sequence (5'→3') | Function |
| --- | --- | --- |
| P_xylB_SmaI_f | ATT GCC CGG GAA GGA GGT TAC AGC ATG TAT ATC GGG ATA GAT CTT (SEQ ID NO: 84) | 5'-primer for the amplification of the coding region of xylB. The primer contains the restriction site for SmaI (underlined). |
| P_xylB_SpeI_r | CCC GAC TAG TTT ACG CCA TTA ATG GCA GAA G (SEQ ID NO: 85) | 3'-primer for the amplification of the coding region of xylB. The primer contains the restriction site for SpeI (underlined). |
| P_xylE_SpeI_f | CCC GAC TAG TAA GGA GGT TAC AGC ATG AAT ACC CAG TAT AAT TC (SEQ ID NO: 86) | 5'-primer for the amplification of the coing region of xylE. The primer contains the restriction site for SpeI (underlined). |
| P_xylE_SacII_r | ATT GCC GCG GTT ACA GCG TAG CAG TTT GTT G (SEQ ID NO: 87) | 3'-primer for the amplification of the coding region of xylE. The primer contains the restriction site for SacII (underlined). |
| P_xylFGH_SpeI_f | CCC GAC TAG TAA GGA GGC TAC AGC ATG AAA ATA AAG AAC ATT CTA C (SEQ ID NO: 88) | 5'-primer for the amplification of the coding region of xylFGH: The primer contains the restriction site for SpeI (underlined). |
| P-xylFGH_SacII_r | ATT GCC GCG GTC AAG AAC GGC GTT TGG TTG (SEQ ID NO: 89) | 3'-primer for the amplification of the coding region xylFGH. The primer contains the restriction site for SacII (underlined). |
| | AAAACCGCGGCGGCTCGGA AGTCG (SEQ ID NO: 90) | 5'-primer for the amplification of the promoter $P_{GAPDH}$ region: The primer contains the restriction site for SacII (underlined). |
| pJET1.2 forward | CGACTCACTATAGGGAGAG CGGC (SEQ ID NO: 91) | Fermentas (sequencing primer, 23-mer) |
| pJET1.2 reverse | AAGAACATCGATTTTCCATG GCAG (SEQ ID NO: 92) | Fermentas (sequencing primer, 24-mer) |
| M13/pUC-forward | GTAAAACGACGGCCAGT (SEQ ID NO: 93) | Jena Bioscience (17-mer) |

Constructions of Plasmids and its Transfer into *R. eutropha* Strain H16.

Figure 8:
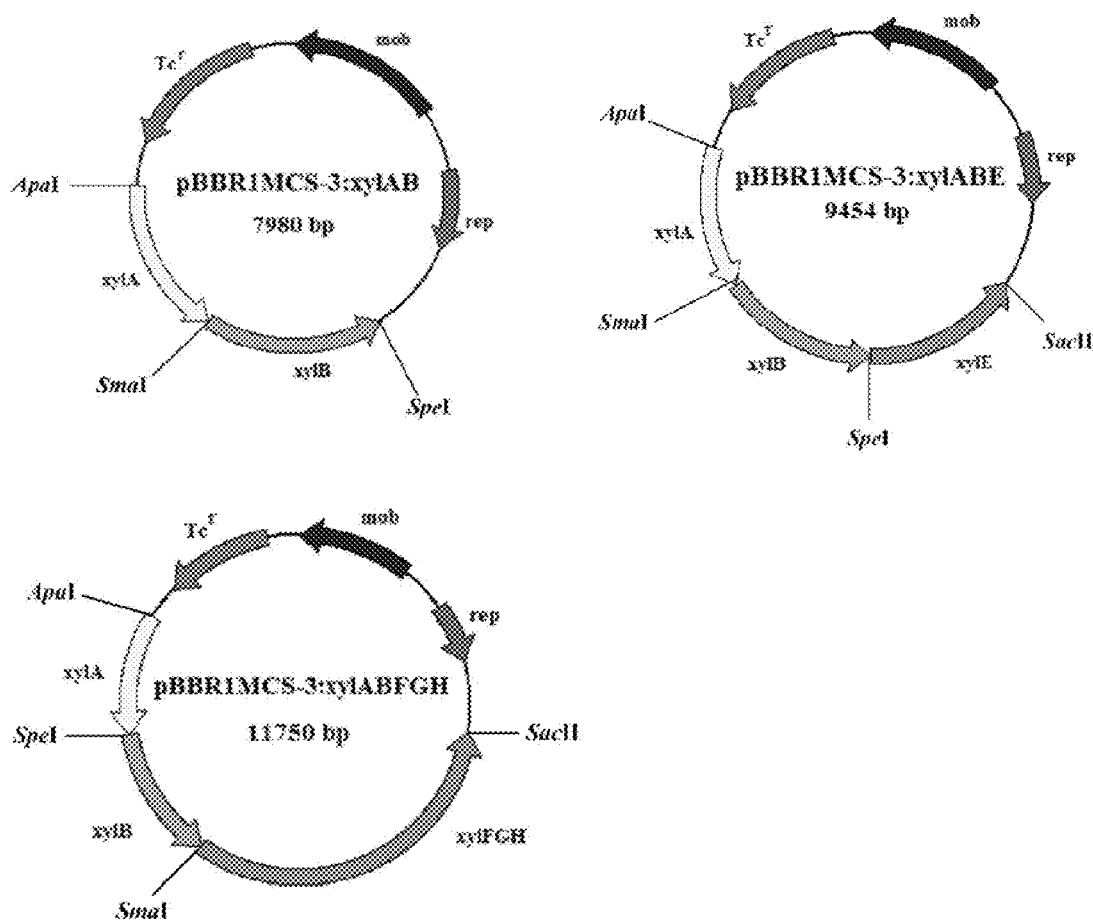
FIG. 8. Physical maps of the constructed plasmids pBBR1MCS-3::xylAB, pBBR1MCS-3::xylABE and pBBR1MCS-3::xylABFGH. The genes xylA, xylB, xylE and xylFGH, respectively, were excised from hybrid plasmids of pJET1.2 after subcloning using the indicated restriction sites, and were then ligated to the linearized expression vector pBBR1MCS-3. Relevant cleavage sites and structural genes are indicated (Tc$^R$, tetracycline resistance cassette; mob, mobilization site; rep, origin of replication; xylA, gene encoding the xylose-isomerase (XylA); xylB, gene encoding the xylulokinase (XylB); xylE, gene encoding the low affinity transporter (XylE); and xylFGH, genes encoding the ABC-transporter (XylFGH) from *E. coli*, respectively).

For amplification of the coding regions of xylA, xylB, xylE, xylFGH, talB and tktA from *E. coli* strain K12 by PCR, oligonucleotides listed in Table 4 were used. The oligonucleotides P_xylA_ApaI_f and P_xylA_SmaI_r were used for amplification of xylA, P_xylB_SmaI_f and P_xylB_SpeI_r for xylB, P_xylE_SpeI_f and P_xylE_SacII_f for xylE, and P_xylFGH_SpeI_f and P-xylFGH_SacII_r for xylFGH, respectively. Primers contained a ribosomal binding site in order to permit RNA translation in the target bacterium *R. eutropha* H16. KOD Hot Start DNA Polymerase (Merck, Darmstadt, Germany) was used for PCR amplification according to the manufacturer's instructions. PCR products were ligated to the pJET1.2/blunt cloning vector (Fermentas, Germany) using T4 DNA ligase (Gibco BRL, Gaithersburg, USA) or to plasmid pBBR1MCS-3 (Kovach et al. 1995), and transferred into *E. coli*/strain TOP10. Plasmids were isolated from ampicillin or tetracycline resistant clones, respectively, and the cloned fragments were excised by restriction with the respective suitable restriction enzymes for further cloning, extracted from gel after separation using the E.Z.N.A gel extraction kit (Omega Biotec, Bangalore, India). For expression experiments in *R. eutropha* strain H16, the broad host range vector pBBR1MCS-3 was used for cloning of xylA, xylB, xylE, and xylFGH. Vector pBBR1MCS-3 conferred tetracycline resistance for selection in *E. coli* and *R. eutropha* strain H16. The coding regions of xylA or xylB were excised by restriction with ApaI and SmaI or SmaI and SpeI, respectively, ligated to ApaI and SpeI linearized plasmid pBBR1MCS-3, yielding plasmids pBBR1MCS-3::xylAB (FIG. 8). To obtain plasmids pBBR1MCS-3::xylABE and pBBR1MCS-3::xylABFGH, the coding regions of xylE and xylFGH were excised by restriction with SpeI and SacII, respectively, and ligated to SpeI and SacII linearized plasmid pBBR1MCS-3::xylAB yielding plasmids pBBR1MCS-3:: xylABE and pBBR1MCS-3::xylABFGH, respectively (FIG. 8). All plasmids were transferred to *E. coli* strain S17-1 by transformation (Hanahan 1983).

Transfer of DNA by Conjugation.

Transfer of plasmids pBBR1MCS-3, pBBR1MCS-3::xylABE, pBBR1MCS-3::xylABFGH (Table 3) was performed by conjugation applying a previously described protocol (Friedrich et al. 1981), using *E. coli* S17-1 as donor and *R. eutropha* strain H16 as recipient.

DNA Sequence Analysis.

DNA was sequenced in a 48-capillary 3730 DNA Analyzer™ electrophoresis system (Applied Biosystems, Foster City, Calif.). For sequencing of inserts in the pJET1.2/blunt cloning vector (Fermentas, Germany) the pJET1.2 forward sequencing primer, 23-flier and the pJET1.2 reverse sequencing primer, 24-mer were used. The universal M13/pUC-forward primer and the M13/pUC-reverse primer were used for sequencing inserts in plasmid pBBR1MCS-3 (Kovach et al. 1995).

Preparation of Soluble Protein Fractions from R. eutropha Strain H16.

Cells of recombinant strains of R. eutropha strain H16 were cultivated in nutrient broth medium. Cells were harvested by centrifugation for 15 min at 4° C. and 3,500×g, washed with 50 mM Tris/HCl buffer (pH 7.5) and resuspended in two volumes of the same buffer. Disruption was done by sonication employing a Sonifer® 250 ultrasonic homogenizer (Branson Sonic Power Company) with an amplitude of 16 µm (1 min/ml; 50% output control). During ultrasonication samples were cooled with an ice-NaCl mixture. Soluble membrane-free protein fractions were prepared by 60 min ultracentrifugation of the crude extracts at 100,000×g and 4° C.

XylA and XylB Activity Assays.

Soluble protein fractions of recombinant R. eutropha strain H16 were applied for XylA and XylB activity measurements at 30° C. using a Nicolet Evolution™ 100 UV/VIS spectrophotometer (Thermo Electron Corporation, Cambridge, UK). Activity of XylA (Gao et al. 2002, Mejnen et al. 2008) or XylB (Shamanna and Sangerson 1979, Eliasson et al. 2000) was assayed with an NADH-coupled system with some modifications, using sorbitol dehydrogenase or pyruvate kinase and lactate dehydrogenase, respectively, as auxiliary enzymes. The buffered reaction mixture (50 mM Tris/HCl, pH 7.5) for XylA activity measurement contained 10 mM $MgSO_4$, 1 mM triethanolamine, 0.2 mM NADH, 50 mM D-xylose, 0.5 U ml$^{-1}$ sorbitol dehydrogenase, and 5 to 100 µl of soluble extract. The buffered reaction mixture (50 mM Tris/HCl, pH 7.5) for XylB activity measurement contained 2 mM $MgCl_2$, 2 mM ATP, 0.2 mM NADH, 10 mM xylulose, 0.2 mM PEP, 10 µml$^{-1}$ pyruvate kinase, 10 U ml$^{-1}$ lactate dehydrogenase and 5 to 100 µl of soluble extract.

D-xylose Utilization in R. eutropha.

Figure 7:
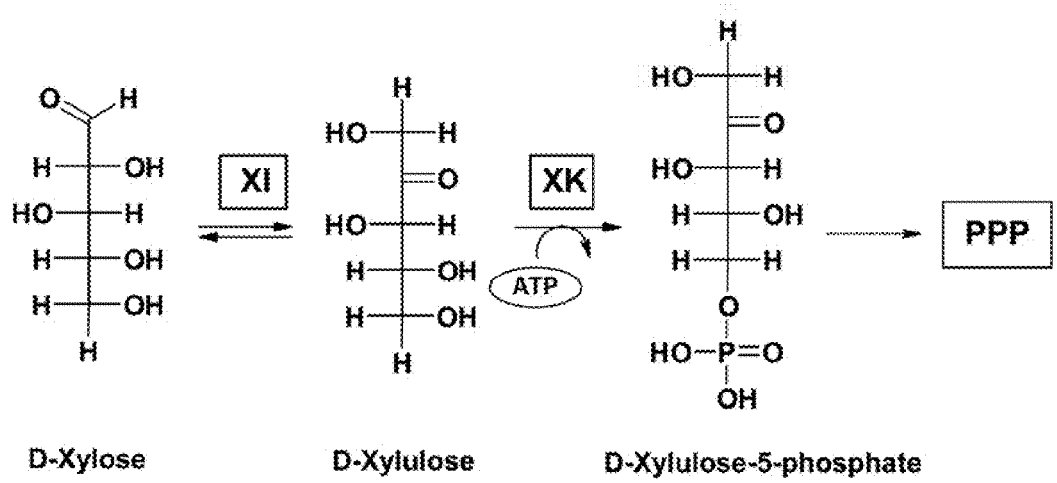
FIG. 7. The utilization pathway of D-xylose in bacteria (XI, xylose isomerase; XK, xylulokinase; PPP, pentose phosphate pathway)

After D-xylose is taken up by the cell, the xylA gene encoding the enzyme D-xylose isomerase (XylI or XylA; EC 5.3.1.5) catalyzes the reversible conversion of the aldose D-xylose into its keto-form D-xylulose. Subsequently, the D-xylulose is phosphorylated to D-xylulose-5-phosphate, utilizing ATP as energy and phosphate source. This step is catalyzed by a xylulose kinase (XylK or XylB; EC 2.7.1.17). D-Xylulose-5-phosphate can be utilized further as an intermediate of the non-oxidative pentose phosphate pathway. As E. coli strain K12 is one of the most extensively studied organisms utilizing D-xylose, the genes xylA, encoding xylose-isomerase, xylB encoding xylulokinase, xylE encoding the low affinity transporter and xylFGH encoding the ABC-transporter were amplified using genomic DNA of E. coli K12, episomally introduced and expressed in R. eutropha H16. The engineered pathway of xylose catabolism in the recombinant R. eutropha strain is depicted in FIG. 7.

Construction of Different pBBR1 Expression Vectors for R. eutropha Strain H16.

The coding regions of the genes xylA (1,323 bp), xylB (1,455 bp), xylE (1,476 bp) and xylFGH (3,771 bp) were amplified by PCR from genomic gDNA of E. coli strain K12. The three PCR products comprised beside the coding regions also suitable ribosome binding sites for R. eutropha upstream of the respective start codon to enable expression in this host. These fragments were cloned via the pJET1.2/blunt vector into the broad-host range vector pBBR1MCS-3 under the control of the lac-promoter, which allows constitutive expression of the cloned genes in R. eutropha H16 (Siedow et al. 1999), yielding plasmids pBBR1MCS-3::xylAB, pBBR1MCS-3::xylABE and pBBR1MCS-3::xylABFGH (FIG. 8). Accurate construction of these plasmids was confirmed by sequencing. Additionally, the functionality of the xylA or xylB genes in pBBR1MCS-3::xylAB, pBBR1MCS-3::xylABE and pBBR1MCS-3::xylABFGH was confirmed by complementation of the xylA deficient E. coli mutant HB101, xylB deficient E. coli mutant JWL255, or xylAB deficient E. coli mutant LR2-168, respectively (Hirota et al. 1977). The recombinant E. coli mutants HB101, JWL255 or LR2-168 harboring pBBR1MCS-3::xylAB, pBBR1MCS-3::xylABE or pBBR1MCS-3::xylABFGH, respectively, exhibited good growth on solid M9 medium containing 0.5% (wt/vol) xylose as a sole carbon source after two days of incubation at 37° C. In contrast, vector pBBR1MCS-3 did not confer growth to the mutants HB101, JWL255 or LR2-168, respectively.

Transfer of Plasmids to R. eutropha Strain H16 and Establishment of D-Xylose Utilization.

Plasmids pBBR1MCS-3::xylAB, pBBR1MCS-3::xylABE and pBBR1MCS-3::xylABFGH were transferred via conjugation from E. coli S17-1 to R. eutropha strain H16. Transconjugants were selected on MSM agar plates containing 1% (wt/vol) sodium gluconate and tetracycline (12.5 µg/ml), and were subsequently transferred to MSM plates containing 1% (wt/vol) D-xylose as sole carbon source. Recombinant strains harboring plasmid pBBR1MCS-3::xylABFGH exhibited weak growth after 5 days of incubation.

Evolutionary Optimization of the Plasmid pBBR1MCS-3::xylABFGH-Harboring Strain of R. eutropha H16.

Although the recombinant plasmid pBBR1MCS-3::xylABFGH-harboring strain of R. eutropha H16 was engineered for D-xylose utilization, this strain exhibited only weak growth after 5 days of incubation. A single colony of this recombinant strain was cultivated in fluid MSM containing 1% (wt/vol) D-xylose as a sole carbon source for 2 days at 30° C. Dilutions were transferred on solid MSM containing 1% (wt/vol) D-xylose as a sole carbon source and incubated at 30° C. A single colony which showed fastest growth was again cultivated in fluid MSM containing 1% (wt/vol) D-xylose as a sole carbon source, and a dilution was again transferred on solid MSM containing 1% (wt/vol) D-xylose as a sole carbon source. After repetition of this procedure for several times, a recombinant plasmid pBBR1MCS-3::xylABFGH-harboring strain of R. eutropha H16 was obtained exhibiting comparably good growth on solid MSM containing 1% (wt/vol) D-xylose as a sole carbon source after 2 days of incubation.

Investigations on Utilization of Several Carbon Sources by the Recombinant Plasmid pBBR1MCS-3::xylABFGH-Harboring Strain of R. eutropha H16 and of the Respective Optimized Strain.

Cells of the recombinant strain of H16 harboring pBBR1MCS-3::xylABFGH and of the respective optimized recombinant strain of H16, of R. eutropha strain G+1, a glucose-utilizing mutant of R. eutropha strain H16 (Schlegel and Gottschalk 1965), and of R. eutropha strain H16 were cultivated on solid MSM agar plates containing different carbon sources (1% [wt/vol] L-arabinose, D-fructose, D-galactose, D-gluconate, D-glucose, D-maltose, D-mannose, N-acetylglucosamine, D-ribose, D-trehalose, D-xylose) to compare the growth of the strains on several carbon sources. The wild type of R. eutropha H16 served as negative control. All the strains were able to use D-fructose, D-gluconate, and N-acetylglucosamine as sole carbon sources. The plasmid pBBR1MCS-3::xylABFGH containing strain of R. eutropha strain H16 was also able to use glucose as sole carbon source showing a similar growth as R. eutropha H16 strain G+1. The plasmid pBBR1MCS-3::xylABFGH containing strain was also able to use D-xylose, L-arabinose and D-galactose as sole carbon sources.

Growth of the Recombinant Plasmid pBBR1MCS-3::xylABFGH-Harboring Strain of *R. eutropha* H16 with Glucose, Gluconate or Xylose as Sole Carbon Source.

Figure 9:
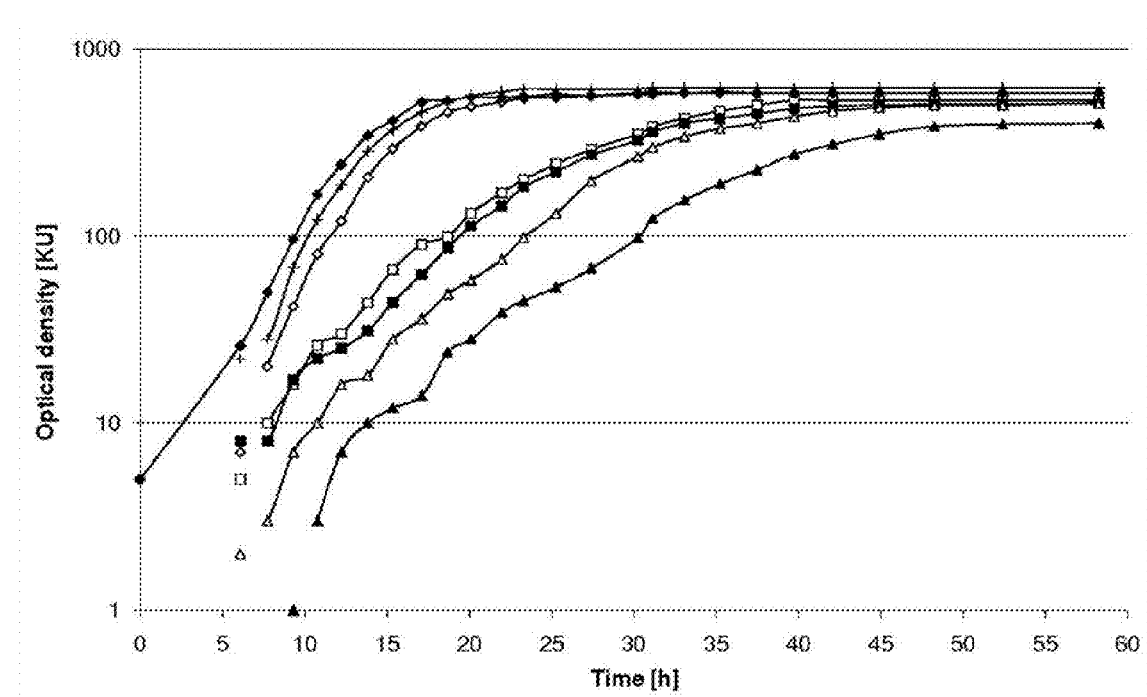
FIG. 9. Growth of the recombinant plasmid pBBR1MCS-3::xylABFGH harboring strain of *R. eutropha* strain H16, and of *R. eutropha* strain H16, which were cultivated in fluid MSM containing different concentrations (0.5%, 1%, 2% [wt/vol]) of D-xylose, 1% (wt/vol) glucose and with 1% (wt/vol) Na-gluconate as sole carbon source, respectively. □ pBBR1MCS-3::xylABFGH, 0.5% (wt/vol) D-xylose; ■ pBBR1MCS-3::xylABFGH, 1.0% (wt/vol) D-xylose; Δ pBBR1MCS-3::xylABFGH, 2.0% (wt/vol) D-xylose; ▲ pBBR1MCS-3::xylABFGH, 4.0% (wt/vol) D-xylose; ◇ pBBR1MCS-3::xylABFGH, 1.0% (wt/vol) Na-gluconate; ◆ pBBR1MCS-3::xylABFGH, 1.0% (wt/vol) glucose; + control *R. eutropha* H16, 1.0% (wt/vol) Na-gluconate. Cultivations were done in Erlenmeyer flasks incubated on a horizontal rotary shaker at 110 rpm at 30° C. The optical density was measured at 600 nm in a Klett™ photometer.

Cells of the recombinant plasmid pBBR1MCS-3::xylABFGH-harboring strain of *R. eutropha* H16 were cultivated in fluid MSM containing different concentrations (0.5%, 1%, 2%, and 4% [wt/vol]) of D-xylose, 1% (wt/vol) D-glucose and 1% (wt/vol) Na-gluconate as sole carbon source. Also *R. eutropha* strain H16 wild type was cultivated with 1% (wt/vol) Na-gluconate as sole carbon source to compare the growth rate. The recombinant strain showed a similar growth on 1% (wt/vol) Na-gluconate ($\mu=0.47$ h$^{-1}$) and also on 1% (wt/vol) glucose ($\mu=0.55$ h$^{-1}$) as sole carbon source in comparison to the wild type strain on 1% (wt/vol) Na-gluconate ($\mu=0.47$ h$^{-1}$) (FIG. 9). After almost 22 h, the stationary growth phase was reached. Growth of the recombinant strain on D-xylose as sole carbon source was slower. After almost 40 h, the stationary growth phase was reached for the cultures containing 0.5% (wt/vol) ($\mu=0.20$ h$^{-1}$) to 2% (wt/vol) ($\mu=0.18$ h$^{-1}$) of D-xylose as sole carbon source. The culture containing 4% (wt/vol) of D-xylose as sole carbon source reached the stationary growth phase after almost 50 h ($\mu=017$ h$^{-1}$) (FIG. 9).

Control of Expression of xylA and xylB in the Recombinant Plasmid pBBR1MCS-3::xylABFGH-Containing Strain of *R. eutropha* H16.

The presence of functional active XylA and XylB in the recombinant strain was confirmed by enzymatic analyses. Coupled enzyme assays employing the soluble protein fractions obtained from cells of the recombinant strain of H16 harboring pBBR1MCS-3::xylABFGH cultivated in MSM containing 1% (wt/vol) xylose as sole carbon source demonstrated the presence of active XylA (0.035 U mg$^{-1}$) and XylB (0.364 U mg$^{-1}$), respectively, whereas these activities were absent in the soluble protein fractions of the negative control of strain H16 harboring plasmid pBBR1MCS-3, thus indicating the absence of XylA and XylB in the negative control strain.

Analysis of PUB Content of Recombinant *R. eutropba* Cells by GC.

Lyophilized cell material was subjected to methanolysis in presence of methanol and sulfuric acid (85%, vol/vol, MeOH and 15%, vol/vol, H$_2$SO$_4$) for 4 h at 100° C., and the resulting methylesters of the PHA constituents were characterized by gas chromatography using an Agilent™ 6850 GC (Agilent Technologies, Waldbronn, Germany) equipped with a BP21 capillary column (50 m by 0.22 mm; film thickness, 250 nm; SGE, Darmstadt, Germany) and a flame ionization detector (Agilent Technologies). A 2 µl portion of the organic phase was analyzed after split injection (split ratio, 1:5), and a constant hydrogen flow of 0.6 ml min$^{-1}$ was used as carrier gas. The temperatures of the injector were 250° C. and 220° C., respectively. The following temperature program was applied: 120° C. for 5 min, increase of 3° C. min$^{-1}$ to 180° C. and increase of 10° C. min$^{-1}$ to 220° C. and 220° C. for 31 min. Substances were identified by comparison of their retention times to those of standard fatty acid methyl ester.

Construction of Different Vectors Suitable for Expression of Transketolase (Tkt) and Transaldolase (TalB) in Strains of the Genera *Ralstonia* and *Cupriavidus*.

The coding regions of genes encoding a transketolase (Tkt) and transaldolase (TalB) homologous protein were amplified by PCR from genomic gDNA of the respective host strain. The PCR products can comprise beside the coding regions also suitable restriction sites for cloning, suitable regulatory elements as e.g. a promoter sequence, and ribosome binding sites for strains of the genera *Ralstonia* and *Cupriavidus* upstream of the respective start codon to enable expression in this host. These features can either be provided by synthetic oligonucleotides or by fusion PCR. These fragments can be cloned via cloning vectors into vectors suitable for expression in strains of the genera *Ralstonia* and *Cupriavidus* under the control of a suitable promoter, which allows expression of the cloned genes in the respective host strain. The coding regions of genes encoding a transketolase (Tkt) and transaldolase (TalB) homologous protein can either be cloned separately or in combination with different genes, e.g. xylA, xylB, xylB, and xylFGH. Accurate construction of these plasmids can be confirmed by sequencing. The constructed plasmids can be either transferred via conjugation from *E. coli* S17-1 or by electroporation to strains of the genera *Ralstonia* and *Cupriavidus*. Transconjugants or transformants, respectively, can be selected on MSM agar plates containing 1% (wt/vol) sodium gluconate and a suitable selection for plasmid stability. Recombinant strains of the genera *Ralstonia* and *Cupriavidus* can be characterized concerning their growth on different carbon sources.

Example 3

Bacterial Strains, Plasmids, Oligonucleotides and Cultivation Conditions

All bacteria, plasmids and primers used in this application are listed in Table 5. Cells of *E. coli* were cultivated in Lysogeny Broth (LB) (Sambrook et al., 1989) or in mineral salts medium (MSM) supplemented with 1% (w/v) glucose according to Schlegel et al. (1961). Cells of *R. eutropha* were cultivated in Nutrient Broth (NB) (Sambrook at al., 1989) or in MSM supplemented with 1% (w/v) sodium gluconate and sodium oleate (0.4%, w/v) for FAEE synthesis. Liquid cultures in baffled Erlenmeyer flasks were incubated on a horizontal rotary shaker at an agitation of 110 rpm at 37° C. (*E. coli*) or 30° C. (*R. eutropha* strains). Antibiotics were applied according to Sambrook et al. (1989) and as indicated in the text.

TABLE 5

Bacterial strains, plasmids and oligonucleotides

| Strain, plasmid or primer | Relevant characteristics | Source or reference |
|---|---|---|
| Strains | | |
| *E. coli* TOP10 | F-mcrA, Δ(mrr-hsdRMS-mcrBC) f80lacZ ΔM15, ΔlacX74, deoR, recA1, araD139, Δ(ara-leu)7697, galU, galK, rpsL, endA1, nupG | Invitrogen |

TABLE 5-continued

Bacterial strains, plasmids and oligonucleotides

| Strain, plasmid or primer | Relevant characteristics | Source or reference |
|---|---|---|
| E. coli S17-1 | recA1, thi1, hsdR17(rk-, mk+), proA, tra-genes of RP4 plasmid chromosomally integrated (mobilization strain) | Simon et al. 1983 |
| R. eutropha ΔphaC1 | PHB-negative mutant of R. eutropha H16 | Peplinski et al., 2010 |
| Plasmids | | |
| pBBR1MCS-3 | $Tc^R$, lacZα, mob, rep | Kovach et al., 1995 |
| pMicrodiesel | $Amp^R$, atfA, adhB, pdc | Kalscheuer et al., 2006 |
| pBBR1MCS-3::atfA/pdc/adhB | with atfA/pdc/adhB as XbaI/ApaI fragment | in this example |
| Oligonucleotides | | |
| M13 fwd | 5' GTAAAACGACGGCCAGT 3' (SEQ ID NO: 94) | |
| M13 rev | 5' AACAGCTATGACCATG 3' (SEQ ID NO: 95) | |

Isolation, Analysis and Modification of DNA.

Plasmid DNA from R. eutropha strains was prepared from crude lysates by the alkaline extraction method (Birnboim and Doly, 1979). Plasmid DNA from E. coli was prepared with a commercial plasmid preparation kit (Roti Prep Plasmid Kit, Roth, Karlsruhe) applying the conditions recommended by the manufacturer. DNA was restricted with restriction endonucleases (Fermentas GmbH, St. Leon-Rot) under conditions recommended by the manufacturer. All other genetic procedures and manipulations were conducted as described by Sambrook et al. (1989).

Transfer of DNA by Conjugation.

Transfer of plasmids pBBR1MCS-3 and pBBR1MCS-3::atfA/pdc/adhB was performed by conjugation applying the protocol described by Friedrich et al. (1981). E. coli S17-1 was used as donor strain and R. eutropha strains ΔphaC1 as the recipient.

Preparation of Soluble Protein Fractions from R. eutropha Strains and E. coli.

Cells of recombinant strains of R. eutropha or E. coli were cultivated as described above in presence of 1% (w/v) sodium gluconate or 1% (w/v) glucose, respectively. Cells were harvested by 15 min of centrifugation at 4° C. and 3500×g, washed in a suitable buffer as described below and resuspended in two volumes of the same buffer. The cells were disrupted by sonication employing a MS72 probe and a Sonopuls™ GM200 sonicator (Bandelin, Berlin) with an amplitude of 10 μm (2 min/ml; 50% output control). During ultrasonication the samples were cooled with ice. Protein concentrations in cell crude extracts were determined as described by Bradford (1976).

DNA Sequence Analysis.

DNA was sequenced in a 48-capillary 3730 DNA Analyzer™ electrophoresis system (Applied Biosystems, Foster City, Calif.). For sequencing of inserts in PBBR1MCS-3 (Kovach et al. 1995) the universal "M13 rev"- and "M13 fwd" primers were used.

Construction of the Used Plasmids.

As the expression vector in R. eutropha H16 the vector pBBR1MCS-3 was chosen allowing a stable expression of the containing genes in R. eutropha. The necessary genes for FAEE synthesis were cut from the plasmid pMicrodiesel (Kalscheuer et al., 2006) by restriction with XbaI and ApaI resulting in a 4.8 kbp fragment containing genes atfA, pdc and adhB. This fragment was ligated to the XbaI and ApaI restricted plasmid pBBR1MCS-3 using T4 DNA ligase (Fermentas GmbH, St. Leon-Rot) resulting in the 9.9 kbp plasmid pBBR1MCS-3::atfA/pdc/adhB. The constructed plasmid was transferred by transformation (Hanahan 1983) to E. coli Top10 for verification and finally to E. coli strain S17-1 serving as the donor for conjugation experiments.

WS/DGAT, PDC and ADHB Activity Assays.

Soluble protein fractions of recombinant R. eutropha strains were applied for WS/DGAT, PDC and ADHB activity measurements at 30° C. using a Nicolet Evolution™ 100 UV/VIS spectrophotometer (Thermo Electron Corporation, Cambridge, UK). Activity of PDC was assayed with an NADH-coupled system using ADH as an auxiliary enzyme measuring $NAD^+$ production by the decrease of absorption at 340 nm. The buffered reaction mixture (50 mM potassium phosphate (KP) buffer, pH 6.5) contained 5 mM $MgSO_4$, 0.1 mM thiamine pyrophosphate (TPP), 0.175 mM NADH, 17.5 mM pyruvate, 0.1 U/ml ADH and 100 μg/ml protein solution of the soluble extract.

ADH activity was measured directly by the decrease of NADH due to the reduction of acetic aldehyde. The same reaction mixture as for the PDC activity assay was used, though pyruvate was replaced by 0.1 mM acetic aldehyde and ADH was replaced by KP buffer.

WS/DGAT activity was measured radiometrically by the synthesis of labelled wax esters from hexadecanol or ethanol and 1-$^{14}$C-palmitoyl coenzyme A. The buffered reaction mixture (125 mM sodium phosphate buffer, pH 7.4) contained 3.75 mM hexadecanol or ethanol, 12.5 μg/ml bovine serum albumine (BSA), 4.72 μM 1-$^{14}$C-palmitoyl and 200 μg/ml protein crude extract. Prior to use a double concentrated emulsion of hexadecanol, BSA and sodium-phosphate buffer was prepared by ultrasonication (1 min/ml). The reaction mixture was incubated for 30 min at 35° C. and the reaction was stopped by the addition of one volume of chloroform-methanol (1:1; v/v). After vigorous vortexing for 1 min phases were separated by centrifugation for 2 min at 16000× g. The organic phase was removed and applied to a thin layer chromatography (TLC-) plate (Silica gel 60, 20×20 cm aluminium sheets, Merck KGaA, Darmstadt) which was then developed with hexane:diethyl ether:acetic acid (90:7.5:1; (v/v/v) as the solvent. Radioactively marked wax ester spots were visualized by a PharosFX™ Phospho-Imager (Bio-Rad Laboratories GmbH, Munich) after exposing the developed TLC plate to a phosphor screen. As standard substances for TLC oleyloleate or ethyloleate were used which were visualized by iodine vapour staining.

Quantitative and Qualitative Determination of Synthesized Ethanol and FAEE.

Ethanol amounts in cell free culture media were determined by high performance liquid chromatography (HPLC). HPLC analysis of 20 µl samples was carried out with a LaChrom Elite® HPLC (VWR-Hitachi International GmbH, Darmstadt) equipped with a Metacarb 67H™ advanced C-column (length: 300 mm; inner diameter 6.5 mm; Varian, Palo Alto, USA) and a Type 2490™ refractive index (RI) detector (VWR-Hitachi International GmbH, Darmstadt).

FAEE in lyophilised cells were analysed by TLC, gas chromatography (GC) and coupled gas chromatography mass spectrometry (GC/MS). For qualitative TLC analysis 100 mg cell dry matter were mixed with 1 ml chloroform:methanol (2:1; v/v) and broken up with a type MM301 bead mill (Retsch, Haan). After centrifugation for 10 min at 16000×g the organic supernatant was separated by TLC as described for the WS/DGAT activity assays. Ethyloleate served as the standard substance. Spots were visualized by iodine vapour staining and spots of interest were scraped of the TLC plate, eluted with chloroform:methanol (2:1, v/v) and analyzed by CC or GC/MS. GC analyses of 10-100 mg cell extracts were performed with an Agilent™ 6850 capillary gas chromatograph (Agilent Technologies GmbH, Waldbronn) equipped with a BP21 capillary column (length: 50 m, inner diameter: 0.22 mm; film thickness 250 nm; SCE GmbH, Darmstadt) and a flame ionisation detector (FID). At a split ratio of 1:15 2 µl of sample were injected by an Agilent 6850 Series Auto Sampler (Agilent Technologies GmbH, Waldbronn). As the carrier gas $H_2$ (99.999%) was used at as flow rate of 0.6 ml/min. Inlet and detector temperatures were 250° C. and 275° C., respectively, the column temperature was kept at 120° C. for 5 min, followed by an increase of 3° C./min to 180° C., a second increase of 10° C./min to 220° C. and was finally kept at 220° C. for 31 min.

GC/MS analyses were carried out on a Series 6890™ GC System (Hewlett Packard, Waldbronn) equipped with a BPX35™ capillary column (length: 50 m; inner diameter: 0.25 mm; film thickness 250 nm; SGE GmbH, Darmstadt). GC was coupled with a Series 5973™ electron ionisation mass selective detector (EI-MSD) (Hewlett Packard, Waldbronn) Helium (99999%) served as the carrier gas with a constant flow rate or 0.6 ml/min. 3 µl of sample were injected by a Series 7683™ autoinjector (Hewlett Packard, Waldbronn) with a split ratio of 1:20. The inlet temperature was 250° C., that of the outlet was 240° C. The following temperature programme was applied: 5 min at 120° C., increase of 3° C./min to 180° C., followed by an increase of 5° C./min to 210° C. and finally the temperature was kept for 29 min at 210° C. Data were analysed with the NIST mass spectral search programme (Stein et al., 1998).

Transfer of Plasmids to R. eutropha ΔphaC1 and Determination of Enzyme Activities.

Both plasmids, pBBR1MCS-3 as the control vector and pBBR1MCS-3::atfA/pdc/adhB, were transferred via conjugation from E. coli S17-1 to R. eutropha ΔphaC1 resulting in the strains R. eutropha ΔphaC1 pBBR1MCS-3 and R. eutropha ΔphaC1 pBBR1MCS-3::atfA/pdc/adhB. Transconjugants could be selected on MSM agar plates containing 1% (wt/vol) sodium gluconate and tetracyclin (12.5 µg/ml) after 12 h of incubation at 30° C.

Confirmation of the Presence of Functional Active WS/DGAT, PDC and ADHB.

The presence of functional active WS/DGAT, PDC and ADHB in the recombinant strains was confirmed by enzymatic analyses.

Direct or coupled photometrical enzyme assays employing the soluble protein fractions obtained from cells of the recombinant strains of R. eutropha ΔphaC1 pBBR1MCS-3 and R. eutropha ΔphaC1 pBBR1MCS-3::atfA/pdc/adhB cultivated for 12 h at 30° C. in MSM containing 1% (wt/vol) sodium gluconate as sole carbon source, demonstrated the presence of active PDC (18.73 U/mg) and ADH B (1.51 U/mg) in R. eutropha ΔphaC1 pBBR1MCS-3::atfA/pdc/adhB, in contrast to the control strain R. eutropha ΔphaC1 pBBR1MCS-3 (PDC: 3.52 U/mg and ADH B: 0.25 U/mg). The radiometrical enzyme assays for WS/DGAT revealed the synthesis of radiolabelled wax esters and ethyl esters from hexadecanol or ethanol, respectively, and 1-$^{14}$C-palmitoyl CoA in the soluble protein fractions of R. eutropha ΔphaC1 pBBR1MCS-3:: atfA/pdc/adhB but not of R. eutropha ΔphaC1 pBBR1MCS-3, thus indicating the absence of WS/DGAT in the negative control strain. For WS/DGAT activity no specific activities were determined.

Analysis of Ethanol and FAEE Biosynthesis by HPLC, GC, GC/MS and TLC.

Ethanol and FAEE biosynthesis was analysed in the strains R. eutropha ΔphaC1 pBBR1MCS-3 and R. eutropha ΔphaC1 pBBR1MCS-3::atfA/pdc/adhB. The cells were grown in MSM-precultures containing 2% gluconate (w/v) and tetracycline or NB-medium with tetracycline for 12 h at 30° C. and were used to inoculate main cultures of the same media in baffeled 1 l Erlenmeyer flasks with 2.5% of the culture volume of 200 ml. One additional MSM culture (400 ml) additionally contained 0.4% (w/v) Na-oleate. Every 4-8 h samples were withdrawn and centrifuged. The supernatant was used for ethanol determination by HPLC. The cell pellets were washed twice with sterile saline, lyophilized and used for ethylester determination by GC, GC/MS and TLC.

Without Na-oleate as the cosubstrate maximum ethanol amounts of 1.51 g/l were found after 22 h in R. eutropha ΔphaC1 pBBR1MCS-3::atfA/pdc/adhB grown in NB, while the control strain reached 1.16 g/l after 14 h. With MSM medium the maximum ethanol amounts reached 0.85 g/l for R. eutropha ΔphaC1 pBBR1MCS-3::atfA/pdc/adhB after 32 h and 0.44 g/l for the control strain after 8 h. If Na-oleate was added to the MSM medium, the maximum ethanol concentration reached 4.38 g/l with R. eutropha ΔphaC1 pBBR1MCS-3::atfA/pdc/adhB after 36 h and 1.34 with the control strain after 30 h. Thus, it could be shown that R. eutropha ΔphaC1 pBBR1MCS-3::atfA/pdc/adhB is able to synthesize three times higher ethanol concentrations as the control strain if grown in MSM with gluconate and Na-oleate.

Possibly FAEE occurrences were analyzed by TLC and GC from lyophilized cell mass. Without the addition of Na-oleate neither cells grown in NB nor those grown in MSM showed ethyloleate synthesis as revealed by GC and TLC analysis. If Na-oleate was added to the medium cell dry mass of *R. eutropha* ΔphaC1 pBBR1MCS-3::atfA/pdc/adhB showed ethyloleate concentrations of 0.45% (w/w) after 36 h and of 0.23% (w/w) after 48 h. The cell dry mass of the control strains gave no peak corresponding to ethyloleate in GC analyses. Comparable to the GC analyses, the TLC analyses of crude extracts of the respective cell dry masses revealed the occurrence of substances corresponding to ethyloleate only in the pBBR1MCS-3::atfA/pdc/adhB containing strain *R. eutropha* ΔphaC1.

While GC/MS analyses of the putative ethyloleate spot scraped from TLC plates gave no results, GC/MS analyses of the ethyloleate containing 36 h sample and the 48 h sample revealed the occurrence of ethylpalmitoleate in the cell dry mass. Other FAEE could not be detected. Thus, if supplemented with Na-oleate strain *R. eutropha* ΔphaC1 pBBR1MCS-3::atfA/pdc/adhB is able to synthesize FAEE.

REFERENCES

Altschul, S. F., W. Gish, W. Miller, E. W. Myers, and D. J. Lipman. 1990. Basic local alignment search tool. J. Mol. Biol. 215:403-410.

Altschul, S. F., T. L. Madden, A. A. Schäffer, J. Zhang, Z. Zhang, W. Miller and D. J. Lipman 1997. Gapped BLAST and PSI-BLAST: a new generation of protein database search programs. Nucleic Acids Res. 25:3389.3402

Anderson, R. L., and V. L. Saplco. 1975. D-fructose (D-mannose) kinase. Methods Enzymol. 42:39-43.

Aneja, K. K., R. D. Ashby, and D. K. Y. Solaiman. 2009. Altered composition of *Ralstonia eutropha* poly(hydroxyalkanoate) through expression of PHA synthase from *Allochromatium vinosum* ATCC 35206. Biotechnol. Lett. 31:1601-1612.

Birnboim, H. C., and J. Doly. 1979. A rapid alkaline extraction procedure for screening recombinant plasmid DNA. Nucleic Acids Res. 7:1513-1523.6.

Bradford, M. M. 1976. A rapid and sensitive method for the quantitation of microgram quantities of protein utilizing the principle of protein-dye binding. Anal. Biochem. 72:248-254.

Buchholz, B. Nordsiek, G., Meister, M. Bowien, B. 1994. Transfer of genes from *Pseudomonas saccharophila* to construct xylose-utilizing strains of *Alcaligenes eutrophus*. Current Microbiology 29:157-162.

Coulombel, C., M. J. Foglietti, and F. Percheron. 1982. Identification and kinetic studies of an inducible mannokinase from a *Streptomyces* strain. Biochim. Biophys. Acta 706:117-122.

Ellasson, A., E. Boles, B. Johansson, M. Österberg, J. M. Thevelein, I. Spencer-Martins, H. Juhnke, and B. Hahn-Hägerdal. 2000. Xylulose fermentation by mutant and wild-type strains of *Zygosaccheromyces* and *Saccharomyces cerevisiae*. Appl. Microbiol. Biotechnol. 53:376-382.

Franklin, F. C. H., M. Bagdasarian, M. M. Bagdasarian, and K. N. Timmis. 1981. Molecular and functional analysis of the TOL plasmid pWWO from *Pseudomonas putida* and cloning of genes for the entire regulated aromatic ring meta cleavage pathway. Proc. Natl. Acad. Sci. USA 78:7458-7462.

Friedrich, B., C. Hogrefe, and H. G. Schlegel. 1981. Naturally occurring genetic transfer of hydrogen-oxidizing ability between strains of *Alcaligenes eutrophus*. J. Bacteriol. 147:198-205.

Gao, Q., M. Zhang, J. D. McMillan, and D. S. Kompala. 2002. Characterization of heterologous and native enzyme activity profiles in metabolically engineered *Zymomonas mobilis* strains during batch fermentation of glucose and xylose mixtures. Appl. Biochem. Biotechnol. 98-100:341-355.

Gottschalk, G., U. Eberhardt, and H. G. Schlegel. 1964. Verwertung von Fructose durch *Hydrogenomonas* H16. Arch. Mikrobiol. 48:95-108.

Hanahan, D. 1983. Studies on transformation of *Escherichia coli* with plasmids. J. Mol. Biol. 188:557-580.

Hirota, Y., H. Suzuki, Y. Nishimura, and S. Yasuda. 1977. On the process of cellular division in *Escherichia coli*: a mutant of *E. coli* lacking a murein-lipoprotein. Proc. Natl. Acad. Sci. U.S.A. 74:1417-1420.

Mike, T., N.-H. Gropp, C. Kaiser, C. Grzesik, B. Kusian, and B. Bowien. 1999. Mutational analysis of the cbb operon ($CO_2$ Assimilation) promoter of *Ralstonia eutropha*. J. Bacteria 181:4374-4380.

Kalscheuer, R., T. Stolting and A. Steinbuchel. 2006. Microdiesel: *Escherichia coli* engineered for fuel production. Microbiology 152:2529-2536

Kang, S., and A. Markovitz. 1967. Induction of capsular polysaccharide synthesis by rho-fluorophenylalanine in *Escherichia coli* wild type and strains with altered phenylalanyl soluble ribonucleic acid synthetase. J. Bacteriol. 93:584-591.

König, C., I. Sammler, E. Wilde, and H. G. Schlegel. 1969. Constitutive glucose-6-phosphate dehydrogenase in mutants utilizing glucose, which are derived from cryptic wildtype strains. Arch. Mikrobiol. 67:51-57.

Kovach, M. E., P. H. Elzer, D. S. Hill, G. T. Robertson, M. A. Farris, R. M. Roop 2nd, and K. M. Peterson. 1995. Four new derivatives of the broad-host-range cloning vector pBBR1MCS, carrying different antibiotic-resistance cassettes. Gene 166:175-176.

Laemmli, U. K. 1970 Cleavage of structural proteins during the assembly of the head of bacteriophage T4. Nature 227:680-685.

Meijnen, J.-P., J. H. de Winde, and H. J. Ruijssenaars. 2008. Engineering *Pseudomonas putida* S12 for efficient utilization of D-xylose and L-arabinose. Appl. Env. Microbiol. 74: 5031-5037.

Park, H.-C., K.-J. Lim, J.-S. Park, Y.-H. Lee, and T.-L. Huh. 1995. High frequency transformation of *Alcaligenes eutrophus* producing poly-β-hydroxybutyric acid by electroporation. Biotechnol. Tech. 9:31-34.

Parker, C., W. O. Barnell, J. L. Snoep, L. O. Ingram, and T. Conway. 1995. Characterization of the *Zymomonas mobilis* glucose facilitator gene product (glf) in recombinant *Escherichia coli*: examination of transport mechanism, kinetics and the role of glucokinase in glucose transport. Mol. Microbiol. 15:795-802.

Peplinski K., Ehrenreich A., Döring C., Bömeke M., Reinecke F., Hutmacher C. and Steinbüchel A., 2010. Genome-Wide transcriptome analyses of the 'Knailgas' bacterium *Ralstonia eutropha* H16 with regard to polyhydroxyalkanoate metabolism. Microbiology, 156:2136-2152

Pohlmann, A., W. F. Fricke, F. Reinecke, B. Kusian, H. Liesegang, R. Cramm, T. Ettinger, C. Ewering, M. Pötter, E. Schwartz, A. Strittmatter, I. Voss, G. Gottschalk, A. Steinbüchel, B. Friedrich, and B. Bowien. 2006. Genome sequence of the bioplastic-producing "Knallgas" bacterium *Ralstonia eutropha* H16. Nat. Biotechnol. 24:1257-1262.

Pries, A., A. Steinbüchel, and H. G. Schlegel. 1990. Lactose and galactose utilizing strains of poly(hydroxyalkanoic acid) accumulating *Alcaligenes eutrophus* and *Pseudomo-* nas saccharophila obtained by recombinant DNA technology. Appl. Microbiol. Biotechnol. 33:410417.

Porthun, A., M. Bernhard, B. Friedrich. 2002: Expression of a functional NAD-reducing [NiFe] hydrogenase from the Gram-positive *Rhodococcus opacus* in the Gram-negative *Ralstonia eutropha*. Arch Microbiol. 177:159-166.

Reinecke, F., and A. Steinbüchel. 2009. *Ralstonia eutropha* strain H16 as model organism for PHA metabolism and for biotechnological production of technically interesting biopolymers. J. Mol. Microbiol. Biotechnol, 16:91-108.

Sambrook, J., E. F. Fritsch, and T. Maniatis, 1989. *Molecular cloning: A Laboratory Manual*. Cold Spring Harbor Press, Cold Spring Harbor, N.Y.

Schlegel, H. G., H. Kaitwasser, and G. Gottschalk. 1961. Ein Submersverfahren zur Kultur wasserstoffoxydierentier Bakterien: Wachstumsphysiologische Untersuchungen. Arch. Microbiol. 38:209-222.

Schlegel, H. G., and G. Gottschalk. 1965. Verwertung von Glucose dutch eine Mutante von *Hydrogenomonas* H16. Biochem. Z. 341:249-259.

Schäferjohann, J., R. Bednarski, and B. Bowien. 1996. Regulation of $CO_2$ assimilation in *Ralstonia eutropha*: Premature transcription termination within the cbb operon. J. Bacteriol. 170: 6714-6719.

Schwartz, E., U. Gerischer, and B. Friedrich. 1998. Transcriptional regulation of *Alcaligenes eutrophus* hydrogenase genes. J. Bacteriol. 180:31974204.

Sebastian, J., and C. Asensio. 1972. Purification and properties of the mannokinase from *Escherichia coli*. Arch. Biochem. Biophys. 151:227-233.

Shamanna, D. K, and K. E. Sanderson. 1979. Uptake and catabolism of D-xylose in *Salmonella typhimurium* LT2. J. Bacteriol. 139:64-70.

Siedow, A., R. Cramm, R. A. Siddiqui, and B. Friedrich. 1999. A megaplasmid-borne anaerobic ribonucleotide reductase in *Alcaligenes eutrophus* H16. J. Bacteriol. 181:4919-4928.

Simon R., Priefer U. and A. Punier. 1983. A broad host range mobilization system for in vivo genetic engineering: transposon mutagenesis in Gram-negative bacteria, *Biotechnology* 1:784-794

Solaiman, D. K. Y., and B. M. Swingle. 2010. Isolation of novel *Pseudomonas syringae* promoters and functional characterization in polyhydroxyalkanoate-producing pseudomonads. New Biotechnol. doi:10.1016/j.nbt.2009.12.803

Solaiman, D. K., B. M. Swingle, and R. D. Ashby. 2010. A new shuttle vector for gene expression in biopolymer-producing *Ralstonia eutropha*. J. Microbiol. Methods doi: 10.1016/j.mimet.2010.04.010.

Stein, S., Levitsky, A., Fateev, O. & Mallard, G. (1998) The NIST Mass Spectral Search Program. Windows-Software Version 1.6d.

Verlinden, R. A. J., Hill, D. J., Kertward, M. A. Williams, C. D. and Radecka, I. 2007. Bacterial synthesis of biodegradable polyhydroxyalkanoates. J. Appl. Microbiol. 102: 1437-1449.

Weber, K., Osborn, M. (1969) The reliability of molecular weight determinations by dodecyl sulfate-polyacrylamide gel electrophoresis. J. Biol. Chem. 244:4406-4412.

West, S. E., H. P. Schweizer, C. Dall, A. K. Sample, and L. J. Runyen-Janecky. 1994. Construction of improved *Escherichia-Pseudomonas* shuttle vectors derived from pUC18/19 and sequence of the region required for their replication in *Pseudomonas aeruginosa*. Gene 148:81-86.

Windhövel, U., and B. Bowlers. 1990. On the operon structure of the cfx gene clusters in *Alcaligenes eutrophus*. Arch. Microbiol. 154:85-91.

---

The invention claimed is:

1. A genetically modified microorganism of the genus *Cupriavidus* or *Ralstonia*, wherein the microorganism is genetically modified to express:
   a) phosphomannose isomerase (EC5.3.1.8) and facilitated diffusion protein for mannose uptake (EC1.3.1.74),
      wherein said microorganism is capable of growing on mannose or glucose as a carbon source, or
   b) (i) xylose isomerase (EC 5.3.1.5),
      (ii) xylulokinase 2.7.1.17), and
      (iii) a high affinity ABC-transporter or xylose proton symporter E,
         wherein said microorganism is capable of growing on xylose, a mixture of xylose and arabinose, glucose, or galactose as a carbon source.

2. The microorganism of claim 1, wherein the microorganism is further genetically modified to express transaldolase (EC2.2.1.2) or transketolase (EC2.2.1.1).

3. The microorganism of claim 1, wherein the microorganism is further genetically modified to express glucokinase (EC 2.7.1.2).

4. The microorganism of claim 1, wherein the microorganism is capable of using mannose, xylose, arabinose, glucose, and galactose as the carbon source.

5. The microorganism of claim wherein the microorganism is *Cupriavidus necator* or *Ralstonia eutropha*.

6. A vector comprising:
   a) a nucleotide sequence encoding phosphomannose isomerase (EC 5.3.1.8) and a nucleotide sequence encoding facilitated diffusion protein for mannose uptake (EC1.3.1.74), and
   b) regulatory elements for regulating expression of each nucleotide sequence in *Cupriavidus* or *Ralstonia*,
   wherein the vector is a plasmid.

7. A vector comprising:
   a) (i) a nucleotide sequence encoding xylose isomerase (EC 5.3.1.5), a nucleotide sequence encoding xylulokinase (EC2.7.1.17), and a nucleotide sequence encoding a high affinity ABC-transporter, or
      (ii) a nucleotide sequence encoding xylose isomerase (EC 5.3.1.5), a nucleotide sequence encoding xylulokinase (EC2.7.1.17) and a nucleotide sequence encoding xylose proton symporter E, and
   b) regulatory elements for regulating expression of each nucleotide sequence in *Cupriavidus* or *Ralstonia*,
   wherein the vector is a plasmid.

8. The vector of claim 6, further comprising a nucleotide sequence encoding transaldolase (EC2.2.1.2) or transketolase (EC.2.2.1.1).

9. The vector of claim 6, further comprising a gene encoding glucokinase (EC2.7.1.2).

10. The vector of claim 6, wherein the regulatory elements comprise a strong constitutive promoter.

11. A vector comprising:
a) a nucleotide sequence encoding phosphomannose isomerase (EC 5.3.1.8) and a nucleotide sequence encoding facilitated diffusion protein for mannose uptake (EC 0.3.1.74), and
b) regulatory elements for regulating expression of each nucleotide sequence in *Cupriavidus* or *Ralstonia*,
wherein the vector is a broad host range vector.

12. A vector comprising:
a) a nucleotide sequence encoding phosphomannose isomerase (EC 5.3.1.8 and a nucleotide sequence encoding facilitated diffusion protein for mannose uptake (EC1.3.1.74), and
b) regulatory elements for regulating expression of each nucleotide sequence in *Cupriavidus* or *Ralstonia*,
wherein the regulatory elements comprise a promoter and the promoter is neokanamycin-promoter, lac-promoter, glyceraldehyde-3-phosphate dehydrogenase promoter, P2, hydrogenase (SH) promoter or $P_L$.

13. A method for cultivating the microorganism according to claim 1, or a *Cupriavidus* or *Ralstonia* microorganism comprising the vector, which comprises that the cultivation medium comprises mannose, glucose, xylose, arabinose, galactose, or a combination thereof as carbon source.

14. The method according to claim 13, which comprises that the microorganism is allowed to synthesize a chemical, such as a lipid and the chemical is recovered from the cultivation medium or from the cells.

15. The method according to claim 13, which comprises that the microorganism is allowed to synthesize polyhydroxyalkanoates, such as PHB, fatty acids, or fatty acid derivatives.

16. The microorganism of claim 1, wherein the microorganism is genetically modified further to express mannofructokinase (EC2.7.1.4).

17. The vector of claim 6, where the vector further comprises a nucleotide sequence encoding mannofructokinase (EC 2.7.1.4).

18. The vector of claim 7, wherein the regulatory elements comprise a strong constitutive promoter.

19. The vector of claim 7, wherein the vector is a broad host range vector.

20. The vector of claim 7, wherein the regulatory elements comprise a promoter and the promoter is neokanamycin-promoter, lac-promoter, glyceraldehyde-3-phosphate dehydrogenase promoter, P2, hydrogenase (SH) promoter or $P_L$.

21. The microorganism of claim 1, wherein the microorganism is genetically modified to express:
(i) xylose isomerase (EC 5.3.1.5),
(ii) xyludokinase (E 2.7.1.17),
(iii) a high affinity ABC-transporter; and
(iv) xylose proton symporter E,
wherein said microorganism is capable of growing on xylose, a mixture of xylose and arabinose, glucose, or galactose as a carbon source.

22. The vector of claim 7, wherein the vector comprises: a nucleotide sequence encoding xylose isomerase (EC 5.3.1.5), a nucleotide sequence encoding xylulokinase (EC2.7.1.17), a nucleotide sequence encoding a high affinity ABC-transporter, and a nucleotide sequence encoding xylose proton symporter E.

23. The vector of claim 6, wherein the vector is a high copy number vector.

24. The vector of claim 7, wherein the vector is as high copy number vector.

\* \* \* \* \*